TODO

| Statistical comparison | Statistical significance |
|---|---|
| Cultrex vs FAQ | p<0.0001 |
| Cultrex vs Ac-FAQ | p<0.0001 |
| Cultrex vs QHL | p<0.0001 |
| Cultrex vs Ac-QHL | p<0.0001 |
| Cultrex vs SSL | p<0.0001 |
| Cultrex vs Ac-SSL | p<0.0001 |
| FAQ vs QHL | p<0.0001 |
| FAQ vs Ac-QHL | p<0.0001 |
| Ac-FAQ vs QHL | p<0.0001 |
| Ac-FAQ vs Ac-QHL | p<0.0001 |
| FAQ vs SSL | p<0.0001 |
| Ac-FAQ vs SSL | p<0.0001 |
| FAQ vs Ac-SSL | p<0.0001 |
| Ac-FAQ vs Ac-SSL | p<0.0001 |

| Statistical comparison | Statistical significance |
|---|---|
| Cultrex vs FAQ | $p<0.0001$ |
| Cultrex vs Ac-FAQ | $p<0.0001$ |
| Cultrex vs Ac-QHL | $p<0.05$ |
| Cultrex vs SSL | $p<0.005$ |
| Cultrex vs Ac-SSL | $p<0.0001$ |
| FAQ vs QHL | $p<0.0001$ |
| FAQ vs Ac-QHL | $p<0.0001$ |
| FAQ vs SSL | $p<0.0001$ |
| FAQ vs Ac-SSL | $p<0.0001$ |
| Ac-FAQ vs QHL | $p<0.0001$ |
| Ac-FAQ vs Ac-QHL | $p<0.0001$ |
| Ac-FAQ vs SSL | $p<0.0001$ |
| Ac-FAQ vs Ac-SSL | $p<0.0001$ |

| Statistical comparison | Statistical significance |
|---|---|
| Cultrex vs FAQ | $p < 0.0001$ |
| Cultrex vs Ac-FAQ | $p < 0.0001$ |
| Cultrex vs Ac-QHL | $p < 0.005$ |
| Cultrex vs SSL | $p < 0.05$ |
| Cultrex vs Ac-SSL | $p < 0.0001$ |
| FAQ vs Ac-FAQ | $p < 0.005$ |

| Statistical comparison | Statistical significance |
|---|---|
| Cultrex vs FAQ | p<0.0001 |
| Cultrex vs Ac-FAQ | p<0.0001 |
| Cultrex vs SSL | p<0.0001 |
| Cultrex vs Ac-SSL | p<0.0001 |
| FAQ vs QHL | p<0.0001 |
| Ac-FAQ vs QHL | p<0.005 |
| FAQ vs Ac-QHL | p<0.005 |
| FAQ vs SSL | p<0.0001 |
| Ac-FAQ vs SSL | p<0.0001 |
| FAQ vs Ac-SSL | p<0.0001 |
| Ac-FAQ vs Ac-SSL | p<0.0001 |

| Statistical comparison | Statistical significance |
|---|---|
| Cultrex vs FAQ | $p<0.05$ |
| Cultrex vs SSL | $p<0.05$ |
| Cultrex vs Ac-SSL | $p<0.0001$ |
| FAQ vs QHL | $p<0.05$ |
| Ac-FAQ vs QHL | $p<0.05$ |
| FAQ vs Ac-QHL | $p<0.05$ |
| FAQ vs SSL | $p<0.05$ |
| Ac-FAQ vs SSL | $p<0.05$ |
| FAQ vs Ac-SSL | $p<0.0001$ |
| Ac-FAQ vs Ac-SSL | $p<0.005$ |

| Statistical comparison | Statistical significance |
|---|---|
| Cultrex vs FAQ | p<0.0001 |
| Cultrex vs Ac-FAQ | p<0.0001 |
| Cultrex vs SSL | p<0.0001 |
| Cultrex vs Ac-SSL | p<0.0001 |
| FAQ vs QHL | p<0.0001 |
| Ac-FAQ vs QHL | p<0.0001 |
| FAQ vs Ac-QHL | p<0.0001 |
| Ac-FAQ vs Ac-QHL | p<0.0001 |
| FAQ vs SSL | p<0.0001 |
| Ac-FAQ vs SSL | p<0.0001 |
| FAQ vs Ac-SSL | p<0.0001 |
| Ac-FAQ vs Ac-SSL | p<0.0001 |

FUNCTIONALIZED BIOMATERIALS FOR TISSUE REGENERATION

This application is a national stage application under 35 U.S.C. §371 of PCT International Application No. PCT/EP2012/054458, filed Mar. 14, 2012, which claims the benefit of PCT International Application No. PCT/EP2011/053838, filed on Mar. 15, 2011, which are hereby incorporated by reference in their entirety.

FIELD OF THE INVENTION

The present invention concerns the field of functionalized self-assembling peptides suitable for obtaining hydrogels for use in a wide range of applications in the biomedical field, such as for the development of biomaterials for regenerative medicine.

STATE OF THE ART

Cell replacement is a crucial step for the regeneration of central nervous system (CNS) lesions, in which endogenous regenerative mechanisms cannot supplant the function of lost cells. One of the most important objectives of regenerative medicine is to obtain standardized and viable cell populations that maintain their phenotype and their biological activities upon transplantation and in in vitro cultures. A variety of cells has been used for tissue engineering. Primary cells can be derived from the patient's tissue, avoiding immunological rejection, but in general they are post-mitotic thus featuring a limited proliferative potential; moreover, during the expansion period in culture, the cells can de-differentiate and acquire inappropriate phenotypic characteristics (1). Due to these limitations, stem cells have been studied for their potential in solving most of the drawbacks typical of mature primary cells.

The discovery of the Neural Stem Cells (NSC) (2) with neurogenic capabilities in the developing and adult brain has raised new possibilities for repairing the damaged nervous system (3-5). Regardless of their potential, the success of cell transplantation therapies is not only influenced by the protocols for the isolation and differentiation of stem cells, but also relies on the method by which cells are engrafted and induced to functionally integrate into the affected tissue.

Cells are naturally located in 3-dimensional (3D) microenvironments in vivo, where they are surrounded by other cells and by the extracellular matrix (ECM), whose components: collagen, elastin, or laminin, are organized in nanostructures (i.e. fibers, triple helixes, etc.) with specific bioactive motifs that regulate the cell homeostasis.

The potential of success of stem cell transplantation can only be guaranteed by the microenvironment that is created and the presence of a 3D scaffold with optimal motifs, could stimulate differentiation and survival of the specific type of stem cells to be seeded in the scaffold and allow tissue regeneration.

The need and importance is increasingly felt for the development of scaffolds that create synthetic microenvironments providing 3D supports, capable of controlling and directing specific cell-substrate interactions and to warrant proper integration, upon transplantation, of the stem cells within the host tissues.

The object of the present invention is therefore the development of improved self assembling peptides and their use as biomaterials and as scaffolds for tissue regeneration, which overcome the disadvantages related to cell replacement therapies in transplantation.

SUMMARY OF THE INVENTION

The present invention concerns a self-assembling peptide (SAP) comprising:

a heptapeptide domain selected from the group comprising:

| | |
|---|---|
| -FAQRVPP- | SEQ ID N. 1 |
| -QHLPRDH- | SEQ ID N. 2 |
| -SSLSVND- | SEQ ID N. 3 |
| -YIIPMHD- | SEQ ID N. 4 |
| -SLPKLPP- | SEQ ID N. 5 |
| -TPLSSHS- | SEQ ID N. 6 |
| -SASHWQI- | SEQ ID N. 7 |
| -LQAIPRN- | SEQ ID N. 8 |
| -YRMPIWP- | SEQ ID N. 9 |
| -KLPGWSG- | SEQ ID N. 10 |
| -HAIYPRH- | SEQ ID N. 11 |
| -GETRAPL- | SEQ ID N. 12 |
| -ALTPWAF- | SEQ ID N. 13 |
| -GKPMPPM- | SEQ ID N. 14 |
| -SILPYPY- | SEQ ID N. 15 | a spacer region; and a backbone region.

The present invention therefore concerns a novel group of self-assembling peptides (SAPs or SAPeptides), wherein said SAPs are peptides comprising a heptapeptide domain, a spacer region and a backbone region, and are optionally acetylated (Ac) and non-acetylated.

A preferred form of the SAPs according to the present invention is a SAP selected from the group consisting of:

```
X-FAQRVPPGGGLDLKLDLKLDLK-Y;
X-QHLPRDHGGGLDLKLDLKLDLK-Y;
X-SSLSVNDGGGLDLKLDLKLDLK-Y;
X-YIIPMHDGGGLDLKLDLKLDLK-Y;
X-SLPKLPPGGGLDLKLDLKLDLK-Y;
X-TPLSSHSGGGLDLKLDLKLDLK-Y;
X-SASHWQIGGGLDLKLDLKLDLK-Y;
X-LQAIPRNGGGLDLKLDLKLDLK-Y;
X-YRMPIWPGGGLDLKLDLKLDLK-Y;
X-KLPGWSGGGGLDLKLDLKLDLK-Y;
X-HAIYPRHGGGLDLKLDLKLDLK-Y;
X-GETRAPLGGGLDLKLDLKLDLK-Y;
X-ALTPWAFGGGLDLKLDLKLDLK-Y;
X-GKPMPPMGGGLDLKLDLKLDLK-Y;
and
X-SILPYPYGGGLDLKLDLKLDLK-Y;
``` wherein X is $NH_2$ or acetylated (Ac), and wherein Y is $CONH_2$ or COOH.

For the purposes of the present invention, each SAP has a corresponding SEQ ID NO., as indicated in the following detailed description.

Advantageously, in a more preferred embodiment, the present invention relates to a SAP selected from the group consisting of:

| | |
|---|---|
| SEQ ID NO. 16: | $NH_2$-FAQRVPPGGGLDLKLDLKLDLK-$CONH_2$; |
| SEQ ID NO. 17: | Ac-FAQRVPPGGGLDLKLDLKLDLK-$CONH_2$; |
| SEQ ID NO. 18: | $NH_2$-QHLPRDHGGGLDLKLDLKLDLK-$CONH_2$; |
| SEQ ID NO. 19: | Ac-QHLPRDHGGGLDLKLDLKLDLK-$CONH_2$; |
| SEQ ID NO. 20: | $NH_2$-SSLSVNDGGGLDLKLDLKLDLK-$CONH_2$; |
| SEQ ID NO. 21: | Ac-SSLSVNDGGGLDLKLDLKLDLK-$CONH_2$; |
| SEQ ID NO. 22: | $NH_2$-YIIPMHDGGGLDLKLDLKLDLK-$CONH_2$; |
| SEQ ID NO. 23: | Ac-YIIPMHDGGGLDLKLDLKLDLK-$CONH_2$; |
| SEQ ID NO. 24: | $NH_2$-SLPKLPPGGGLDLKLDLKLDLK-$CONH_2$; |
| SEQ ID NO. 25: | Ac-SLPKLPPGGGLDLKLDLKLDLK-$CONH_2$; |
| SEQ ID NO. 26: | $NH_2$-TPLSSHSGGGLDLKLDLKLDLK-$CONH_2$; |
| SEQ ID NO. 27: | Ac-TPLSSHSGGGLDLKLDLKLDLK-$CONH_2$. |
| SEQ ID NO. 28: | $NH_2$-SASHWQIGGGLDLKLDLKLDLK-$CONH_2$; |
| SEQ ID NO. 29: | Ac-SASHWQIGGGLDLKLDLKLDLK-$CONH_2$; |
| SEQ ID NO. 30: | $NH_2$-LQAIPRNGGGLDLKLDLKLDLK-$CONH_2$; |
| SEQ ID NO. 31: | Ac-LQAIPRNGGGLDLKLDLKLDLK-$CONH_2$; |
| SEQ ID NO. 32: | $NH_2$-YRMPIWPGGGLDLKLDLKLDLK-$CONH_2$; |
| SEQ ID NO. 33: | Ac-YRMPIWPGGGLDLKLDLKLDLK-$CONH_2$; |
| SEQ ID NO. 34: | $NH_2$-KLPGWSGGGLDLKLDLKLDLK-$CONH_2$; |
| SEQ ID NO. 35: | Ac-KLPGWSGGGLDLKLDLKLDLK-$CONH_2$; |
| SEQ ID NO. 36: | $NH_2$-HAIYPRHGGGLDLKLDLKLDLK-$CONH_2$; |
| SEQ ID NO. 37: | Ac-HAIYPRHGGGLDLKLDLKLDLK-$CONH_2$. |
| SEQ ID NO. 38: | $NH_2$-GETRAPLGGGLDLKLDLKLDLK-$CONH_2$; |
| SEQ ID NO. 39: | Ac-GETRAPLGGGLDLKLDLKLDLK-$CONH_2$; |
| SEQ ID NO. 40: | $NH_2$-ALTPWAFGGGLDLKLDLKLDLK-$CONH_2$; |
| SEQ ID NO. 41: | Ac-ALTPWAFGGGLDLKLDLKLDLK-$CONH_2$; |
| SEQ ID NO. 42: | $NH_2$-GKPMPPMGGGLDLKLDLKLDLK-$CONH_2$; |
| SEQ ID NO. 43: | Ac-GKPMPPMGGGLDLKLDLKLDLK-$CONH_2$. |
| SEQ ID NO. 44: | $NH_2$-SILPYPYGGGLDLKLDLKLDLK-$CONH_2$; |
| SEQ ID NO. 45: | Ac-SILPYPYGGGLDLKLDLKLDLK-$CONH_2$; |
| SEQ ID NO. 46: | $NH_2$-FAQRVPPGGGLDLKLDLKLDLK-COOH; |
| SEQ ID NO. 47: | Ac-FAQRVPPGGGLDLKLDLKLDLK-COOH; |
| SEQ ID NO. 48: | $NH_2$-QHLPRDHGGGLDLKLDLKLDLK-COOH; |
| SEQ ID NO. 49: | Ac-QHLPRDHGGGLDLKLDLKLDLK-COOH; |
| SEQ ID NO. 50: | $NH_2$-SSLSVNDGGGLDLKLDLKLDLK-COOH; |
| SEQ ID NO. 51: | Ac-SSLSVNDGGGLDLKLDLKLDLK-COOH; |
| SEQ ID NO. 52: | $NH_2$-YIIPMHDGGGLDLKLDLKLDLK-COOH; |
| SEQ ID NO. 53: | Ac-YIIPMHDGGGLDLKLDLKLDLK-COOH; |
| SEQ ID NO. 54: | $NH_2$-SLPKLPPGGGLDLKLDLKLDLK-COOH; |
| SEQ ID NO. 55: | Ac-SLPKLPPGGGLDLKLDLKLDLK-COOH; |
| SEQ ID NO. 56: | $NH_2$-TPLSSHSGGGLDLKLDLKLDLK-COOH; |
| SEQ ID NO. 57: | Ac-TPLSSHSGGGLDLKLDLKLDLK-COOH. |
| SEQ ID NO. 58: | $NH_2$-SASHWQIGGGLDLKLDLKLDLK-COOH; |
| SEQ ID NO. 59: | Ac-SASHWQIGGGLDLKLDLKLDLK-COOH; |
| SEQ ID NO. 60: | $NH_2$-LQAIPRNGGGLDLKLDLKLDLK-COOH; |
| SEQ ID NO. 61: | Ac-LQAIPRNGGGLDLKLDLKLDLK-COOH; |
| SEQ ID NO. 62: | $NH_2$-YRMPIWPGGGLDLKLDLKLDLK-COOH; |
| SEQ ID NO. 63: | Ac-YRMPIWPGGGLDLKLDLKLDLK-COOH; |
| SEQ ID NO. 64: | $NH_2$-KLPGWSGGGLDLKLDLKLDLK-COOH; |
| SEQ ID NO. 65: | Ac-KLPGWSGGGLDLKLDLKLDLK-COOH; |
| SEQ ID NO. 66: | $NH_2$-HAIYPRHGGGLDLKLDLKLDLK-COOH; |
| SEQ ID NO. 67: | Ac-HAIYPRHGGGLDLKLDLKLDLK-COOH. |
| SEQ ID NO. 68: | $NH_2$-GETRAPLGGGLDLKLDLKLDLK-COOH; |
| SEQ ID NO. 69: | Ac-GETRAPLGGGLDLKLDLKLDLK-COOH; |
| SEQ ID NO. 70: | $NH_2$-ALTPWAFGGGLDLKLDLKLDLK-COOH; |
| SEQ ID NO. 71: | Ac-ALTPWAFGGGLDLKLDLKLDLK-COOH; |
| SEQ ID NO. 72: | $NH_2$-GKPMPPMGGGLDLKLDLKLDLK-COOH; |
| SEQ ID NO. 73: | Ac-GKPMPPMGGGLDLKLDLKLDLK-COOH. |
| SEQ ID NO. 74: | $NH_2$-SILPYPYGGGLDLKLDLKLDLK-COOH; |
| SEQ ID NO. 75: | Ac-SILPYPYGGGLDLKLDLKLDLK-COOH. |

A further aspect of the present invention is a hydrogel comprising the self-assembling peptides according to the present invention and a hydrogelating ingredient.

A still further aspect of the present invention is a self-assembling peptide polymer comprising at least two self-assembling peptides according to the present invention.

In a further embodiment, the invention provides a tabular nanofiber comprising at least two self-assembling peptides according to the present invention.

In a still further embodiment, the invention provides a complex interwoven membrane comprising at least two tabular nanofibres according to the present invention.

A further aspect of the present invention is a self-assembling peptide polymer comprising at least two self-assembling peptides according to the present invention, for use as a medicament.

A further aspect of the present invention is a self-assembling peptide polymer comprising at least two self-assembling peptides according to the present invention, for use as a scaffold in tissue regeneration.

A still further aspect of the present invention is a self-assembling peptide according to the present invention, for use as a biomaterial.

A still further aspect of the present invention is a heptapeptide according to the present invention, for use as a marker for neural stem cells (NSC).

A still further aspect of the present invention provides a method for the selection and identification of a least one SAP sequence, or heptapeptide for biomaterial functionalization, comprising the steps of:

(a) contacting a bacteriophage library expressing a plurality of peptides with a cell;
(b) removing unbound bacteriophages;
(c) identifying the peptide presented by the bound bacteriophages
(d) linking the peptide identified in step (c) to a spacer region and to a backbone region.

Advantageously the method according to the present invention is a method for the selection and identification of a functionalized SAP described above by a SEQ ID NO. from SEQ ID NO. 16 to SEQ ID NO. 75.

Moreover, the method according to the present invention allows to develop ad hoc functionalizations for biomaterials, and in particular SAPs for the specific tissues to be regenerated or cells to be transplanted.

As will be further described in the detailed description of the invention, the self-assembling peptides of the present invention have the advantage of being useful in the development of biomaterials.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-9, wherein:

In FIG. 1 (A) the increment in the neuronal population is quantified.

FIG. 5 (C) and FIG. 5 (D) are graphs of the proliferation assays for murine and for human NSCs respectively as described in Example 8.

DETAILED DESCRIPTION OF THE INVENTION

Figure 1A:
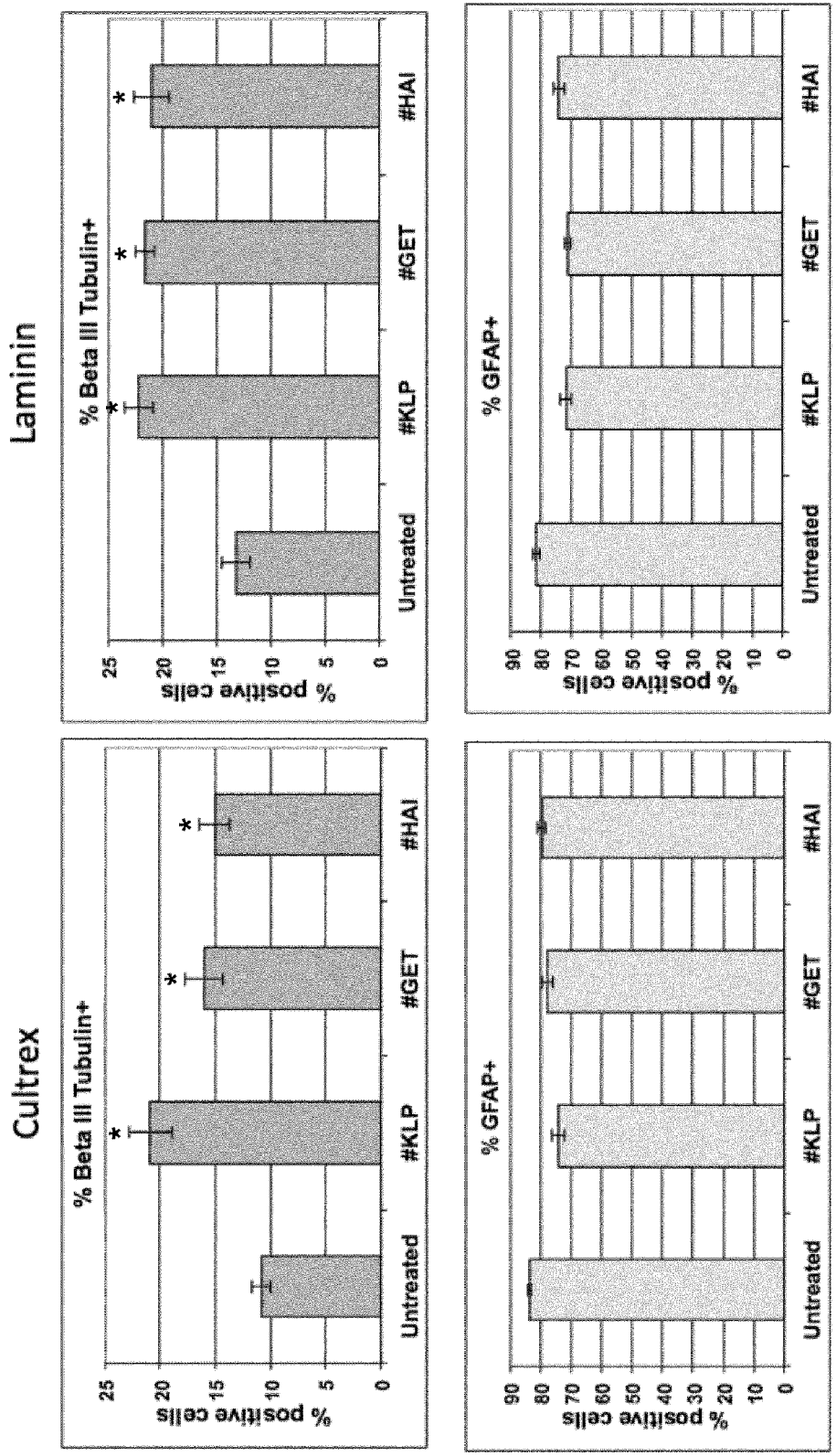
FIG. 1 (A) and FIG. 1 (B) show the effect of the exposure to the chosen heptapeptides over NSC differentiation.
FIG. 1(B) depicts differentiated neurons marker for βIII Tubulin obtained from NSC cultured over Cultrex and Laminin substrates when exposed to the heptapeptides described in Example 3.

The self-assembling peptide (SAP) according to the present invention comprises:

a heptapeptide domain selected from the group comprising:

| | |
|---|---|
| -FAQRVPP- | SEQ ID N. 1 |
| -QHLPRDH- | SEQ ID N. 2 |
| -SSLSVND- | SEQ ID N. 3 |
| -YIIPMHD- | SEQ ID N. 4 |
| -SLPKLPP- | SEQ ID N. 5 |
| -TPLSSHS- | SEQ ID N. 6 |
| -SASHWQI- | SEQ ID N. 7 |
| -LQAIPRN- | SEQ ID N. 8 |

```
-YRMPIWP-           SEQ ID N. 9

-KLPGWSG-           SEQ ID N. 10

-HAIYPRH-           SEQ ID N. 11

-GETRAPL-           SEQ ID N. 12

-ALTPWAF-           SEQ ID N. 13

-GKPMPPM-           SEQ ID N. 14

-SILPYPY-           SEQ ID N. 15
``` a spacer region; and
a backbone region.

For the purposes of the present invention, the heptapeptide domains or heptapeptides have an aminoacid sequence and a corresponding SEQ ID NO. as follows:
SEQ ID NO. 1 corresponds to the aminoacidic sequence of: FAQRVPP;
SEQ ID NO. 2 corresponds to the aminoacidic sequence of: QHLPRDH;
SEQ ID NO. 3 corresponds to the aminoacidic sequence of: SSLSVND;
SEQ ID NO. 4 corresponds to the aminoacidic sequence of: YIIPMHD;
SEQ ID NO. 5 corresponds to the aminoacidic sequence of: SLPKLPP;
SEQ ID NO. 6 corresponds to the aminoacidic sequence of: TPLSSHS;
SEQ ID NO. 7 corresponds to the aminoacidic sequence of: SASHWQI;
SEQ ID NO. 8 corresponds to the aminoacidic sequence of: LQAIPRN;
SEQ ID NO. 9 corresponds to the aminoacidic sequence of: YRMPIWP;
SEQ ID NO. 10 corresponds to the aminoacidic sequence of: KLPGWSG;
SEQ ID NO. 11 corresponds to the aminoacidic sequence of: HAIYPRH;
SEQ ID NO. 12 corresponds to the aminoacidic sequence of: GETRAPL;
SEQ ID NO. 13 corresponds to the aminoacidic sequence of: ALTPWAF;
SEQ ID NO. 14 corresponds to the aminoacidic sequence of: GKPMPPM;
SEQ ID NO. 15 corresponds to the aminoacidic sequence of: SILPYPY.

The amino acid sequences defined above use the one letter IUPAC amino acid codes (ie. G corresponds to the amino acid Glycine, P corresponds to the amino acid Proline).

In a preferred embodiment, the present invention concerns a self-assembling peptide (SAP) comprising:
a heptapeptide domain selected from the group comprising:

```
-FAQRVPP-           SEQ ID N. 1

-QHLPRDH-           SEQ ID N. 2

-SSLSVND-           SEQ ID N. 3

-YIIPMHD-           SEQ ID N. 4

-SLPKLPP-           SEQ ID N. 5

-TPLSSHS-           SEQ ID N. 6

-SASHWQI-           SEQ ID N. 7

-LQAIPRN-           SEQ ID N. 8

-YRMPIWP-           SEQ ID N. 9

-KLPGWSG-           SEQ ID N. 10

-HAIYPRH-           SEQ ID N. 11

-GETRAPL-           SEQ ID N. 12

-ALTPWAF-           SEQ ID N. 13

-GKPMPPM-           SEQ ID N. 14

-SILPYPY-           SEQ ID N. 15
``` a spacer region; and
a backbone region.

According to a more preferred aspect, the spacer region of the self-assembling peptide of the present invention comprises from one to seven glycine amino acid units (G).

Preferably said spacer region comprises three glycine amino acid units (Gly Gly Gly or GGG). The spacer region may also comprise one to seven alanine amino acid units (A), however, Glycine is preferred for its higher conformational flexibility as it contains a hydrogen as its side chain rather than a carbon as is the case in all other amino acids. In particular the insertion of longer glycines-spacers between the self-assembling cores and the functional motifs improves the effectiveness of SAPeptides functionalization, thus providing better tools for in vitro studies in cell biology and for applications in regenerative therapies in vivo.

The backbone region comprises one or more self-assembling amino acid repetitions or amino acid repetition units or self-assembling amino acid repetition units.

Without being bound to any theory, the inventors believe that SAPs according to the present invention are self-assembling, and therefore undergo spontaneous assembling, due to the self-assembling features of the backbone region.

The SAPs according to the present invention have been identified and linked by the single common inventive concept of being peptides having a predominance of hydrophobic non-polar aminoacids. SAPs according to the present invention in fact have such a predominance in the heptapeptide domain, in the spacer region which contributes to the conformational flexibility of the SAP and in the backbone region, which due to the strong hydrophobic balance, contributes to the stability and allows to form a nanostructure which can have a larger number of possible functionalizations. The technical relationship which links the SAPs according to the present invention and makes a contribution over the prior art can be seen in the methodology by which the functional motifs have been discovered and in the particular structure of the presently claimed SAPs.

A preferred aspect of the present invention relates to a SAP wherein the backbone region comprises at least one amino acid repetition unit selected from the group consisting of LDLK (SEQ ID NO: 91), KFEF (SEQ ID NO: 92), RADA (SEQ ID NO: 93), LDLD (SEQ ID NO: 94) and LKLK (SEQ ID NO: 95).

In the present invention with the term "LDLK amino acid repetition unit" or "LDLK amino acid repetition" is intended the unit which is repeated in the backbone region of the SAP. One LDLK repetition or repetition unit is Leu Asp Leu Lys or LDLK (SEQ ID NO: 91), two LDLK repetition units are the following amino acids: LDLKLDLK (SEQ ID NO: 96).

In the present invention with the term "KFEF amino acid repetition unit" or "KFEF amino acid repetition" is intended the unit which is repeated in the backbone region of the SAP. Two KFEF repetition units are the following amino acids: KFEFKFEF (SEQ ID NO: 97).

According to a more preferred aspect, the backbone region comprises at least two LDLK (SEQ ID NO: 91), RADA (SEQ ID NO: 93), LDLD (SEQ ID NO: 94), LKLK (SEQ ID NO: 95) or KFEF (SEQ ID NO: 92) amino acid repetitions or one -GGGPFSSTKT- (SEQ ID NO: 98), -WGGGPFSSTKT- (SEQ ID NO: 99), -GGGPFSSTDT- (SEQ ID NO: 100), -GGGPFSSTNT- (SEQ ID NO: 101), -GGGPFSSTET- (SEQ ID NO: 102), -GGGPFSSTQT- (SEQ ID NO: 103), -GGGAFSSTKT- (SEQ ID NO: 104), -GGGPFSETKT- (SEQ ID NO: 105), -GGGAFSSTKTGRGD- (SEQ ID NO: 106), -GGGPFSSTRT- (SEQ ID NO: 107), -GGGAFASTKT- (SEQ ID NO: 108), -GGGGGPFSSTKT- (SEQ ID NO: 109), -GGGPWSSTKT- (SEQ ID NO: 110), -GGG(Propylamine)FSSTKT- (SEQ ID NO: 111), -WGGGAFASTKT- (SEQ ID NO: 112), -WGGGAFSSTKT- (SEQ ID NO: 113), -GGGKFSSTPT- (SEQ ID NO: 114), -GGGPKSSTFT- (SEQ ID NO: 115), -GGGPFSSKTT- (SEQ ID NO: 116), -GGGPFSSTTK- (SEQ ID NO: 117) or -PFSSTKT- (SEQ ID NO: 118) repetition.

According to a preferred aspect, the backbone region comprises at least two LDLK (Leu Asp Leu Lys or LDLK; SEQ ID NO: 91) amino acid repetitions.

Preferably said backbone region comprises three LDLK amino acid repetitions (LDLKLDLKLDLK (SEQ ID NO: 119) or (LDLK)₃).

Preferably said backbone region comprises four LDLK amino acid repetitions (LDLKLDLKLDLKLDLK (SEQ ID NO: 120) or (LDLK)₄).

The LDLK backbone region, featuring a stronger hydrophobic balance, allows for synthesis of a shorter backbone sequence (lowering down production costs and increasing synthesis yield) and for a more stable self-assembled nanostructure, allowing for a larger number of possible functionalizations. In particular the LDLK backbone region consists of the alternation of: one non-polar amino acid, one acid amino acid, one non-polar amino acid and ends with a basic amino acid.

This particular structure of the backbone region has the advantage of allowing the SAPs to easily form hydrogels.

A preferred form of the SAPs according to the present invention is a SAP selected from the group consisting of:

```
X-FAQRVPPGGGLDLKLDLKLDLK-Y;

X-QHLPRDHGGGLDLKLDLKLDLK-Y;

X-SSLSVNDGGGLDLKLDLKLDLK-Y;

X-YIIPMHDGGGLDLKLDLKLDLK-Y;

X-SLPKLPPGGGLDLKLDLKLDLK-Y;

X-TPLSSHSGGGLDLKLDLKLDLK-Y;

X-SASHWQIGGGLDLKLDLKLDLK-Y;

X-LQAIPRNGGGLDLKLDLKLDLK-Y;

X-YRMPIWPGGGLDLKLDLKLDLK-Y;

X-KLPGWSGGGGLDLKLDLKLDLK-Y;

X-HAIYPRHGGGLDLKLDLKLDLK-Y;
```

```
-continued
X-GETRAPLGGGLDLKLDLKLDLK-Y;

X-ALTPWAFGGGLDLKLDLKLDLK-Y;

X-GKPMPPMGGGLDLKLDLKLDLK-Y;
and

X-SILPYPYGGGLDLKLDLKLDLK-Y;
``` wherein X is NH₂ or acetylated (Ac), and wherein Y is CONH₂ or COOH.

Advantageously, preferred SAPs of the present invention, have an amino acid sequence and a corresponding SEQ ID NO. chosen from the group comprising:

SEQ ID NO. 16 corresponds to: NH₂-FAQRVPPGGGLD-LKLDLKLDLK-CONH₂;
SEQ ID NO. 17 corresponds to: Ac-FAQRVPPGGGLD-LKLDLKLDLK-CONH₂;
SEQ ID NO. 18 corresponds to: NH₂-QHLPRDHGGGLD-LKLDLKLDLK-CONH₂;
SEQ ID NO. 19 corresponds to: Ac-QHLPRDHGGGLD-LKLDLKLDLK-CONH₂;
SEQ ID NO. 20 corresponds to: NH₂-SSLSVNDGGGLD-LKLDLKLDLK-CONH₂;
SEQ ID NO. 21 corresponds to: Ac-SSLSVNDGGGLD-LKLDLKLDLK-CONH₂;
SEQ ID NO. 22 corresponds to: NH₂-YIIPMHDGGGLD-LKLDLKLDLK-CONH₂;
SEQ ID NO. 23 corresponds to: Ac-YIIPMHDGGGLD-LKLDLKLDLK-CONH₂;
SEQ ID NO. 24 corresponds to: NH₂-SLPKLPPGGGLD-LKLDLKLDLK-CONH₂;
SEQ ID NO. 25 corresponds to: Ac-SLPKLPPGGGLD-LKLDLKLDLK-CONH₂;
SEQ ID NO. 26 corresponds to: NH₂-TPLSSHSGGGLD-LKLDLKLDLK-CONH₂;
SEQ ID NO. 27 corresponds to: Ac-TPLSSHSGGGLD-LKLDLKLDLK-CONH₂.
SEQ ID NO. 28 corresponds to: NH₂-SASHWQIGGGLD-LKLDLKLDLK-CONH₂;
SEQ ID NO. 29 corresponds to: Ac-SASHWQIGGGLD-LKLDLKLDLK-CONH₂;
SEQ ID NO. 30 corresponds to: NH₂-LQAIPRNGGGLD-LKLDLKLDLK-CONH₂;
SEQ ID NO. 31 corresponds to: Ac-LQAIPRNGGGLD-LKLDLKLDLK-CONH₂;
SEQ ID NO. 32 corresponds to: NH₂-YRMPIWPGGGLD-LKLDLKLDLK-CONH₂;
SEQ ID NO. 33 corresponds to: Ac-YRMPIWPGGGLD-LKLDLKLDLK-CONH₂;
SEQ ID NO. 34 corresponds to: NH₂-KLPGWSGGGGLD-LKLDLKLDLK-CONH₂;
SEQ ID NO. 35 corresponds to: Ac-KLPGWSGGGGLD-LKLDLKLDLK-CONH₂;
SEQ ID NO. 36 corresponds to: NH₂-HAIYPRHGGGLD-LKLDLKLDLK-CONH₂;
SEQ ID NO. 37 corresponds to: Ac-HAIYPRHGGGLD-LKLDLKLDLK-CONH₂.
SEQ ID NO. 38 corresponds to: NH₂-GETRAPLGGGLD-LKLDLKLDLK-CONH₂;
SEQ ID NO. 39 corresponds to: Ac-GETRAPLGGGLD-LKLDLKLDLK-CONH₂;
SEQ ID NO. 40 corresponds to: NH₂-ALTPWAFGGGLD-LKLDLKLDLK-CONH₂;
SEQ ID NO. 41 corresponds to: Ac-ALTPWAFGGGLD-LKLDLKLDLK-CONH₂;

SEQ ID NO. 42 corresponds to: NH$_2$-GKPMPPMGGGLD-LKLDLKLDLK-CONH$_2$;
SEQ ID NO. 43 corresponds to: Ac-GKPMPPMGGGLD-LKLDLKLDLK-CONH$_2$.
SEQ ID NO. 44 corresponds to: NH$_2$-SILPYPYGGGLD-LKLDLKLDLK-CONH$_2$;
SEQ ID NO. 45 corresponds to: Ac-SILPYPYGGGLD-LKLDLKLDLK-CONH$_2$;
SEQ ID NO. 46 corresponds to: NH$_2$-FAQRVPPGGGLD-LKLDLKLDLK-COOH;
SEQ ID NO. 47 corresponds to: Ac-FAQRVPPGGGLD-LKLDLKLDLK-COOH;
SEQ ID NO. 48 corresponds to: NH$_2$-QHLPRDHGGGLD-LKLDLKLDLK-COOH;
SEQ ID NO. 49 corresponds to: Ac-QHLPRDHGGGLD-LKLDLKLDLK-COOH;
SEQ ID NO. 50 corresponds to: NH$_2$-SSLSVNDGGGLD-LKLDLKLDLK-COOH;
SEQ ID NO. 51 corresponds to: Ac-SSLSVNDGGGLD-LKLDLKLDLK-COOH;
SEQ ID NO. 52 corresponds to: NH$_2$-YIIPMHDGGGLD-LKLDLKLDLK-COOH;
SEQ ID NO. 53 corresponds to: Ac-YIIPMHDGGGLD-LKLDLKLDLK-COOH;
SEQ ID NO. 54 corresponds to: NH$_2$-SLPKLPPGGGLD-LKLDLKLDLK-COOH;
SEQ ID NO. 55 corresponds to: Ac-SLPKLPPGGGLD-LKLDLKLDLK-COOH;
SEQ ID NO. 56 corresponds to: NH$_2$-TPLSSHSGGGLD-LKLDLKLDLK-COOH;
SEQ ID NO. 57 corresponds to: Ac-TPLSSHSGGGLD-LKLDLKLDLK-COOH.
SEQ ID NO. 58 corresponds to: NH$_2$-SASHWQIGGGLD-LKLDLKLDLK-COOH;
SEQ ID NO. 59 corresponds to: Ac-SASHWQIGGGLD-LKLDLKLDLK-COOH;
SEQ ID NO. 60 corresponds to: NH$_2$-LQAIPRNGGGLD-LKLDLKLDLK-COOH;
SEQ ID NO. 61 corresponds to: Ac-LQAIPRNGGGLD-LKLDLKLDLK-COOH;
SEQ ID NO. 62 corresponds to: NH$_2$-YRMPIWPGGGLD-LKLDLKLDLK-COOH;
SEQ ID NO. 63 corresponds to: Ac-YRMPIWPGGGLD-LKLDLKLDLK-COOH;
SEQ ID NO. 64 corresponds to: NH$_2$-KLPGWSGGGGLD-LKLDLKLDLK-COOH;
SEQ ID NO. 65 corresponds to: Ac-KLPGWSGGGGLD-LKLDLKLDLK-COOH;
SEQ ID NO. 66 corresponds to: NH$_2$-HAIYPRHGGGLD-LKLDLKLDLK-COOH;
SEQ ID NO. 67 corresponds to: Ac-HAIYPRHGGGLD-LKLDLKLDLK-COOH.
SEQ ID NO. 68 corresponds to: NH$_2$-GETRAPLGGGLD-LKLDLKLDLK-COOH;
SEQ ID NO. 69 corresponds to: Ac-GETRAPLGGGLD-LKLDLKLDLK-COOH;
SEQ ID NO. 70 corresponds to: NH$_2$-ALTPWAFGGGLD-LKLDLKLDLK-COOH;
SEQ ID NO. 71 corresponds to: Ac-ALTPWAFGGGLD-LKLDLKLDLK-COOH;
SEQ ID NO. 72 corresponds to: NH$_2$-GKPMPPMGGGLD-LKLDLKLDLK-COOH;
SEQ ID NO. 73 corresponds to: Ac-GKPMPPMGGGLD-LKLDLKLDLK-COOH.
SEQ ID NO. 74 corresponds to: NH$_2$-SILPYPYGGGLD-LKLDLKLDLK-COOH;
SEQ ID NO. 75 corresponds to: Ac-SILPYPYGGGLD-LKLDLKLDLK-COOH.

As indicated above the amino acid sequences use the one letter IUPAC amino acid codes These SAPs are of synthetic origin and are therefore easy to manufacture in large quantities, and they can be modified chemically and biologically. Such modifications allow to construct an ultra-structure promoting cell adhesion and tissue regeneration. The SAPs of the present invention provide the advantages of high biocompatibility which allows them to overcome the problems of tissue rejection, absence of pathogen transfer which is a high risk during implantation, selective and slow drug release due to their 3 dimensional structure and, easy functionalization with bioactive motifs, which therefore allows these SAPs to be very versatile in their use in different applications.

In a further embodiment, these SAPs are peptide-based scaffolds which self-assemble in mild solvent conditions, and easily form hydrogels. Such a hydrogelation is driven by the formation of non-covalent interactions in water, including hydrogen bonding, hydrophobic, electrostatic, and π-π interactions which lead to the formation of organized supramolecular assemblies that can give rise to nanofibers, nanotubes and nanoparticles. Such nanostructured materials also display hydrophilic-hydrophobic residues which provide cross-β-sheet self-assembled nanostructures of easy functionalization and are capable of creating microenvironments suited for triggering tissue regeneration.

These SAPs have the further advantage of being of synthetic origin, and therefore do not have the drawbacks seen in natural peptides such as the tendency to induce inflammatory response and pathogen transfer due to undefined factors that cannot be eliminated by purification prior to implantation, the significant degree of variability between different lots and the difficulty of availability of large scale sources.

Without wishing to be bound to any theory, these SAPs have the advantage of being low molecular weight self-assembling peptides and therefore easier and faster to assemble and to synthesize.

In a preferred embodiment the self-assembling peptide according to the present invention comprise a heptapeptide domain selected from the group consisting of SEQ ID NO. 1, 2 and 3.

In a more preferred embodiment the self-assembling peptide according to the present invention comprise the heptapeptide domain SEQ ID NO. 1.

In a further aspect the present invention provides a self-assembling peptide wherein the N-terminus is optionally modified.

In a still further aspect the present invention provides a self-assembling peptide wherein said N-terminus modification is an acetylation (Ac).

In a further aspect the present invention provides a self-assembling peptide wherein the C-terminus is optionally modified.

In a still further aspect the present invention provides a self-assembling peptide wherein said C-terminus has a CONH$_2$ group.

In a preferred aspect the invention provides the self-assembling peptides selected from the group consisting of:

| | |
|---|---|
| NH$_2$-FAQRVPPGGGLDLKLDLKLDLK-CONH$_2$; | SEQ ID N. 16 |
| Ac-FAQRVPPGGGLDLKLDLKLDLK-CONH$_2$; | SEQ ID N. 17 |
| NH$_2$-QHLPRDHGGGLDLKLDLKLDLK-CONH$_2$; | SEQ ID N. 18 |

| | |
|---|---|
| Ac-QHLPRDHGGGLDLKLDLKLDLK-CONH$_2$; | SEQ ID N. 19 |
| NH$_2$-SSLSVNDGGGLDLKLDLKLDLK-CONH$_2$; | SEQ ID N. 20 |
| Ac-SSLSVNDGGGLDLKLDLKLDLK-CONH$_2$; | SEQ ID N. 21 |
| NH$_2$-KLPGWSGGGGLDLKLDLKLDLK-CONH$_2$; | SEQ ID NO. 34 |
| Ac-KLPGWSGGGGLDLKLDLKLDLK-CONH$_2$; | SEQ ID NO. 35 |
| NH$_2$-FAQRVPPGGGLDLKLDLKLDLK-COOH; | SEQ ID NO. 46 |
| Ac-FAQRVPPGGGLDLKLDLKLDLK-COOH; | SEQ ID NO. 47 |
| NH$_2$-QHLPRDHGGGLDLKLDLKLDLK-COOH; | SEQ ID NO. 48 |
| Ac-QHLPRDHGGGLDLKLDLKLDLK-COOH; | SEQ ID NO. 49 |
| NH$_2$-SSLSVNDGGGLDLKLDLKLDLK-COOH; | SEQ ID NO. 50 |
| Ac-SSLSVNDGGGLDLKLDLKLDLK-COOH; | SEQ ID NO. 51 |
| NH$_2$-KLPGWSGGGGLDLKLDLKLDLK-COOH; and | SEQ ID NO. 64 |
| Ac-KLPGWSGGGGLDLKLDLKLDLK-COOH. | SEQ ID NO. 65 |

In a more preferred aspect the invention provides the self-assembling peptides selected from the group consisting of:

| | |
|---|---|
| NH$_2$-FAQRVPPGGGLDLKLDLKLDLK-CONH$_2$; | SEQ ID N. 16 |
| Ac-FAQRVPPGGGLDLKLDLKLDLK-CONH$_2$; | SEQ ID N. 17 |
| NH$_2$-FAQRVPPGGGLDLKLDLKLDLK-COOH; and | SEQ ID NO. 46 |
| Ac-FAQRVPPGGGLDLKLDLKLDLK-COOH. | SEQ ID NO. 47. |

Preferred SAPs showed an enhanced stimulation of NSC proliferation and enhanced neuronal and oligodendroglial differentiation of mouse neural stem cells (mNSC) and human neural stem cells (hNSCs). Preferred SAPs selected from the group consisting of SEQ ID N.16, SEQ ID N.17, SEQ ID N.18, SEQ ID N.19, SEQ ID N.20, SEQ ID N.21, SEQ ID N.34, SEQ ID N.35, SEQ ID N.46, SEQ ID N.47, SEQ ID N.48, SEQ ID N.49, SEQ ID N.50, SEQ ID N.51, SEQ ID N.64 and SEQ ID N.65, more preferably SAPs selected from the group consisting of SEQ ID N.16, SEQ ID N.17, SEQ ID N.46 and SEQ ID N.47, and still more preferably SAPs selected from the group consisting of SEQ ID N.16 and SEQ ID N.17, showed an improved locomotor recovery of acutely injured rats, and did not alter the physiological inflammatory response following SCI, and enhanced nervous regeneration within the malacic nervous tissue in vivo. SAPs according to the present invention therefore enhance transplanted cell survival, stimulate host tissue growth and allow to obtain a controlled release of pro-regenerative cytokines. Moreover SAPs can advantageously be used as hemostat solutions among other applications.

A further aspect of the present invention is a hydrogel comprising the self-assembling peptides according to the present invention and a hydrogelating ingredient.

These functionalized hydrogels, have the potential to become very similar to the fibrous component of the extra cellular matrix, making them the ideal candidates for supporting two and three dimensional cell cultures and fostering human and murine NSCs proliferation and differentiation.

A further aspect of the present invention is that these functionalized hydrogels can be used for enhancing human colon stem cell and human colon cancer stem cell proliferation and/or differentiation in vitro, providing the appropriate physical soft microenvironment and chemical functionalization for cell crypt formation.

A still further aspect of the present invention is a self-assembling peptide polymer comprising at least two self-assembling peptides according to the present invention.

In a further embodiment, the invention provides a tabular nanofiber comprising at least two self-assembling peptides according to the present invention.

In a still further embodiment, the invention provides a complex interwoven membrane comprising at least two tabular nanofibres according to the present invention.

A further aspect of the present invention is a self-assembling peptide polymer comprising at least two self-assembling peptides according to the present invention, for use as a medicament.

A further aspect of the present invention is a self-assembling peptide polymer comprising at least two self-assembling peptides according to the present invention, for use as a scaffold in tissue regeneration.

The SAPs according to the present invention could be advantageously used in the development of the complex polymers for effective tissue engineering and for the development of biomaterials and biological prostheses to assist or enhance motor control lost by trauma, disease, or defect.

The self-assembling peptide polymer according to the present invention, for use as a scaffold in tissue regeneration wherein said tissue is a tissue of the CNS.

Tissues of the CNS such as nerves, can be damaged through trauma which may lead to the severance of nerves or disease, such as stroke, multiple sclerosis, diabetes, spina bifida, and polio. The most dramatic and serious nerve damage occurs to the spinal cord.

As there is no cure for nerve damage, the SAPs of the present invention are advantageously used in developing tailored scaffolds for a regenerative medicine applications such as regeneration of spinal cord injury, and for nerve regeneration.

A still further aspect of the present invention is a self-assembling peptide according to the present invention, for use as a biomaterial.

Without being bound to any theory, a biomaterial is any matter, surface, or construct that interacts with biological systems or a substance that has been engineered to take a form which, alone or as part of a complex system, is used to direct, by control of interactions with components of living systems, the course of any therapeutic or diagnostic procedure.

A still further aspect of the present invention is a heptapeptide according to the present invention, for use as a marker for neural stem cells (NSC). Such heptapeptides are selected from the group comprising:

| | |
|---|---|
| -FAQRVPP- | SEQ ID N. 1 |
| -QHLPRDH- | SEQ ID N. 2 |
| -SSLSVND- | SEQ ID N. 3 |
| -YIIPMHD- | SEQ ID N. 4 |
| -SLPKLPP- | SEQ ID N. 5 |
| -TPLSSHS- | SEQ ID N. 6 |
| -SASHWQI- | SEQ ID N. 7 |
| -LQAIPRN- | SEQ ID N. 8 |

| | |
|---|---|
| -YRMPIWP- | SEQ ID N. 9 |
| -KLPGWSG- | SEQ ID N. 10 |
| -HAIYPRH- | SEQ ID N. 11 |
| -GETRAPL- | SEQ ID N. 12 |
| -ALTPWAF- | SEQ ID N. 13 |
| -GKPMPPM- | SEQ ID N. 14 |
| -SILPYPY- | SEQ ID N. 15. |

Markers are frequently used to characterize stem cell populations and provide a useful tool for initially identifying as well as isolating stem cells. The heptapeptides (functional motifs) according to the present invention have been proved to identify neural stem cell populations, useful quality for stem cell research and regenerative medicine.

A still further aspect of the present invention provides a method for the selection and identification of a least one SAP, or heptapeptide for biomaterial functionalization, sequence comprising the steps of:
(a) contacting a bacteriophage library expressing a plurality of peptides with a cell;
(b) removing unbound bacteriophages; and
(c) identifying the peptide presented by the bound bacteriophages; and
(d) linking the peptide identified in step (c) to a spacer region and to a backbone region.

The method according to the present invention allows to develop ad hoc functionalizations for biomaterials, and in particular SAPs and heptapeptides for the specific tissues to be regenerated or cells to be transplanted. Moreover, SAPs, mixed with phage targeted pro-regenerative cytokines, may allow for synergically integrated tissue engineering approaches fostering, slow drug delivery, transplanted cell engraftment and host tissue in growth.

The method according to the present invention may be used both with cells which are cultured in adhesion and/or in suspension in vitro.

The technology according to the present invention uses libraries of bacteriophages that display short peptides on their surface. After incubation with target cells followed by washing, the phages expressing sequences with a high affinity for specific cell surface molecules is captured by target cells and selected through recovery. This method may identify novel cell ligands for biomaterial functionalization against a number of cell types (cellular transplantation and/or enhanced host tissue response to the implants) and cytokines (slow or triggered drug release) for regenerative medicine applications (regeneration of cartilage, bone, skin, liver, etc.) as well as for tumor targeting.

A preferred aspect of the present invention provides a method for the selection and identification of a least one SAP sequence wherein said cell of step (a) is selected from the group consisting of Neural stem cells, endothelial cells, neurons, osteoblasts, hemotopoietic stem cells, adipocytes, condrocytes, keratinocytes, liver progentior cells, colon stem cells, hepatocytes, embryonic and somatic stem cells, myocytes and cardiomiocytes.

A more preferred aspect of the present invention provides a method for the selection and identification of a least one SAP sequence wherein said cell of step (a) is a Neural stem cell.

A preferred aspect of the present invention provides a method for the selection and identification of a least one SAP sequence wherein said SAP sequence is selected from the group consisting of:

| | |
|---|---|
| SEQ ID NO. 16: | $NH_2$-FAQRVPPGGGLDLKLDLKLDLK-$CONH_2$; |
| SEQ ID NO. 17: | Ac-FAQRVPPGGGLDLKLDLKLDLK-$CONH_2$; |
| SEQ ID NO. 18: | $NH_2$-QHLPRDHGGGLDLKLDLKLDLK-$CONH_2$; |
| SEQ ID NO. 19: | Ac-QHLPRDHGGGLDLKLDLKLDLK-$CONH_2$; |
| SEQ ID NO. 20: | $NH_2$-SSLSVNDGGGLDLKLDLKLDLK-$CONH_2$; |
| SEQ ID NO. 21: | Ac-SSLSVNDGGGLDLKLDLKLDLK-$CONH_2$; |
| SEQ ID NO. 22: | $NH_2$-YIIPMHDGGGLDLKLDLKLDLK-$CONH_2$; |
| SEQ ID NO. 23: | Ac-YIIPMHDGGGLDLKLDLKLDLK-$CONH_2$; |
| SEQ ID NO. 24: | $NH_2$-SLPKLPPGGGLDLKLDLKLDLK-$CONH_2$; |
| SEQ ID NO. 25: | Ac-SLPKLPPGGGLDLKLDLKLDLK-$CONH_2$; |
| SEQ ID NO. 26: | $NH_2$-TPLSSHSGGGLDLKLDLKLDLK-$CONH_2$; |
| SEQ ID NO. 27: | Ac-TPLSSHSGGGLDLKLDLKLDLK-$CONH_2$. |
| SEQ ID NO. 28: | $NH_2$-SASHWQIGGGLDLKLDLKLDLK-$CONH_2$; |
| SEQ ID NO. 29: | Ac-SASHWQIGGGLDLKLDLKLDLK-$CONH_2$; |
| SEQ ID NO. 30: | $NH_2$-LQAIPRNGGGLDLKLDLKLDLK-$CONH_2$; |
| SEQ ID NO. 31: | Ac-LQAIPRNGGGLDLKLDLKLDLK-$CONH_2$; |
| SEQ ID NO. 32: | $NH_2$-YRMPIWPGGGLDLKLDLKLDLK-$CONH_2$; |
| SEQ ID NO. 33: | Ac-YRMPIWPGGGLDLKLDLKLDLK-$CONH_2$; |
| SEQ ID NO. 34: | $NH_2$-KLPGWSGGGGLDLKLDLKLDLK-$CONH_2$; |
| SEQ ID NO. 35: | Ac-KLPGWSGGGGLDLKLDLKLDLK-$CONH_2$; |
| SEQ ID NO. 36: | $NH_2$-HAIYPRHGGGLDLKLDLKLDLK-$CONH_2$; |
| SEQ ID NO. 37: | Ac-HAIYPRHGGGLDLKLDLKLDLK-$CONH_2$. |
| SEQ ID NO. 38: | $NH_2$-GETRAPLGGGLDLKLDLKLDLK-$CONH_2$; |
| SEQ ID NO. 39: | Ac-GETRAPLGGGLDLKLDLKLDLK-$CONH_2$; |
| SEQ ID NO. 40: | $NH_2$-ALTPWAFGGGLDLKLDLKLDLK-$CONH_2$; |
| SEQ ID NO. 41: | Ac-ALTPWAFGGGLDLKLDLKLDLK-$CONH_2$; |
| SEQ ID NO. 42: | $NH_2$-GKPMPPMGGGLDLKLDLKLDLK-$CONH_2$; |
| SEQ ID NO. 43: | Ac-GKPMPPMGGGLDLKLDLKLDLK-$CONH_2$. |
| SEQ ID NO. 44: and | $NH_2$-SILPYPYGGGLDLKLDLKLDLK-$CONH_2$; |
| SEQ ID NO. 45: | Ac-SILPYPYGGGLDLKLDLKLDLK-$CONH_2$ |
| SEQ ID NO. 46: | $NH_2$-FAQRVPPGGGLDLKLDLKLDLK-COOH; |
| SEQ ID NO. 47: | Ac-FAQRVPPGGGLDLKLDLKLDLK-COOH; |
| SEQ ID NO. 48: | $NH_2$-QHLPRDHGGGLDLKLDLKLDLK-COOH; |
| SEQ ID NO. 49: | Ac-QHLPRDHGGGLDLKLDLKLDLK-COOH; |
| SEQ ID NO. 50: | $NH_2$-SSLSVNDGGGLDLKLDLKLDLK-COOH; |
| SEQ ID NO. 51: | Ac-SSLSVNDGGGLDLKLDLKLDLK-COOH; |
| SEQ ID NO. 52: | $NH_2$-YIIPMHDGGGLDLKLDLKLDLK-COOH; |
| SEQ ID NO. 53: | Ac-YIIPMHDGGGLDLKLDLKLDLK-COOH; |
| SEQ ID NO. 54: | $NH_2$-SLPKLPPGGGLDLKLDLKLDLK-COOH; |
| SEQ ID NO. 55: | Ac-SLPKLPPGGGLDLKLDLKLDLK-COOH; |

-continued

SEQ ID NO. 56: NH$_2$-TPLSSHSGGGLDLKLDLKLDLK-COOH;

SEQ ID NO. 57: Ac-TPLSSHSGGGLDLKLDLKLDLK-COOH.

SEQ ID NO. 58: NH$_2$-SASHWQIGGGLDLKLDLKLDLK-COOH;

SEQ ID NO. 59: Ac-SASHWQIGGGLDLKLDLKLDLK-COOH;

SEQ ID NO. 60: NH$_2$-LQAIPRNGGGLDLKLDLKLDLK-COOH;

SEQ ID NO. 61: Ac-LQAIPRNGGGLDLKLDLKLDLK-COOH;

SEQ ID NO. 62: NH$_2$-YRMPIWPGGGLDLKLDLKLDLK-COOH;

SEQ ID NO. 63: Ac-YRMPIWPGGGLDLKLDLKLDLK-COOH;

SEQ ID NO. 64: NH$_2$-KLPGWSGGGGLDLKLDLKLDLK-COOH;

SEQ ID NO. 65: Ac-KLPGWSGGGGLDLKLDLKLDLK-COOH;

SEQ ID NO. 66: NH$_2$-HAIYPRHGGGLDLKLDLKLDLK-COOH;

SEQ ID NO. 67: Ac-HAIYPRHGGGLDLKLDLKLDLK-COOH.

SEQ ID NO. 68: NH$_2$-GETRAPLGGGLDLKLDLKLDLK-COOH;

SEQ ID NO. 69: Ac-GETRAPLGGGLDLKLDLKLDLK-COOH;

SEQ ID NO. 70: NH$_2$-ALTPWAFGGGLDLKLDLKLDLK-COOH;

SEQ ID NO. 71: Ac-ALTPWAFGGGLDLKLDLKLDLK-COOH;

SEQ ID NO. 72: NH$_2$-GKPMPPMGGGLDLKLDLKLDLK-COOH;

SEQ ID NO. 73: Ac-GKPMPPMGGGLDLKLDLKLDLK-COOH.

SEQ ID NO. 74: NH$_2$-SILPYPYGGGLDLKLDLKLDLK-COOH;

SEQ ID NO. 75: Ac-SILPYPYGGGLDLKLDLKLDLK-COOH..

EXAMPLES

Example 1

Neural Stem Cell Proliferation and Differentiation

Murine and Human neural precursor cultures are established and expanded as previously described (6) Egf-Generated Cns Progenitor Cells. Neuron 1993, 11, 951-66).

Murine neural precursors isolated from the sub ventricular zone (SVZ) of 8-week-old CD-1 albino mice striata, at passage 10, were used. Human NSCs were isolated from the central nervous system, in particular the diencephalon and the cerebral cortex of human brain 10.5 weeks from conception as previously described 43. The modalities for obtaining the primary tissue are in agreement with the guidelines of the European Network for Transplantation (NECTAR).

Cell proliferation (both for human and murine neural stem cells) was performed in NS-A serum-free medium (Euroclone, Irvine, UK), in the presence of basic fibroblast growth factor (βFGF from PeproTech, Rocky Hill, N.J.) and epidermal growth factor (EGF from PeproTech) at final concentrations of 10 ng/ml and 20 ng/ml. The medium without growth factors was used as a basal medium.

Bulk cultures of mouse and human NSCs were generated by mechanically dissociating neurospheres and plating cells in untreated flasks at the appropriate density ($1 \times 10^4$ cells/cm$^2$) every 4-5 days in the same growth medium. Cell counting and viability was performed at every passage, using trypan blue exclusion.

Example 2

Phage Biopanning

Two days prior cell seeding murine NSCs were mechanically dissociated in order to seed the maximum percentage of stem cells.

NSCs, three million per plate, were seeded over Laminin coated 10 cm Petri dishes (Falcon). After an overnight incubation in 10 ml of βFGF supplemented (10 ng/ml) neural basal media, cells were washed with pre-warmed Incubation Medium.

The Ph.D.-7 phage library was used (New England Biolabs), composed of phage clones with random 7-mer peptides fused to the N-terminal of PIII, a minor coat protein of M13 phage.

Before biopanning experiments against NSCs in adhesion, the phage library was incubated in a Laminin-coated tissue culture dish in order to remove phages with affinity to the Laminin coated plastic surface (negative selection). Mouse Laminin (10 mL at 25 µg/ml concentration) (Roche) was incubated overnight at 37° C. $10^{12}$ cfu of phages were incubated for one hour at 37° C. in pre-warmed Incubation Medium (DMEM supplemented with 0.1% BSA) in Laminin-coated plastic surfaces (setting for adhering NSCs) or plain plastic surfaces (setting for NSCs in suspension). Then incubation Medium and a total volume of five washes of Washing Buffer (DPBS supplemented with 1% BSA and 0.05% Tween-20) were collected and eluted phages were amplified as described in the standard protocol of New England Biolabs.

$10^{12}$ cfu of the negatively selected phage library were diluted in 10 ml Incubation Medium and pipetted onto the adhering NSCs or NSCs in suspension.

After 1 hour of incubation at 37° C. cells were washed five times with pre-warmed Washing Buffer, cell membrane bound phages (MP) and internalized clones (IP) were recovered from independent duplicates of differentiating progenies by eluting and/or lysing the cells respectively. The cell surface was stripped by a 5 minutes incubation of 5 ml of Glycine Buffer (0.2 M Glycine-HCl supplemented with 1 mg/ml BSA (pH 2.2)) at RT. Eluted Phages were neutralized with 5 ml of 1 M Tris-HCl buffer (pH 8) and amplified.

Cells were then lysed with 9 ml of Lysing Buffer (0.1% TEA in PBS) for 5 minutes at RT. Internalized phages were neutralized with 1 ml of 1 M Tris-HCl buffer.

Neutralized phages were titered by infection of *Escherichia coli* to monitor the selection. Internalized and eluted phages were amplified separately for another round of selection. Three rounds of positive selection were performed. At round number two and three the biopannings of internalized and eluted phages were performed in different cell cultures (but with identical culture conditions) by collecting the phages of interest (i.e. internalized phages from libraries of internalized phages) and discarding the leftovers.

After the third round of biopanning, phage clones were randomly picked out from the titer plates and sequenced. Thirty phage plaques per each set of phages were randomly picked for sequencing. A small number of clones wasn't successfully sequenced. The highest consensus was shown for FAQRVPP (SEQ ID NO: 1) (53.5% for IP and 62.5% for MP), QHLPRDH (SEQ ID NO: 2) (14.2% for IP and 8.3% for MP) and SSLSVND (SEQ ID NO: 3) (10.7% for IP and 4.2% for MP) detected in both IP and MP phages as can be seen in Table 1A. In the case of panning against NSC in suspension the highest consensus was for KLPGWSG (SEQ ID NO: 10) (47.36 for MP), GETRAPL (SEQ ID NO: 12) (14.28% for IP and 10.52% for MP) and HAIYPRH (SEQ ID NO: 11) (28.57% for IP and 5.26% for MP).

TABLE 1A

| Internalized phage clones | | | Eluted phage clones | | |
|---|---|---|---|---|---|
| Sequence | Frequency | % | Sequence | Frequency | % |
| FAQRVPP | 15 | 53.5 | FAQRVPP | 15 | 62.5 |
| QHLPRDH | 4 | 14.2 | QHLPRDH | 2 | 8.3 |
| SSLSVND | 3 | 10.7 | SSLSVND | 1 | 4.2 |
| YIIPMHD | 1 | 3.5 | YIIPMHD | 1 | 4.2 |
| SLPKLPP | 1 | 3.5 | SSELVTH | 1 | 4.2 |
| TPLSSHS | 1 | 3.5 | TAVNSDA | 1 | 4.2 |
| SASHWQI | 1 | 3.5 | TPPFAAW | 1 | 4.2 |
| LQAIPRN | 1 | 3.5 | TTTPTTP | 1 | 4.2 |
| YRMPIWP | 1 | 3.5 | LTTGSGS | 1 | 4.2 |

Table 1B shows the sequences of the phages recovered after three rounds of biopanning of NSCs cultured in suspension.

| Internalized phage clones | | | Eluted phage clones | | |
|---|---|---|---|---|---|
| Sequence | Frequency | % | Sequence | Frequency | % |
| HAIYPRH | 4 | 28.57 | KLPGWSG | 9 | 47.36 |
| GETRAPL | 2 | 14.28 | HAIYPRH | 1 | 5.26 |
| SILPYPY | 2 | 14.28 | GETRAPL | 2 | 10.52 |
|  |  |  | ALTPWAF | 2 | 10.52 |
|  |  |  | GKPMPPM | 2 | 10.52 |

For homology identification the primary peptide sequences were compared to the NCBI database using the BLAST program to align short, nearly exact matches.

No full homological protein sequences were identified, however some potentially relevant homologies are shown in Table 2A and Table 2B: ranging from a portion of the Microtubule-affinity regulating kinase 1 (MARK1), relevant in neuronal differentiation, in the case of FAQ, to the mitochondria precursor of intermembrane enzyme Sulfite Oxidase, whose deficiency gives neurological abnormalities fatal at early age, in the case of QHL, to the Activine A Type 1 Receptor, influencing the neuronal differentiation in some cell lines, for SSL. On the other hand, fractions of KLP were found in several FGF-like domains of MEGF10 protein, predominantly expressed in the brain and known to function as a phagocytic receptor, while GET showed a relevant homology for the Cadherin EGF G-type receptor 2.

TABLE 2A

| Peptide Sequence | Protein | Accession |
|---|---|---|
| FAQRVPP | Microtubule Affinity-Regulating Kinase MARK1 (581-585) | NP_663490 |

TABLE 2A-continued

| Peptide Sequence | Protein | Accession |
|---|---|---|
| QHLPRDH | Sulphite Oxidase, Mitochondrial Precursor (356-362) | NP_776094 |
| SSLSVND | Activine A, Receptor Type 1 (55-61) | CAM15401 |

Potentially relevant sequence homologies identified by BLAST in mouse: underlined amino acids stand for exact matches with known peptide sequences.

TABLE 2B

| Peptide Sequence | Protein | Accession |
|---|---|---|
| KLPGWSG | MEGF10 (561-565), Notch1 | Q6DIB5.1 |
| GETRAPL | Cadherin EGF Receptor 2 (5-10), Chordin | XP_537042.2 |
| HAIYPRH | Neurocon Precursor, Glucosylceramidase (210-215) | Q69ZF3.2 |

Example 3

Neurogenic Effect of #KLP, #GET and #HAI Sequences Over NSC Cultures in Vitro

The following sequences were synthesized as listed in Table 3 to assess their effect over NSC differentiation.

TABLE 3

| Peptides Sequence | Acronym |
|---|---|
| NH$_2$-KLPGWSG-CONH$_2$ | #KLP |
| NH$_2$-GETRAPL-CONH$_2$ | #GET |
| NH$_2$-HAIYPRH-CONH$_2$ | #HAI |

Peptides of the present section were synthesized on a 0.1 mmol scale with standard fluorenylmethoxycarbonyl solid-phase techniques using a CEM Liberty automated microwave peptide synthesizer. MBHA rink amide resin (0.5 mmol/g substitution) was used to produce C-terminal amides; activation was performed with 0.5 M HOBt/HBTU in DMF. Peptides were then cleaved from the resin and deprotected with 9 ml of 95% trifluoroacetic acid (TFA), 2.5% water and 2.5% triisopropylsilane. The cleaved peptides were precipitated, washed several times with cold diethyl ether and dissolved in 20-25% of acetonitrile solution prior to be lyophilized and stored at −20° C. Crude peptides were analyzed and purified by reverse phase HPLC using a Waters system equipped with an analytical and semi-preparative BioBasic C4 (Thermo Scientific, UK). Eluents were 0.1% (v/v) TFA in water (Buffer A) and 0.1% (v/v) TFA in acetonitrile (Buffer B). Identity of the peptides was confirmed with MALDI-TOF mass spectrometry. After purification, 0.1 M HCl exchange was performed at a volume of 1:1 in order to extract residual TFA. Then, peptides were lyophilized again.

In vitro tests were performed as previously described (8), in order to assess whether the heptapeptides obtained of the present invention influence NSCs differentiation.

Murine cells (at a concentration of 2×10$^4$ cells/cm$^2$) were seeded in each well (96 multi-well plate) previously coated with Cultrex-BME® substrate (R&D systems) (1:100 dilution in basal medium, overnight incubation) or with Laminin (Roche) (1:5 dilution in PBS 1×, pH 7.4, overnight incubation).

Initially, cells were cultured with basal medium supplemented with βFGF (10 ng/ml), added to enhance neuronal progeny differentiation. At 3 days in vitro (DIV), βFGF medium was replaced with Leukemia Inhibitory Factor (LIF, Chemicon) (20 ng/ml) and Brain Derived Neurotrophic Factor (BDNF, Peprotech) (20 ng/ml). Fresh medium was added every three days. The chosen peptides were dissolved in all cell culture media (but not in the coatings) at a concentration of 0.1 mg/ml.

Immunofluorescence tests were performed for assaying the phenotypes of the differentiated murine NSC progenies. The following antibodies were used: rabbit polyclonal against GFAP (1:500, DakoCytomation) for astrocytes and mouse monoclonal against βIII-Tubulin (1:500, Covance) for neurons. Secondary Abs were Goat anti Mouse Alexa 488 (1:1000, Molecular Probes), Goat anti Mouse Cy3 (1:1000, Jackson Immunoresearch), Cell nuclei were counterstained with DAPI (Molecular Probes). Quantitative analyses were performed by counting 100-300 cells for each of 9 randomly chosen fields over a total of 3 independent experiments.

Values, reported as means±standard error of the mean (FIG. 1A).

Figure 1B:
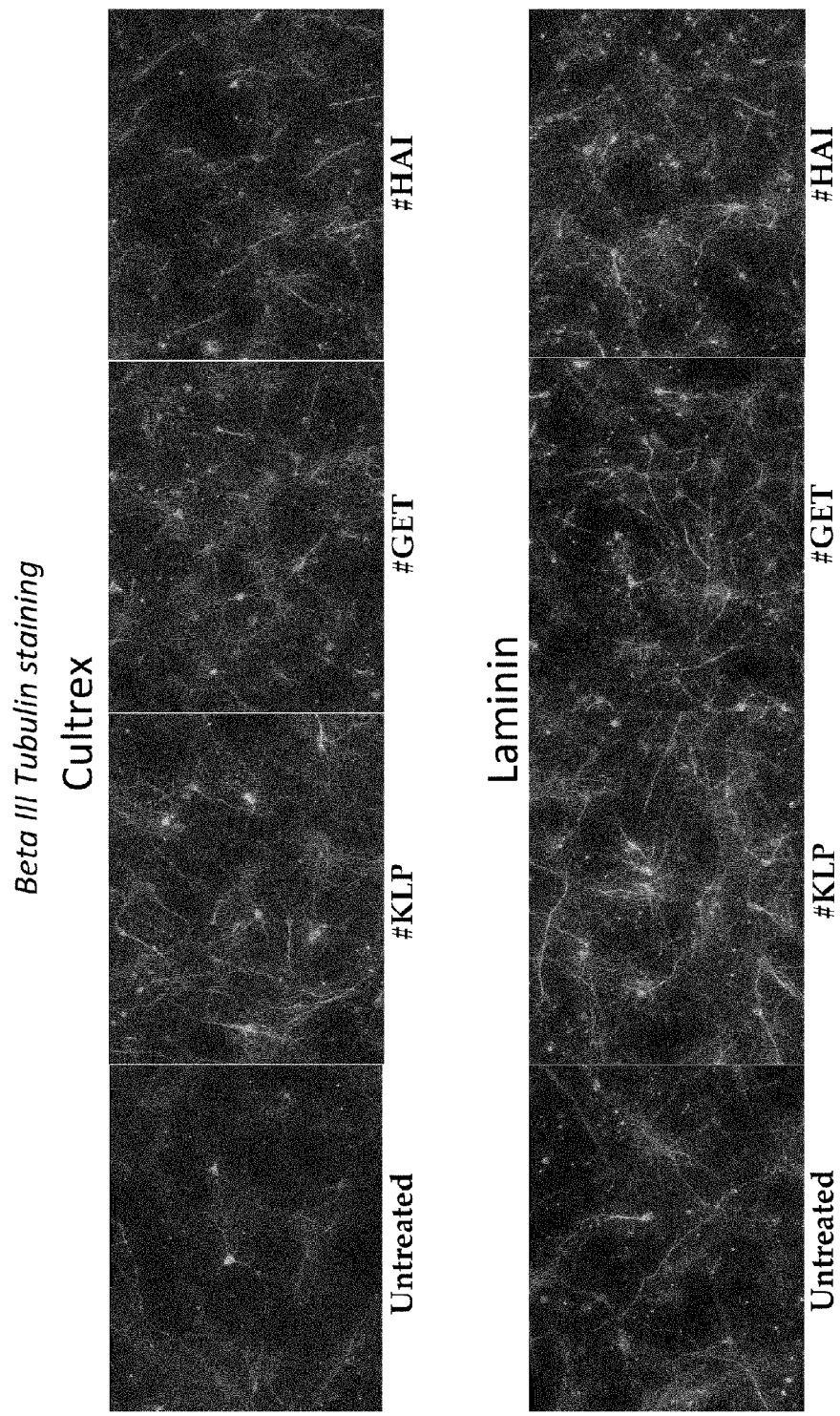

Results:

At 12 days in vitro (DIV) differentiated mouse NSC showed a significant increase in the percentage of differentiated neurons (Beta III Tubulin staining) in both Cultrex and Laminin coated wells upon exposure to #KLP, #GET and #HAI, at the expenses of the percentage of differentiated astrocytes (GFAP staining). Neuronal increase was significant (* $p<0.05$) in all treated NSCs vs untreated NSCs. Highest increase of the neuronal phenotype was detected for #KLP in both cases. These results show that the discovered peptides can influence NSC differentiation toward the neural phenotype (FIG. 1B).

Example 4

Self-Assembling Peptide Functionalization and Purification

The SAPS according to the present invention were synthesized as listed in Table 4:

TABLE 4

| Functionalized SAPeptides | Acronym |
|---|---|
| $NH_2$-FAQRVPP-GGG-LDLKLDLKLDLK-$CONH_2$ | FAQ |
| Ac-FAQRVPP-GGG-LDLKLDLKLDLK-$CONH_2$ | Ac-FAQ |
| $NH_2$-QHLPRDH-GGG-LDLKLDLKLDLK-$CONH_2$ | QHL |
| Ac-OHLPRDH-GGG-LDLKLDLKLDLK-$CONH_2$ | Ac-QHL |
| $NH_2$-SSLSVND-GGG-LDLKLDLKLDLK-$CONH_2$ | SSL |
| Ac-SSLSVND-GGG-LDLKLDLKLDLK-$CONH_2$ | Ac-SSL |
| $NH_2$-KLPGWSG-GGG-LDLKLDLKLDLK-$CONH_2$ | KLP |
| Ac-KLPGWSG-GGG-LDLKLDLKLDLK-$CONH_2$ | Ac-KLP |

The most recurrent clone sequences were synthesized as functional motifs linked, via a 3-glycines spacer, to the N-termini of a self-assembling peptide LDLKLDLKLDLK (SEQ ID NO: 119) backbone sequence, proven to spontaneously fold in β-sheets upon exposure to neutral pH solutions giving injectable hydrogels as follows:

Ac-1234567-GGG-LDLKLDLKLDLK (SEQ ID NO: 119)-$CONH_2$ $NH_2$-1234567-GGG-LDLKLDLKLDLK(SEQ ID NO: 119)-$CONH_2$

Wherein starting from the N-termini: Ac is an acetyl group for improving peptide stability and $NH_2$ is an ammine group of the original sequences, 1234567 is a hepta-peptide, GGG is a spacer comprising three Glycine peptides, LDLKLDLKLDLK (SEQ ID NO: 119) or $(LDLK)_3$, $CONH_2$ is a carbonyl functional group located at the C-termini.

Without being bound to any theory, self-assembling peptides of the present invention may also be synthesized in the reverse order:

Ac-LDLKLDLKLDLK (SEQ ID NO: 119)-GGG-1234567-$CONH_2$ $NH_2$-LDLKLDLKLDLK (SEQ ID NO: 119)-GGG-1234567-$CONH_2$

Self-assembling peptides of the present invention were synthesized on a 0.1 mmol scale with standard fluorenylmethoxycarbonyl solid-phase techniques using a CEM Liberty automated microwave peptide synthesizer. MBHA rink amide resin (0.5 mmol/g substitution) was used to produce C-terminal amides; activation was performed with 0.5 M HOBt/HBTU in DMF. 47 and 49 were acetylated using 20% acethic anhydride solution in DMF. Peptides were then cleaved from the resin and deprotected with 9 ml of 95% trifluoroacetic acid (TFA), 2.5% water and 2.5% triisopropylsilane. The cleaved peptides were precipitated, washed several times with cold diethyl ether and dissolved in 20-25% of acetonitrile solution prior to be lyophilized and stored at −20° C. Crude peptides were analyzed and purified by reverse phase HPLC using a Waters system equipped with an analytical and semi-preparative BioBasic C4 (Thermo Scientific, UK). Eluents were 0.1% (v/v) TFA in water (Buffer A) and 0.1% (v/v) TFA in acetonitrile (Buffer B). Starting conditions were 10% buffer A and 90% buffer B and the gradient developed with a linear increase in buffer B. In 15 minutes gradient went to 65% buffer B. Identity of the peptides was confirmed with MALDI-TOF mass spectrometry. After purification, 0.1 M HCl exchange was performed at a volume of 1:1 in order to extract residual TFA. Then, peptides were lyophilized again. The peptides were successfully synthesized and purified (purity>95%).

Example 5

Atomic Force Microscope Imaging and Measurements

Self-assembling peptides according to the invention were dissolved in distilled water (GIBCO), at a concentration of 1% w/v one day prior imaging. The day after peptide solutions were diluted (in a ratio of 1:50), 2 ml of these solutions were placed on mica muscovite substrates and kept at room temperature for 2 minutes. The mica surfaces were then rinsed with distilled water to remove loosely bound peptides and solution was let to evaporate for 30 minutes. AFM images were collected in Tapping™ mode by a MultiMode Nanoscope IIIa (Digital Instruments) using single-beam silicon cantilever probes (Veeco RTESP: resonance frequency 300 KHz, nominal tip radius of curvature 10 nm, forces constant 40 N/m). Measured fiber dimensions were corrected because of the tip convolution. Being the observed tabular nanofiber heights (between 1 and 1.5 nm) far lower than the tip radius (10 nm) the observed widths were corrected with the formula 15:

$$\Delta x = \sqrt{2[h(2r_t - h)]}$$

Where Δx is the width broadening effect, h is the nanofiber height, and rt is for tip radius.

Results are presented as means±standard error of the mean.

Figure 2:
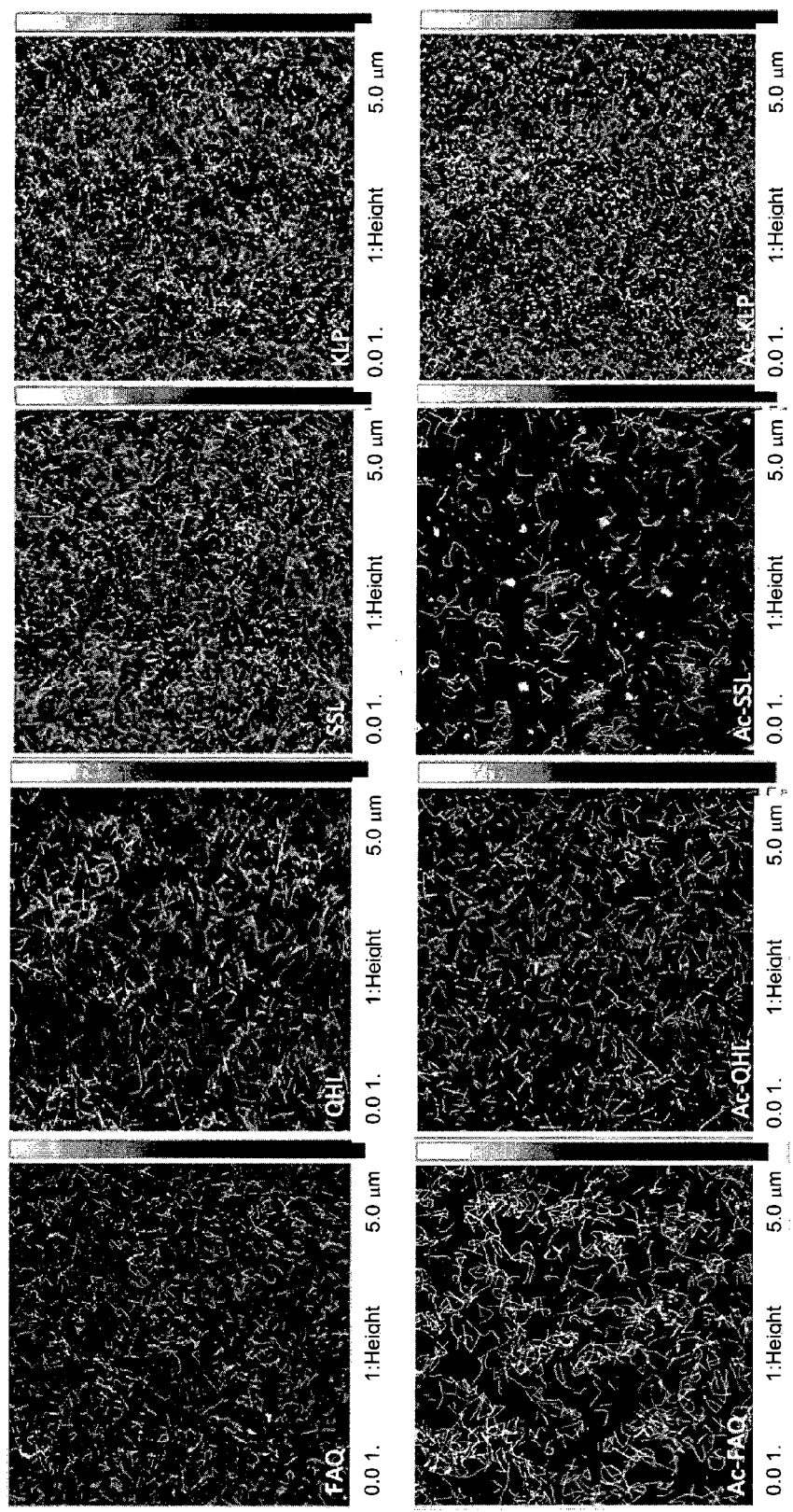
FIG. 2: shows atomic force microscopy (AFM) imaging of a selection of the tested SAPs as described in Example 5. All the synthesized peptides feature a tabular nanofiber morphology consistent with the hypothesis of an effective functionalization at the N-termini preserving the standard cross-β-sheet structure of LDLK12 peptide alone.

Atomic force microscope (AFM) measurements revealed that all peptides form tabular nanofibers (see FIG. 2). Deconvolved measurements are reported in Table 4. Processed data are consistent with the usual double layered anti-parallel β-sheet model described for these functionalized SAPeptides, giving, for these sequences, ~12 nm wide and ~1.6 nm high nanofibers.

The SAPs of the present invention self-assembled into similar nanofibers, a selection of these SAPs are shown in Table 5 below:

| SAPeptide | Height | Width |
|---|---|---|
| FAQ | 1.66 nm ± 0.12 nm | 13.4 nm ± 1.36 nm |
| Ac-FAQ | 1.52 nm ± 0.13 nm | 13.76 nm ± 1.12 nm |
| QHL | 1.77 nm ± 0.13 nm | 12.27 nm ± 1.17 nm |
| Ac-QHL | 1.7 nm ± 0.17 nm | 12.54 nm ± 1.35 nm |
| SSL | 1.57 nm ± 0.14 nm | 13.6 nm ± 1.58 nm |
| Ac-SSL | 1.74 nm ± 0.27 nm | 12.3 nm ± 1.53 nm |
| KLP | 1.70 nm ± 0.07 nm | 14.78 nm ± 0.67 nm |
| Ac-KLP | 1.76 nm ± 0.07 nm | 14.66 nm ± 0.55 nm |

Example 6

Rheology

Rheological properties of the self-assembling peptides of the invention were determined using a controlled stress TA Instruments AR-2000ex rheometer (TA Instruments). A cone-and-plate geometry (acrylic cone diameter, 20 mm; angle, 1°; truncation gap 34 μm) was used. Preliminary strain sweeps were performed for each sample to define the linear viscoelastic region, thus ensuring that moduli were independent of strain. Time sweeps, after addition of PBS (1×) were recorded at 25 C (angular frequency ω=1 Hz) and continued till G' plateaued. Frequency sweeps, both for peptide water solutions and for self-assembled scaffolds, were performed at 25 C with the instrument in oscillatory mode at controlled strain of 1%. Final strain sweeps was performed at 1 Hz oscillatory frequency and at 25 C: onset point of failure was calculated by linear interpolation and subsequent determination of the intersection of the G' modes within the linear region and at material failure respectively.

Figure 3A:
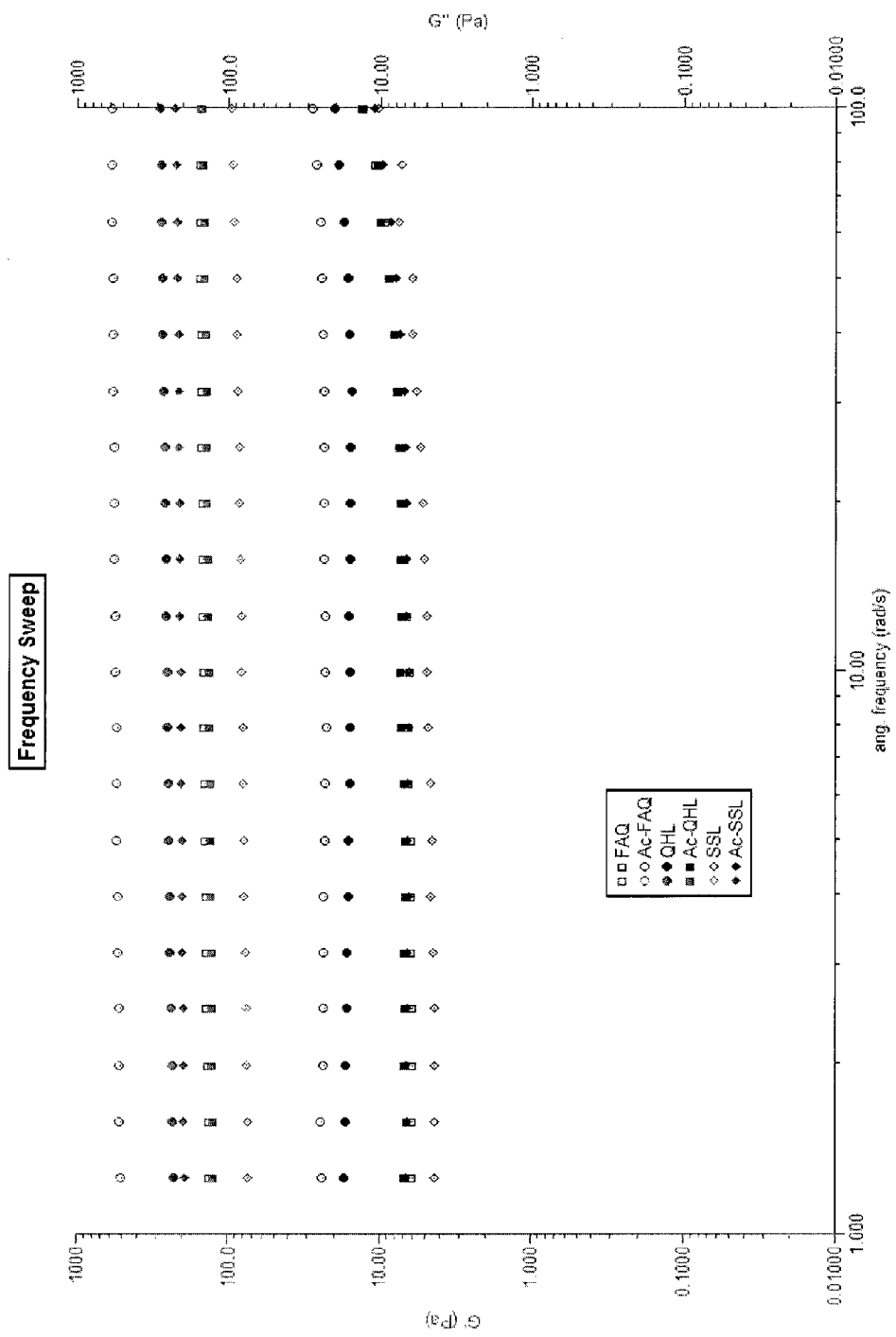
FIG. 3A: shows frequency sweep tests assessing the storage (G') and loss (G") moduli of a selection of the self-assembled hydrogels according to the present invention as described in Example 6.

The synthesized peptides self-assembled (at 1% w/v concentration solutions) (1×, pH 7.4) and formed solid scaffolds after addition of PBS. In the rheology tests (FIG. 3A) the storage modulus (G') was linear in the 1-100 Hz range (frequency sweep test), and well above the loss modulus (G"): a classic pattern seen in solid structures.

Linear values (in the 1-100 Hz range) of the assembled scaffolds reside in the 70-400 Pa and 8-20 Pa ranges respectively. These responses are typical of solid soft hydrogels.

Figure 3B:
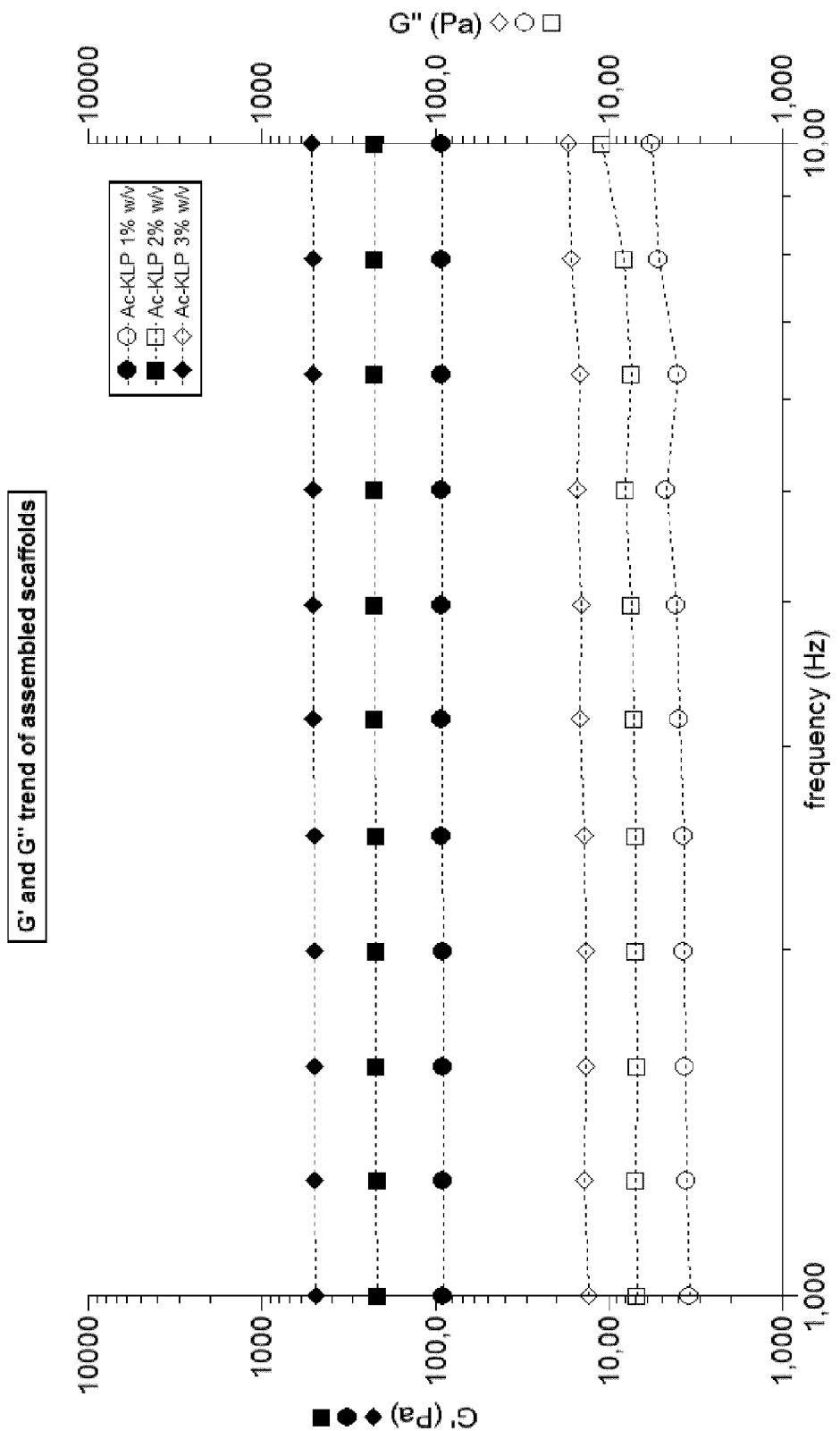
FIG. 3B: shows frequency sweep tests assessing the storage (G') and loss (G") moduli of a chosen SAP at different concentrations (1% w/v, 2% w/v, 3% w/v) as described in Example 6.

In particular, for peptide Ac-KLP, we assessed G' and G" values at different concentrations (i.e. 1% w/v, 2% w/v and 3% w/v) as depicted in FIG. 3B. G values (both G' and G") increased with concentration increments. This could be useful to obtain hydrogels with stiffnesses similar to those of the tissues to be regenerated or to favor neural differentiation of NSCs (favored in softer scaffolds).

Results:

The gelation results of a selection of the SAPs (dissolved at 1% w/v) according to the present invention is listed in Table 6:

| SAPeptide | G' pre-assembling | G' post-assembling | Onset point (% strain) |
|---|---|---|---|
| FAQ | 6.66 Pa | 142.7 Pa | 25.43% |
| Ac-FAQ | 5.11 Pa | 551.9 Pa | 22.75% |
| QHL | 4.53 Pa | 296.9 Pa | 28.58% |
| Ac-QHL | 2.68 Pa | 166.7 Pa | 10.16% |
| SSL | 9.01 Pa | 124.7 Pa | 17.78% |
| Ac-SSL | 6.72 Pa | 267.3 Pa | 26.12% |
| KLP | 3.30 Pa | 51.38 Pa | 56.46% |
| Ac-KLP | 2.88 Pa | 91.2 Pa | 47.82% |

Average values of the storage modull of SAPeptide solutions (G' pre-assembling), jellified scaffolds (G' post-assembling) and strain percentage at rupture (Onset point).

In Table 6 average G' values are reported (1-100 Hz range) before and after the addition of PBS. Onset points of rupture (strain sweep tests) are in the range of 10%-30% of strain. Thus the addition of the chosen functional motifs at the N-termini did not impair the capability of forming hydrogels of LDLK-12. Notably, all of the G' values are in the 100-1000 Pa range, reported as typical stiffness of nervous tissue, and favor neural differentiation of mesenchymal stem cells in vitro.

Example 7

Molecular Structure Characterization

Circular Dichroism (CD) Analysis

Far-UV CD spectra of each of the peptides of the present invention are recorded between 190 nm-260 nm at room temperature on an Aviv 62DS spectrometer. All measurements were carried out in 1-mm quartz cuvette in distilled water. Spectra are from accumulation of 3 scans. Blank spectra of the buffer without sample are subtracted. SAPeptide solutions were dissolved in water at 1% w/v and diluted at a final concentration of 0.2 mg/ml at one day after dissolution in water. Spectra are recorded in 2-nm steps, averaged over 4 seconds and normalized into Delta Epsilon units. Protein structures were deconvolved by using the CD Spectra Deconvolution Software 2.1 using 33 base spectra of known proteins.

Figure 4:
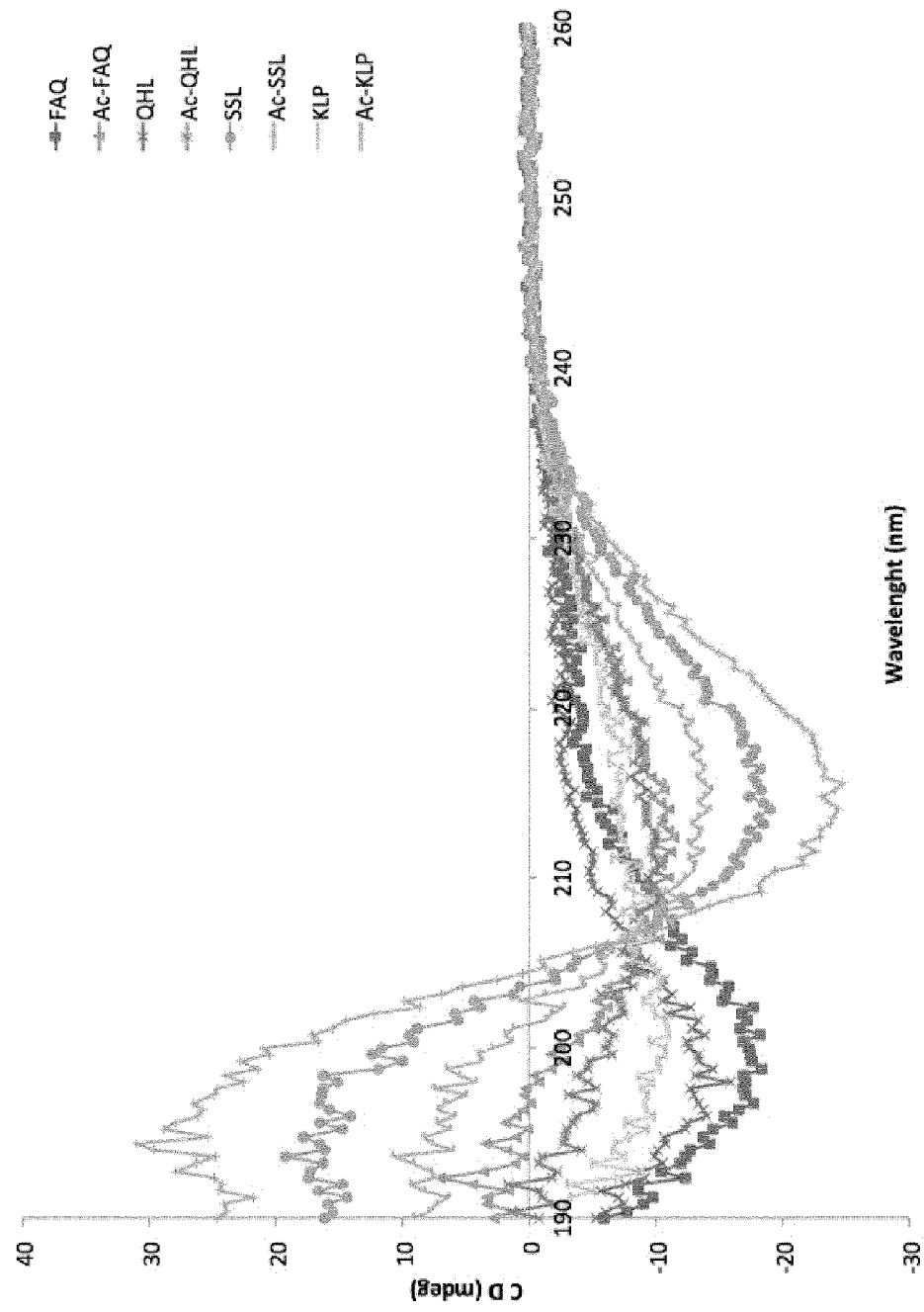
FIG. 4: Secondary structure characterization via Circular Dichroism of a selection of the SAPs as described in Example 7. Spectra have been averaged among three scans per each sample.

Results:

AFM findings, suggesting that all SAPeptides self-assemble mainly into β-sheets, are confirmed by CD spectra (FIG. 4): indeed a minimum value of 45% of β-sheets was detected in all SAPeptides after spectra deconvolution. Nonetheless, acetylated functional motifs showed spectra characterized by a higher percentage of (β-structures with respect to their unacetylated (and more charged) counterparts (FIG. 4), suggesting a tangible effect of the net charge at the free N-terminus over the stability of the assembled molecular structures (7)

Example 8

In Vitro Tests

Imaging and Cell Proliferation Assay

In vitro tests were performed as previously described (8), in order to assess whether the biomaterials (assembled hydrogels) obtained with the SAPs of the present invention influenced NSCs adhesion, survival and/or differentiation. SAPeptides (30 µl for each well at a concentration of 10 mg/ml) were assembled into 96 multiwells two hours before cell. Cells (at a concentration of $2\times10^4$ cells/cm$^2$) were seeded on the top-surface of each assembled scaffold. Initially, cells were cultured with basal medium supplemented with βFGF (10 ng/ml), added to enhance neuronal progeny differentiation. At 3 days in vitro (DIV), βFGF medium was replaced with Leukemia Inhibitory Factor (LIF, Chemicon) (20 ng/ml) and Brain Derived Neurotrophic Factor (BDNF, Peprotech) (20 ng/ml). Fresh medium was added every three days. For both viability and differentiation assays positive and negative controls consisted of Cultrex-BME® substrate (R&D systems) (1:100 dilution in basal medium) and untreated bottom well surfaces respectively. Cell viability was quantified via CellTiter 96® Aqueous Proliferation Assay (Promega) at 7 DIV as recommended in the Promega protocol. After calibrating the linear response between the cell number and absorbance values, proliferated cell populations were quantified (n=5) by using a Vmax microplate reader (Molecular Devices) at 490 nm wavelength. Values, reported as means±standard error of the mean, were blanked to their respective controls consisting of same substrates and cell culture media without cells.

Figure 5:
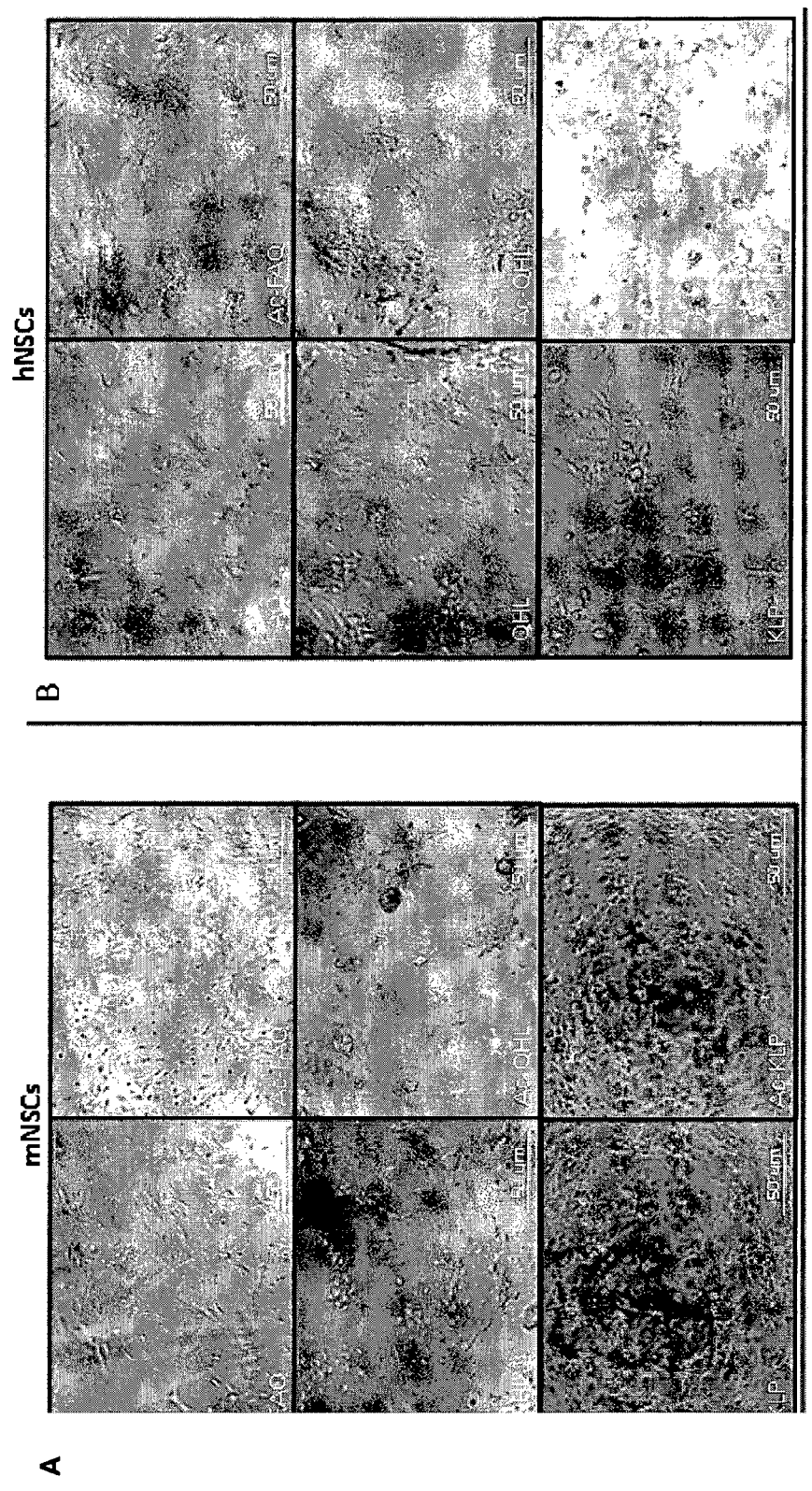
FIG. 5 (A) and FIG. 5 (B) respectively show the morphology of murine and of human NSCs; cultured over a selection of the synthesized SAPs 7 days in vitro (DIV), as described in Example 8.
Figure 5:
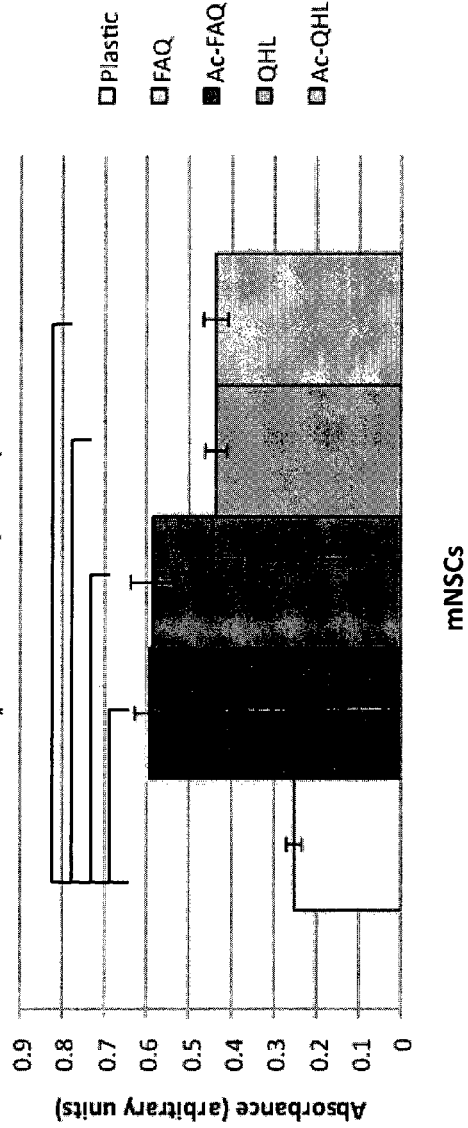
Figure 5:
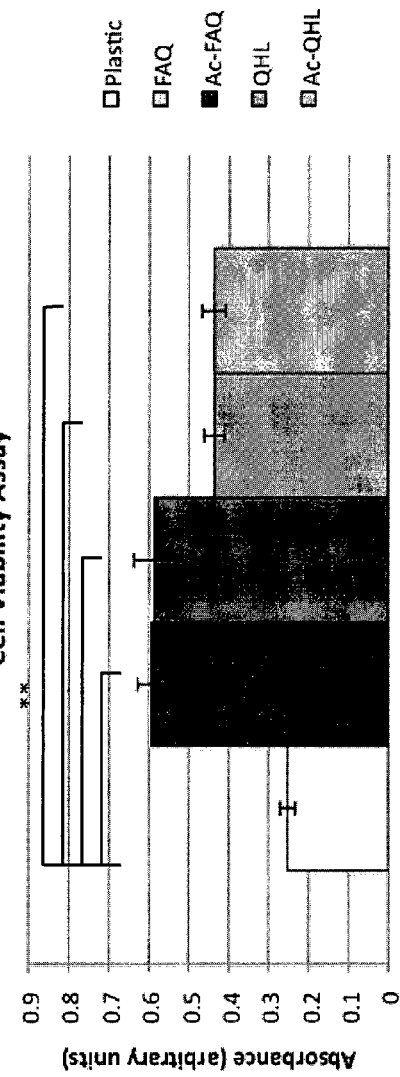

Results:

After 7 days in vitro (DIV) both mouse NSCs and human NSCs progenies cultured over assembled hydrogels of FAQ and Ac-FAQ showed spread and branched cells, evenly covering the scaffolds top surfaces (FIGS. 5A and B). No appreciable differences in cell spreading or branching were seen among the acetylated and not-acetylated peptide counterparts. Murine and human NSCs gave similar results. Wide spreading was detected for FAQ. FAQ and QHL, both acetylated and not, significantly fostered cell viability with respect to control (* $P<0.005$ for murine NSCs, ** $P<0.03$ for human NSCs; t-student paired test: n=5).

MTS cell viability assays (FIGS. 5C and D) confirmed the qualitative morphological observations: mouse and human NSCs showed comparable results, i.e. cell population was bigger for FAQ and Ac-FAQ, followed by QHL and Ac-QHL. No significant difference was detected between Acetylated and not Acetylated counterparts, while FAQ and QHL significantly favored both murine and human NSCs cell viability in respect to control. FAQ and QHL showed to be functionalized SAPs effective in obtaining NSC survival and proliferation. KLP functionalized SAP (both Acetylated and not Acetylated) formed solid hydrogels and fostered NSCs adhesion and spreading similarly to FAQ.

Immunofluorescence

Immunofluorescence tests were performed for assaying the phenotypes of the differentiated human and murine NSC progenies. In the case of KLP and Ac-KLP just murine NSC have been used. Ac-KLP and KLP scaffolds were prepared at different concentrations in order to display three different stiffness values (viz. 100, 500 and 1000 Pa). This was done to assess the influence of scaffold concentration (and consequently its stiffness) over NSC differentiation. All the other peptides were tested at 1% v/w concentration instead. The following antibodies were used: rabbit polyclonal against GFAP (1:500, DakoCytomation) for astrocytes, mouse monoclonal against βIII-Tubulin (1:500, Covance) for neurons, mouse monoclonal against GalC (1:200, Chemicon) and O4 (1:200, Chemicon) for oligodendrocyes. Secondary Abs were Goat anti Mouse Alexa 488 (1:1000, Molecular Probes), Goat anti Mouse Cy3 (1:1000, Jackson Immunoresearch), Goat anti Rabbit Cy3 (1:1000, Jackson Immunoresearch). Cell nuclei were counterstained with DAPI (Molecular Probes). Quantitative analyses were performed by counting 100-300 cells for each of 9 randomly chosen fields over a total of 3 independent experiments. Phase contrast and fluorescence images of the adhering cells were acquired via Zeiss microscopes Axioplan 2 and ApoTome System at one week after seeding.

Figure 6A:
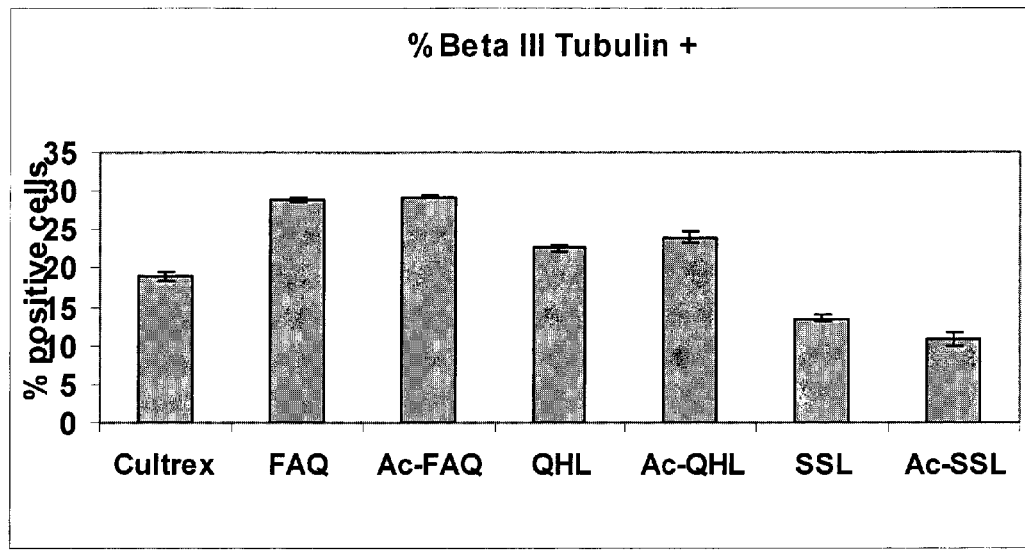
FIG. 6: Neural differentiation of murine (A,D) and human neural stem cells (E,H). The quantification of neurons (murine in A; human in E), astrocytes (murine in B; human in F) and oligodendrocytes (murine in C; human in G) is shown; the statistical significances are shown in a table next to each graph, as described in Example 8.
Figure 6B:
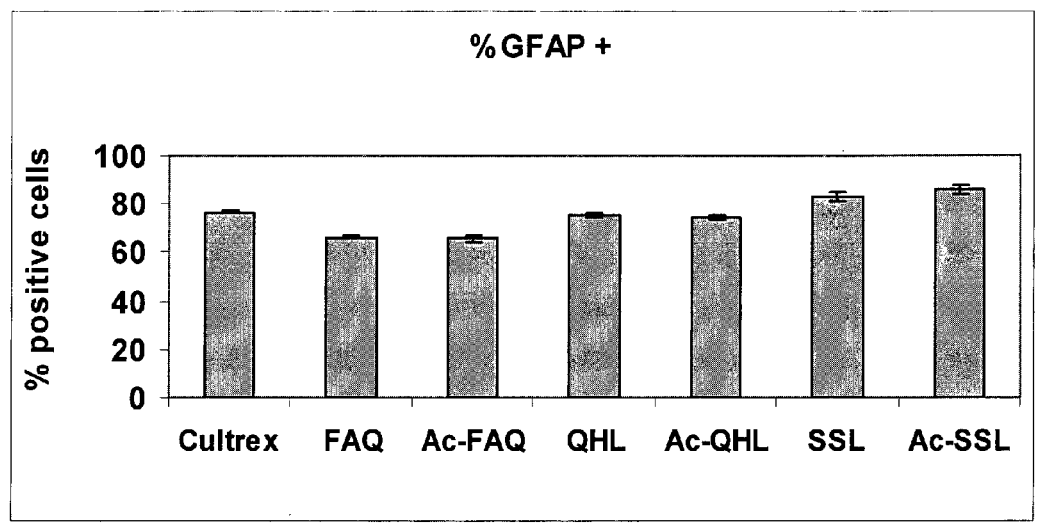
Figure 6C:
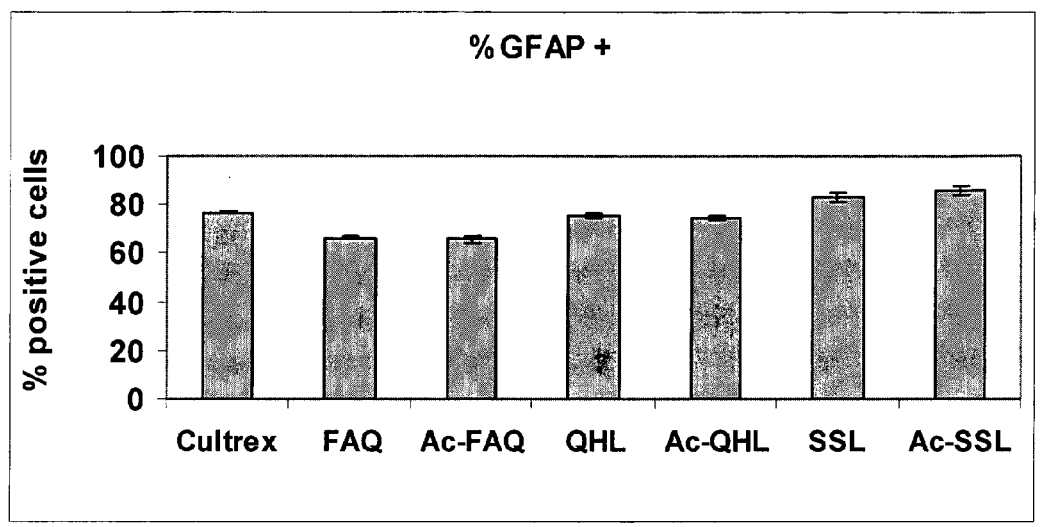
Figure 6:
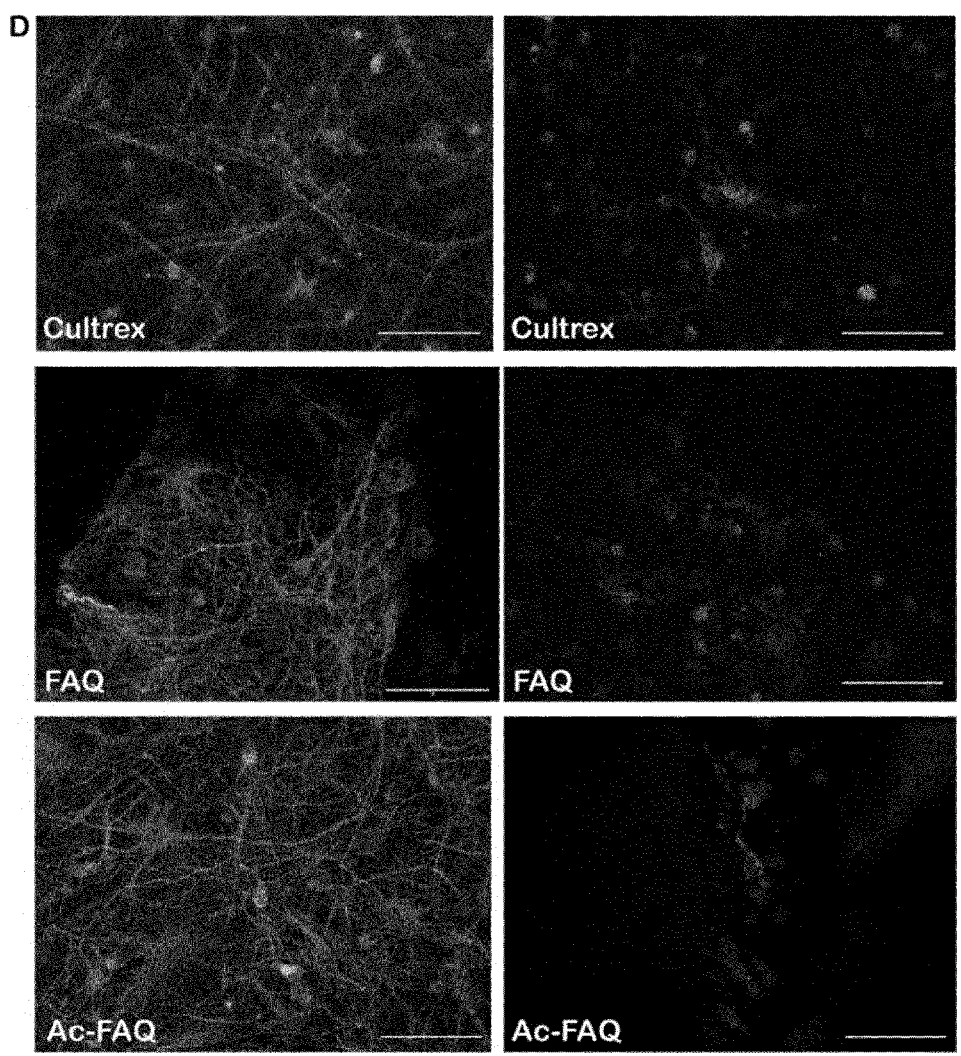
Figure 6E:
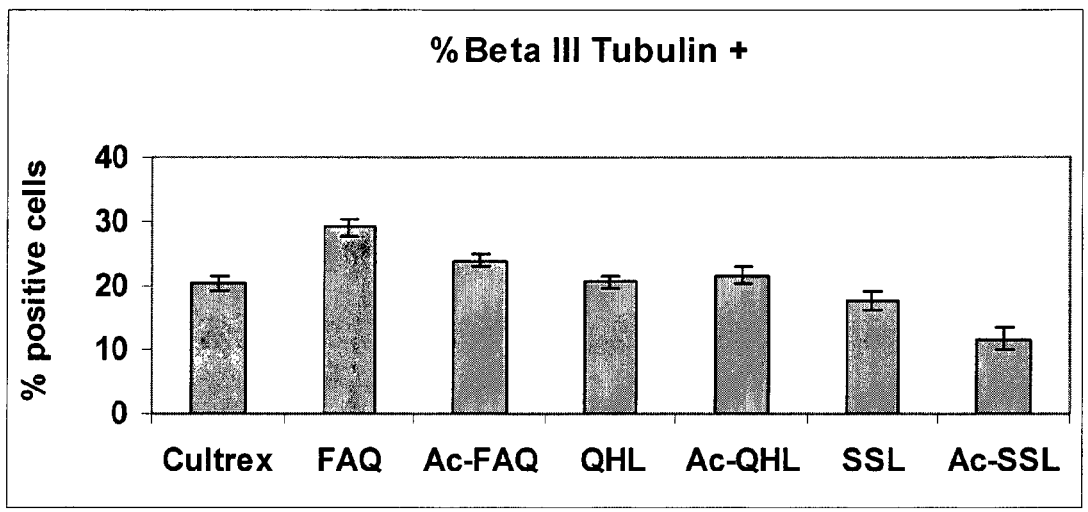
Figure 6F:
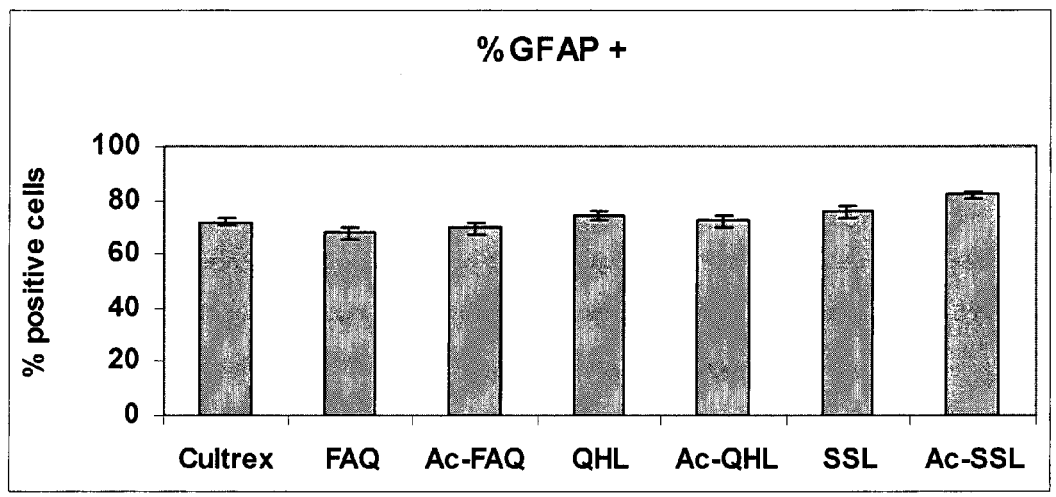
Figure 6G:
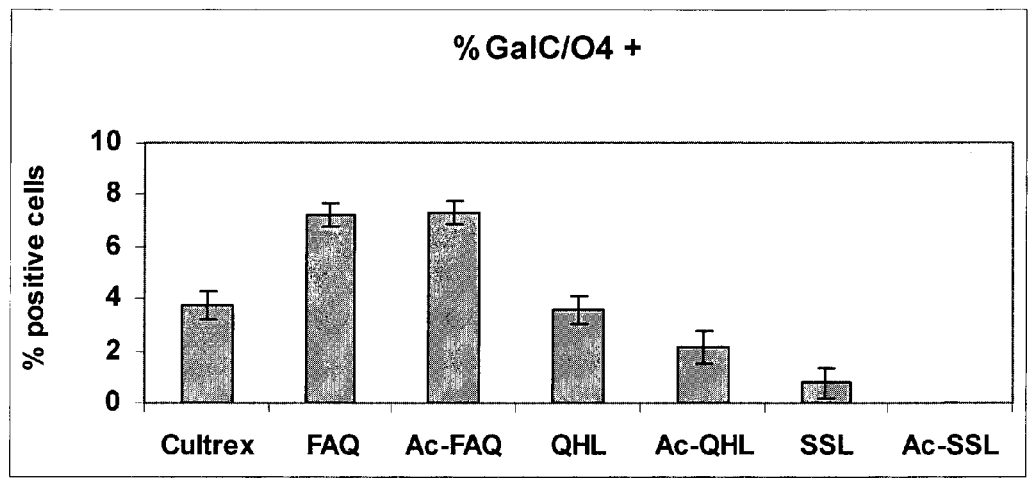
Figure 6:
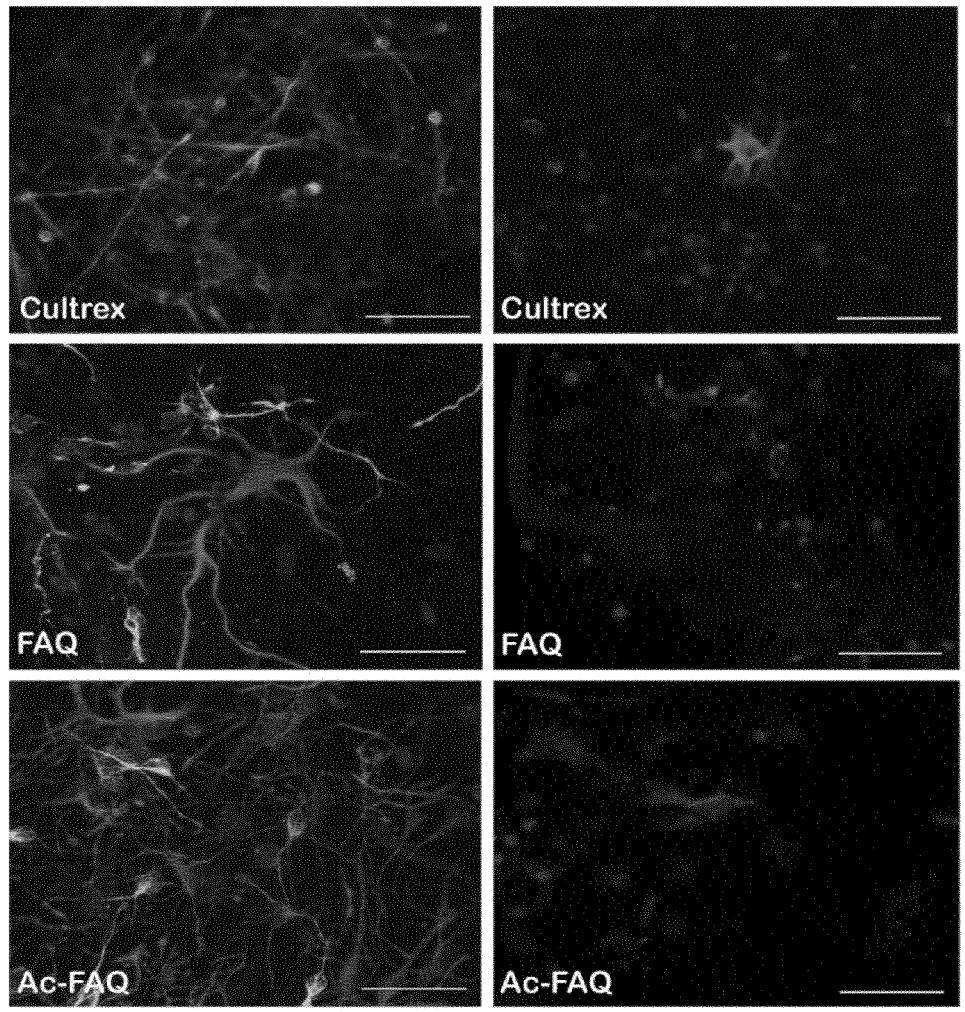

Results:

Differentiation of both murine and human NSCs, showed similar results (FIG. 6)

NSCs cultured on bare plastic wells did not show an appreciable branching, neither an efficacious differentiation thus the clustered NSC progeny could not be reliably quantified in terms of differentiated phenotypes.

The results show that the SAPs according to the present invention allow NSC differentiation into neurons, astrocytes and oligodendrocytes. The number of neurons and oligodendrocytes obtained by differentiating the cells on FAQ or Ac-FAQ were significantly higher even when compared to the progenies obtained on Cultrex (FIG. 6A-6C-6E-6G), a positive control.

Oligodendrocytes were detected in the shape of discrete clusters of GalC/O4 positive cells on Cultrex, FAQ and Ac-FAQ (FIG. 6D-6H).

These results show that both FAQ and Ac-FAQ efficiently support human and murine NSCs proliferation.

βIIITubulin positive neurons (murine, left column of D; human, left column of H), GFAP positive astrocytes (murine, left column of D; human, left column of H) and GalC/O4 double positive oligodendrocytes (murine, right column of D; human, right column of H) are detected in both the tested materials. Nuclei are visualized with DAPI. Scale bars=50 µm.

Figure 7A:
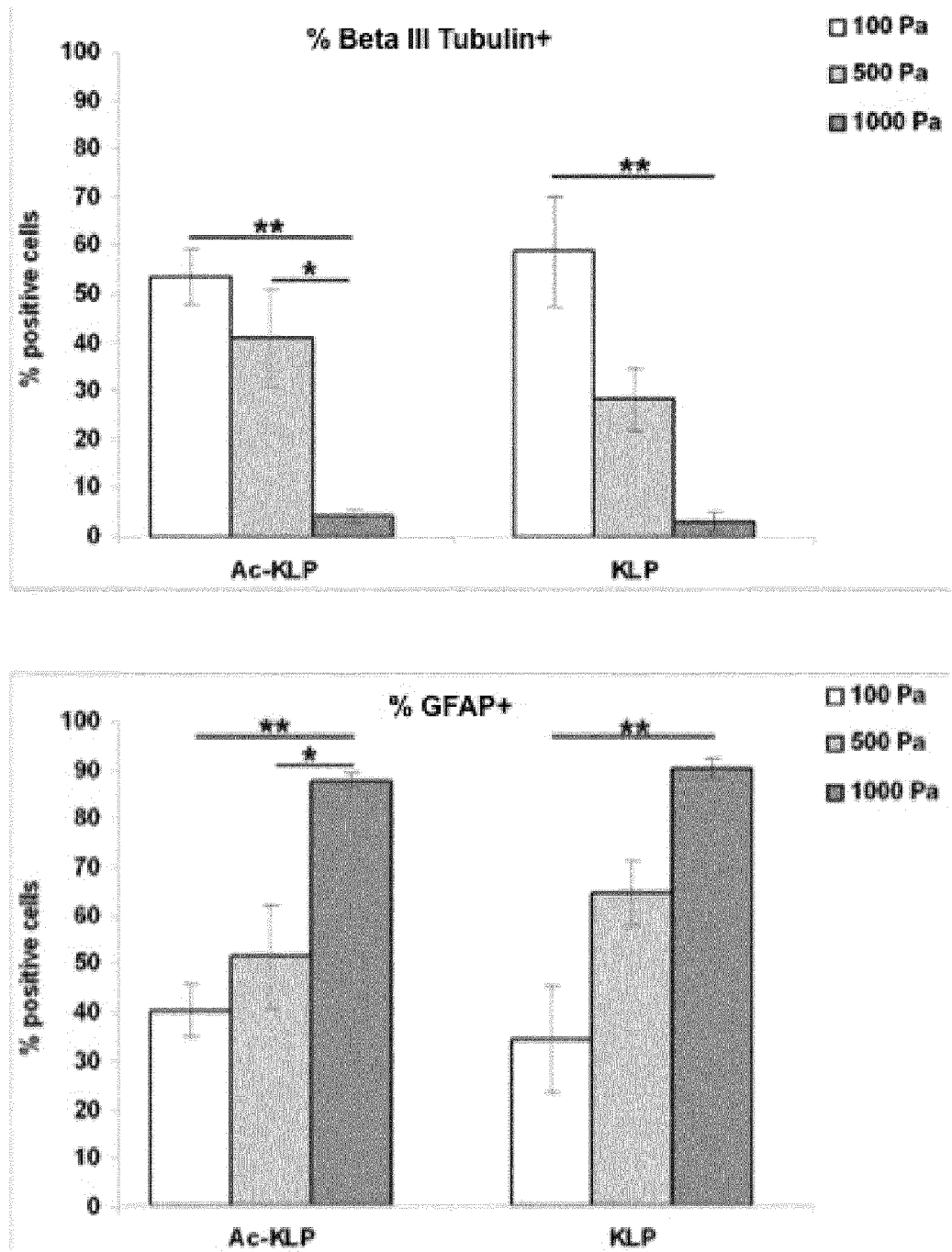
FIG. 7: Neural differentiation of murine NSCs over Ac-FAQ self-assembled scaffolds featuring the following stiffnesses: 100 Pa, 500 Pa and 1000 Pa. Neuronal and astroglial populations have been quantified and depicted in FIG. 7 (A) and in FIG. 7 (B) respectively as described in Example 8.
Figure 7B:
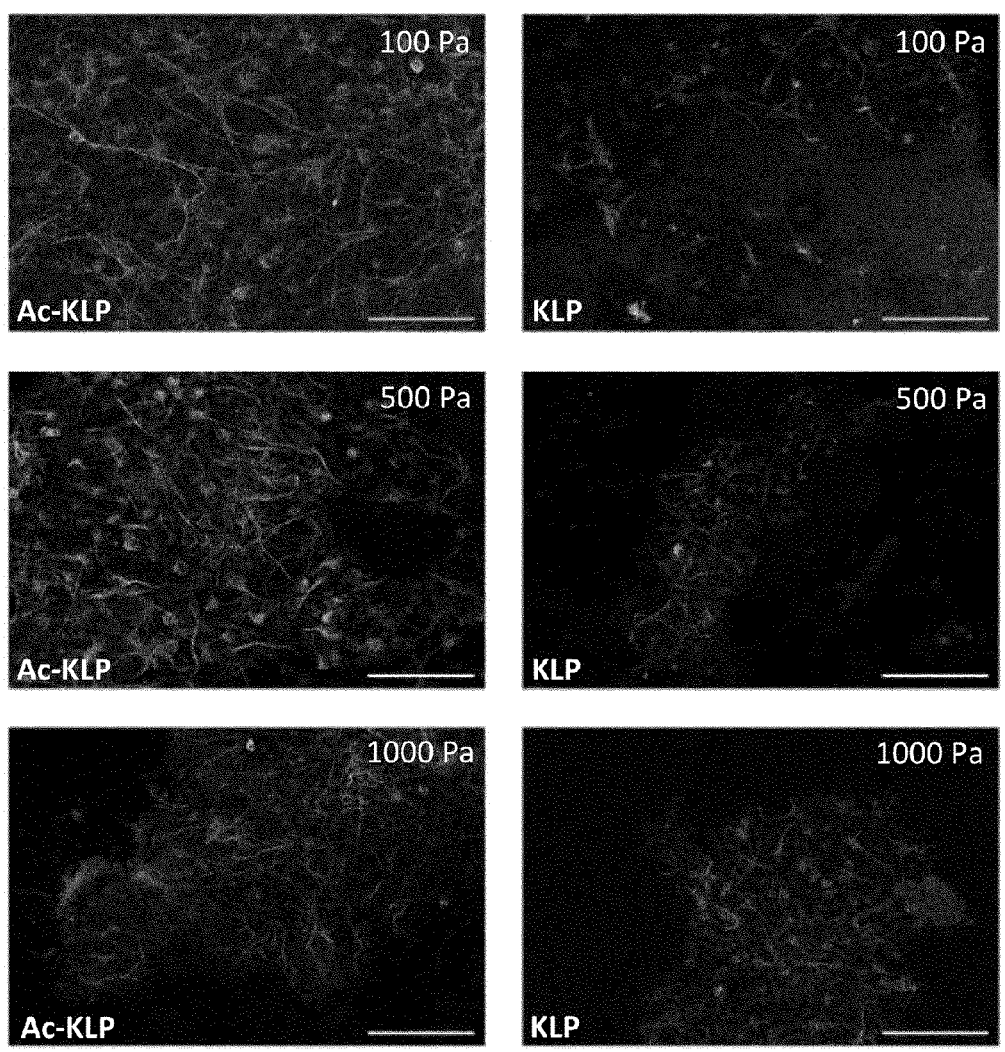

For both KLP and Ac-KLP the tested different concentrations showed significant increments of differentiated neurons (βIIITubulin positive cells) in correspondence of stiffness reductions (FIG. 7A): this was counterbalanced by increments in the percentage of astrocytes (GFAP positive cells). (*=$P<0.05$**=$P<0.01$). No significant difference was detected between KLP and Ac-KLP at similar scaffold stiffnesses. Remarkably, percentages of neurons above 50% are the best results achieved among all the tested functionalized scaffolds. For softer scaffolds, neuronal and astroglial morphologies were highly branched and spread all over the scaffolds (FIG. 7B).

Example 9

In Vivo Regeneration of Spinal Cord Injuries

Surgery

The results of the neuroregenerative potential of Ac-FAQ SAPeptides in an in vivo model of acute contusive spinal cord injury (SCI) are described below.

All procedures involving animals were performed according to EC guidelines (EC Council Directive 86/609, 1987)

The results of the neuroregenerative potential of Ac-FAQ SAPeptides in an in vivo model of acute contusive spinal cord injury (SCI) are described herein.

Figure 8:
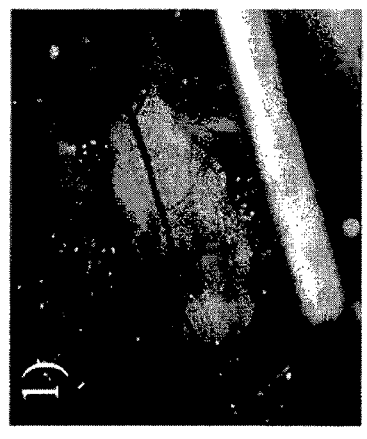
FIG. 8(A) Delivery of the biomaterial: spinal cord was exposed at T9-T10 level, then immediately after injury (A1) animals were injected with Ac-FAQ or the vehicle alone using an Hamilton syringe (A2) as described in Example 7.
FIG. 8(B) hindlimb locomotor recovery was evaluated in Ac-FAQ treated rats and controls using the 21-points BBB scale as described in Example 9. After 6th week animals treated with Ac-FAQ showed displayed a significantly improved locomotor recovery in than in controls.
FIG. 8(C) Measurement of lesion size in saline-injected (C1) and Ac-FAQ-treated (C2) rats was performed on longitudinal sections stained with hematoxylin/eosin as described in Example 10. Scale bar=800 μm.
FIG. 8(D) Measurement of GAP43 positive fibers in saline-injected (D1) and Ac-FAQ-treated (D2) rats was performed on longitudinal sections after immunofluorescence staining as described in Example 10. Scale bar: (D1) and (D2)=400 μm, (D3)=200 μm. Nuclei were counterstained with DAPI.
FIG. 8(E) Macrophage infiltration in saline-injected (1) and Ac-FAQ-treated (2) rats on immunostained longitudinal sections as described in Example 8. Scale bar: (1) and (2)=400 μm, (3)=100 μm. Nuclei were counterstained with DAPI. Values represent means±SEM. Significance symbols: * $p<0.05$, ** $p<0.005$. Arrows indicate the putative presence of the injected SAPs into the cyst.
Figure 8:
Figure 8:
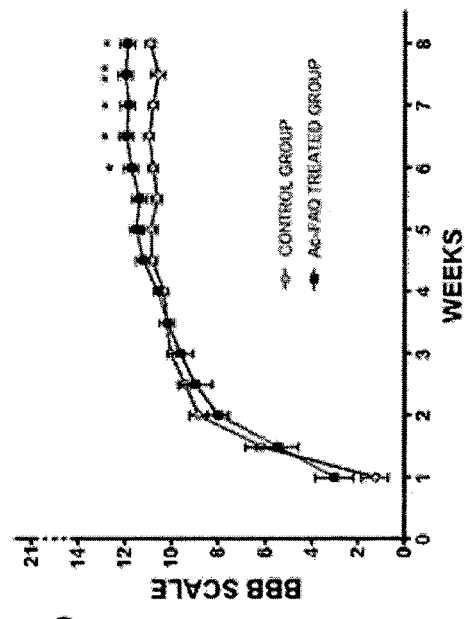
Figure 8:
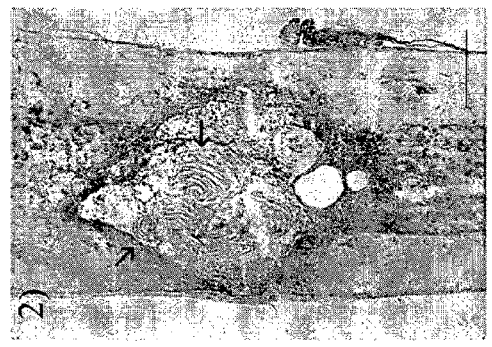
Figure 8:
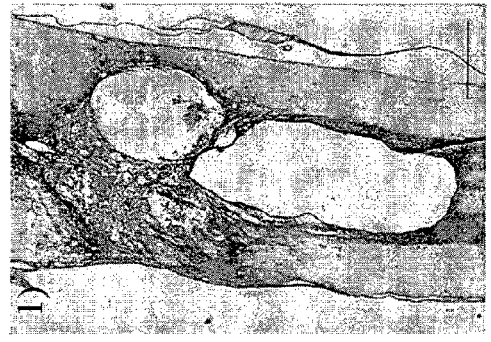
Figure 8:
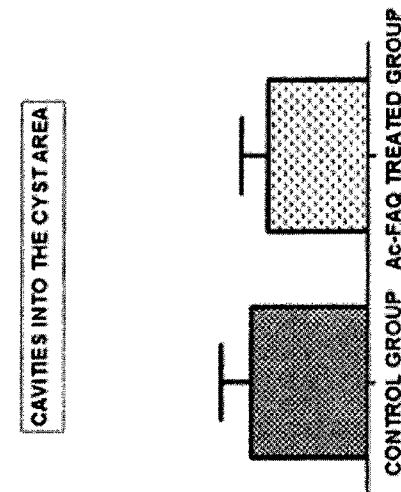
Figure 8:
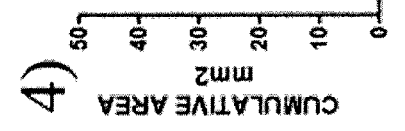
Figure 8:
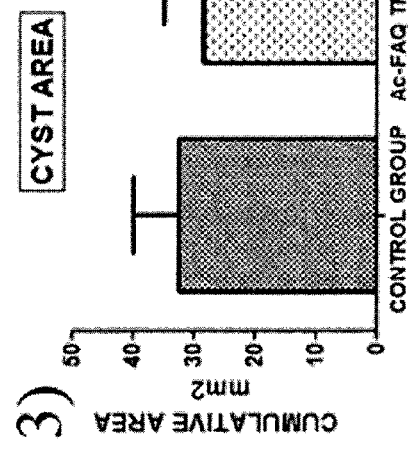
Figure 8:
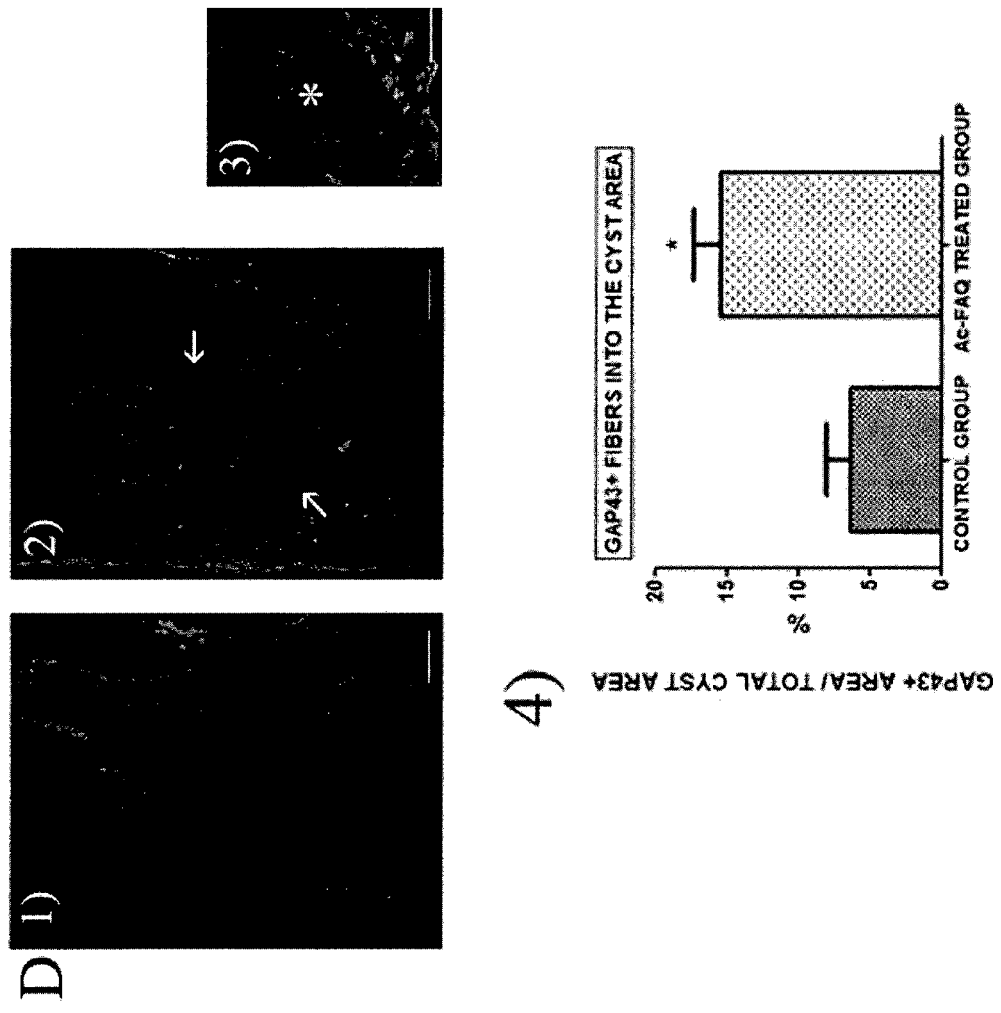
Figure 8:
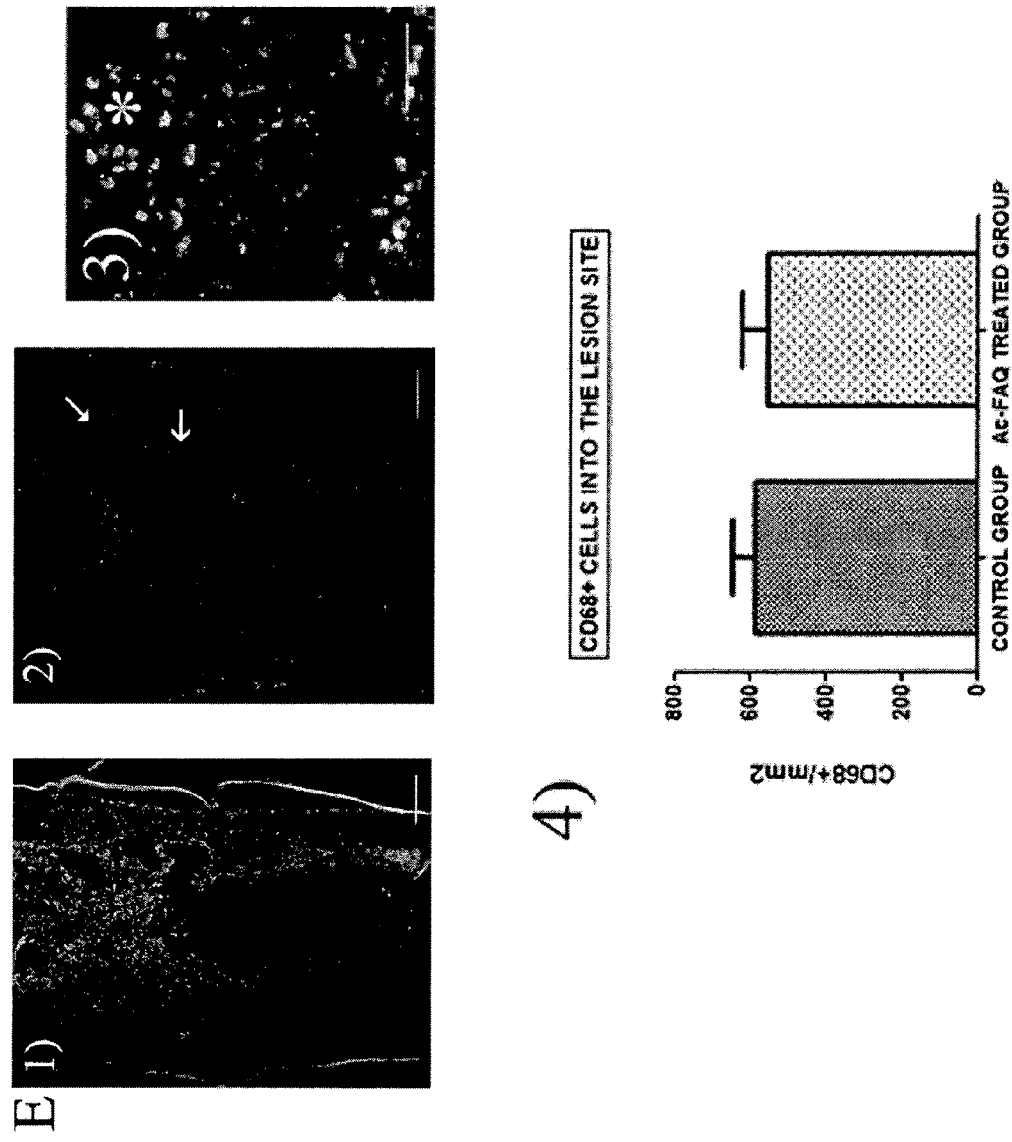

20 female Sprague-Dawley rats weighting 200-250 gr (Charles River Laboratories) were randomly divided into two groups: 1) spinal cord injured animals treated with Ac-FAQ and 2) spinal cord injured animals treated with the saline solution (control group). Rats were anesthetized with an intraperitoneal injection of ketamine (80 mg/kg) and xylazine (10 mg/kg). After laminectomy at the T9-T10 level, the exposed spinal cord was lesioned (FIG. 8A1) by a 10-gram rod dropped from a height of 25 mm by using a MASCIS Impactor device (WM Keck Center for Collaborative Neuroscience, Rutgers University), as previously described 33. Immediately after injury, animals were injected with Ac-FAQ (1% acqueous solution) or the saline solution using an Hamilton syringe held via a micromanipulator (FIG. 8A2). The biomaterial or the distilled water was delivered into the lesion site at distances of 500 µm, and at each interval two injections of 0.5 µl each were made, for a total dose of 3 µl. After injection, the muscles were sutured and the skin was closed with wound clips. Rats were treated daily for one week with analgesic (carprofen, 5 mg/kg) and antibiotic (enrofloxacin, 5 mg/kg). Bladder was manually expressed until recovery of the bladder reflex.

Behavioural Test

Hindlimb recovery was assessed by using the Basso, Beattie, Bresnahan (BBB) Locomotor Rating Scale. Starting from 1 week post-injury, every 3-4 days each rat was observed and recorded with a digital video camera for 4 min in an open field. Rats were evaluated in double-blind experimental settings. Ac-FAQ treated animals showed a gradual recovery and a significant improvement ($p<0.05$) of hindlimb motor recovery in comparison to controls (FIG. 8B) at week 6, 7 and 8 weeks after injury (11.95±0.30): showing a frequent or consistent plantar stepping with occasional forelimbs-hindlimbs coordination. BBB score of the vehicle-treated animals plateaued at week 5 (10.92±0.27). Control group's BBB scores are consistent with the fact that injections did not further impair the locomotor functions of the injured animals. Ac-FAQ treated animals showed improvement of both hindlimbs motor function and coordination and a better recovery of plantar stepping and coordination in comparison to controls.

Example 10

In Vivo Regeneration of Spinal Cord Injuries

Histology and Morphometrical Quantification 8 weeks after injury animals were sacrificed by transcardial perfusion with 4% paraformaldehyde. At this time the lesion site is occupied by a cyst, that can be spanned by strands of connective tissue (trabeculae) occasionally containing axon sprouts. Spinal cords were removed, embedded in OCT, frozen and sliced into 16 µm thick longitudinal sections.

For histochemical analysis, slices were stained with hematoxylin/eosin. For immunofluorescence analysis, slices were washed with PBS, permeabilized with 0.1% Triton X-100 and treated with 10% normal goat serum.

Quantitative analysis was performed on longitudinal sections of rat spinal cords, spanning between T7 and T12 and including the injury site (T9-T10). Average cumulative cyst area in Ac-FAQ-treated animals (28.30±6.70 mm$^2$) was similar to that one of controls (32.30±7.69 mm$^2$), suggesting that injection of the Ac-FAQ did not significantly affect cyst formation. Hence, in order to assess if the biomaterial injection could favour the projection of trabeculae into the cyst and contribute to bypass the scar, we measured only cavities into the cyst excluding trabeculae. However, measurements of the cavities size within the cyst, obtained by excluding strands of trabeculae did not show any significant difference between Ac-FAQ and control groups (16.77±4.50 mm$^2$ and 19.46±4.97 mm$^2$, respectively) (FIG. 8C).

The presence of axons expressing Gap-43 and βIII within the cyst was investigated. Gap-43 positive fibers were quantified and the relative value of GAP-43 immunopositive area was expressed as percentage of the total cyst area.

The presence of higher levels of GAP-43 in the lesion site of SAP-injected in comparison to saline-injected animals suggests that SAP provides microenvironments promoting neurite outgrowth mediated by GAP-43 and allows supplementary axonal sprouting, thus fostering nervous regeneration. The average immunopositivity for GAP-43 was significantly higher in animals treated with SAPs (15.46±1.94% of the whole cyst area) than in controls (6.33±1.70% of the whole cyst area) (FIG. 8D). FIG. 5D2-5D3 show SAP-treated animals where we observed several GAP43 positive fibers (white arrows) infiltrating the cyst (D3, high magnification of D2; *=cyst) while FIG. 8D1 depict the cyst of a saline-injected animal. The relative value of GAP-43 positive area, expressed as percentage of the total cyst area, was significantly higher in SAP-treated than in vehicle-injected animals (D4): $p<0.05$. Scale bar: (D1) and (D2)=400 µm, (D3)=200 µm. Nuclei were counterstained with DAPI.

Injured tissue was quantified in seven-to-sixteen longitudinal sections per animal, depending on the cyst extent. Sections started from the dorsal surface of the spinal cord and were spaced 160 µm. Sections were stained with hematoxylin/eosin and images were captured (Axioplan2 Zeiss microscope) at 5× magnification, then single images were merged, converted into binary pictures and cavities into the injured area were quantified via Image J software (http://rsb.info.nih.gov/ij/). We measured also the whole injured tissue size. Pixel area was converted to mm$^2$ and measurements either of the injured tissue or of the cavities inside it were added to produce the cumulative area of each animal as relative measure of the lesion size.

Macrophage infiltration, into the lesion site, was quantified in three longitudinal sections, spaced 160 µm, per animal. Images (20× magnification) were captured of immunostained tissues with CD68 (1:500, Serotec) and an Alexa 488-conjugated antibodies (1:500, Invitrogen). A total area of 2.3 mm$^2$ was quantified per each section (approximately 16 images). Cells count of CD68 positive cells was made with Image J. The number of macrophages/mm$^2$ was averaged over three measurements on different sections per each animal (FIG. 8E).

Axon regeneration/sprouting, into the cyst area, was quantified on six longitudinal sections (spaced 160 µm) per animal via GAP-43 (1:200, Millipore) and Cy3-conjugated antibodies (1:1000, Jackson). For each section we took serial images (10× magnification) of the injured site. Again, images were merged, converted to binary pictures and the content of positive pixels was measured in order to quantify the GAP-43 positive area into the injured site. The mean of the six measurements, expressed as percentage of the total cyst area, constituted the value of the axonal regeneration/sprouting of each animal.

Figure 9:
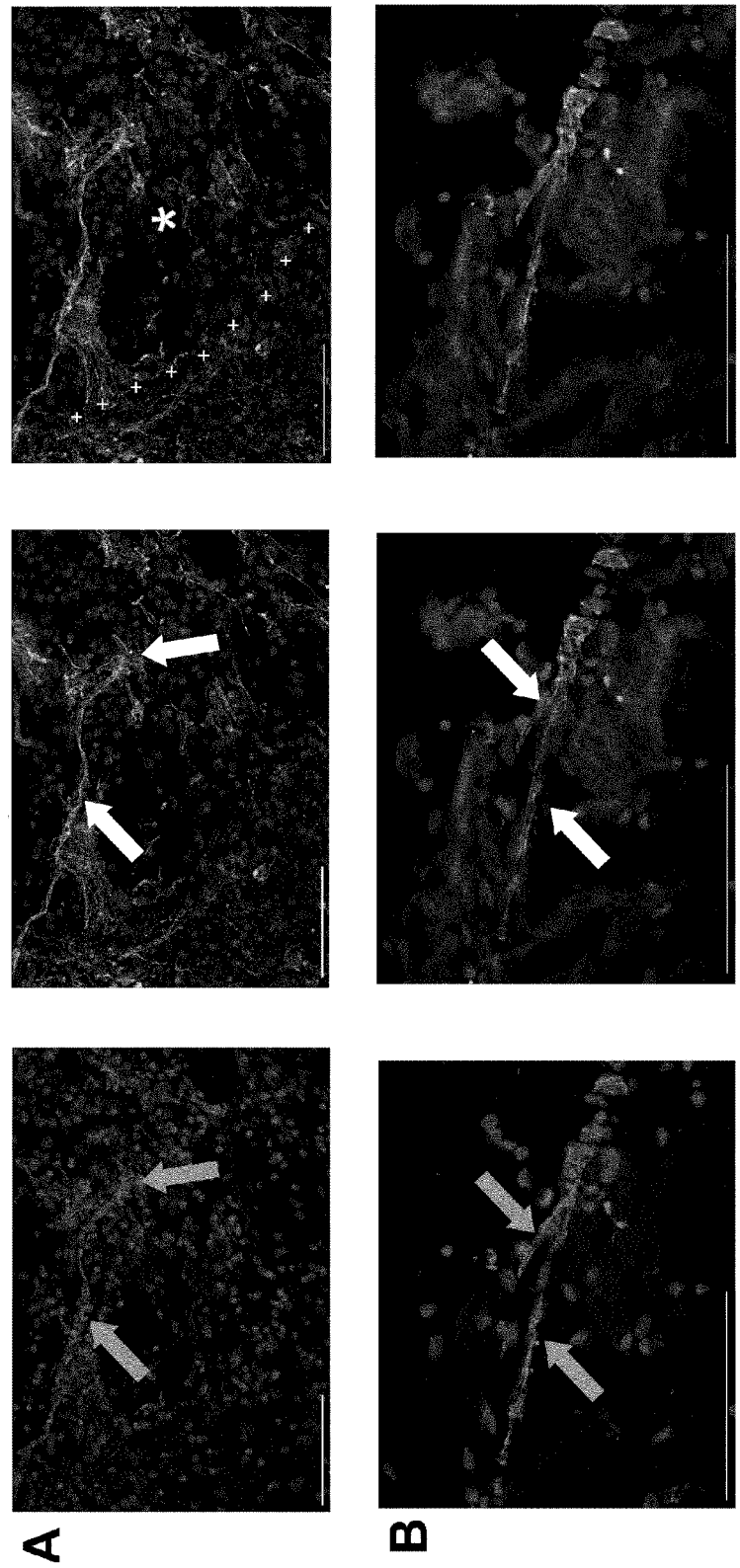
FIG. 9(A) Evaluation of the presence of GAP-43 and βIII positive fibers into the lesion site of Ac-FAQ-treated animals as described in Example 10. Immunofluorescence for GAP-43 (gray arrows) and βIII (white arrows) showed that all GAP-43 positive fibers also expressed βIII (merge image). Most of the GAP-43+ fibers were detected into the cyst (*=cyst) or close to the cyst borders (marked with '+'). Nuclei were counterstained with DAPI.
FIG. 9(B) Fibers infiltrating the Ac-FAQ found into the site of injection were positive for both GAP-43 (gray arrows) and βIII Tubulin (white arrows). Nuclei were counterstained with DAPI. Scale bars: =100 μm.

In Ac-FAQ-treated animals we detected several fibers invading both the cyst cavity and trabeculae, whereas in saline-injected animals the majority of fibers was only observed into trabeculae, indicating that the biomaterial could also constitute a trophic support for growing axons. All GAP-43 positive fibers also expressed βIII (FIG. 9A). Gap-43 is a phosphoprotein that is known to play an important role in neural development, axonal regeneration, and modulation of synaptic function.

To stain proteoglycans and glycosaminoglycans into the lesion site we used toluidine blue O solution (Sigma), while Collagen content was evaluated using trichrome Heidenhein modified method kit (Bio-Optica). Other primary antibodies comprise anti-laminin (1:200, Sigma), anti-lba1 (1:1000, Wako) for microglia and anti-GFAP (1:500, Millipore) for astrocytes.

Further histological analyses were performed and it could be seen that several cells and nerve fibers infiltrated the SAP scaffolds. These cells were positive for Iba1, a marker for microglia, for βIII Tubulin, a marker for neurons, and GFAP (glial fibrillary acidic protein), a marker for astrocytes. Infiltrating nerve fibers were positive for both GAP-43 and βIII Tubulin (FIG. 9B).

Taken together, data from histology suggest that Ac-FAQ could promote a further axonal sprouting/regeneration in comparison to the limited axon outgrowth normally occurring after incomplete SCI. This finding is in accordance with the improvement of locomotor recovery that we observed in biomaterial-treated animals.

Statistical Analysis

Data were processed using GraphPadPrism 5 software. Values are reported as means±standard error of the mean (SEM). Results of NSC proliferation assays and mNSC differentiation in the presence of the soluble KLPGWSG peptide were assessed for their statistical significance via paired t-tests: results were compared to negative control. Statistical significance of scaffold-based differentiation tests was assessed using the one-way ANOVA analysis followed by Tukey's comparison test. In all tests p values<0.05 were considered as statistically significant.

BBB score significance test between control and treated animal groups was performed by unpaired t-test. For quantification of the cavity size, macrophage infiltration and GAP43 positive fibers, groups comparison was made by Mann-Whitney test. All analyses were two-tailed and p values<0.05 were considered as statistically significant.

From the above description and the above-noted examples, the advantage attained by the product described and obtained according to the present invention are apparent.

REFERENCES

1. Polak, J. M.; Bishop, A. E., Stem Cells and Tissue Engineering: Past, Present, and Future. Ann N Y Acad Sci 2006, 1068, 352-66.
2. Weiss, S.; Reynolds, B. A.; Vescovi, A. L.; Morshead, C.; Craig, C. G.; van der Kooy, D., Is There a Neural Stem Cell in the Mammalian Forebrain? Trends Neurosci 1996, 19, 387-93.
3. Kang, H. C.; Kim, D. S.; Kim, J. Y.; Kim, H. S.; Lim, B. Y.; Kim, H. D.; Lee, J. S.; Eun, B. L.; Kim, D. W., Behavioral Improvement after Transplantation of Neural Precursors Derived from Embryonic Stem Cells into the Globally Ischemic Brain of Adolescent Rats. Brain Dev 2009.
4. Zhang, P.; Li, J.; Liu, Y.; Chen, X.; Kang, Q.; Zhao, J.; Li, W., Human Neural Stem Cell Transplantation Attenuates Apoptosis and Improves Neurological Functions after Cerebral Ischemia in Rats. Acta Anaesthesiol Scand 2009, 53, 1184-91.
5. Pluchino, S.; Quattrini, A.; Brambilla, E.; Gritti, A.; Salani, G.; Dina, G.; Galli, R.; Del Carro, U.; Amadio, S.; Bergami, A., et al., Injection of Adult Neurospheres Induces Recovery in a Chronic Model of Multiple Sclerosis. Nature 2003, 422, 688-94.
6. Vescovi, A. L.; Reynolds, B. A.; Fraser, D. D.; Weiss, S., Bfgf Regulates the Proliferative Fate of Unipotent (Neuronal) and Bipotent (Neuronal/Astroglial.
7. Taraballi, F; Campione M, Vescovi A L, Sassella A, Paleari A, Whang W, Gelain F Effect of Functionalization on the Self-Assembling Propensity of β-Sheet Forming Peptides. Soft Matter 5: 660-668.
8. Gelain, F.; Bottai, D.; Vescovi, A.; Zhang, S., Designer Self-Assembling Peptide Nanofiber Scaffolds for Adult Mouse Neural Stem Cell 3-Dimensional Cultures. PLoS ONE 2006, 1, e119.

The invention claimed is:

1. A self-assembling peptide (SAP) comprising:
   (i) a heptapeptide domain comprising the amino acid sequence of
   -KLPGWSG- SEQ ID NO: 10;
   (ii) a spacer region comprising one to seven glycine amino acid units; and
   (iii) a backbone region comprising at least one amino acid repetition unit selected from the group consisting of LDLK (SEQ ID NO: 91), KFEF (SEQ ID NO: 92), RADA (SEQ ID NO: 93), LDLD (SEQ ID NO: 94), and LKLK (SEQ ID NO: 95).

2. The self-assembling peptide according to claim 1, wherein said backbone region comprises at least one LDLK (SEQ ID NO: 91) amino acid repetition unit.

3. The self-assembling peptide according to claim 2, wherein said backbone region comprises three LDLK (SEQ ID NO: 91) amino acid repetitions.

4. The self-assembling peptide according to claim 1, wherein said backbone region comprises at least two KFEF (SEQ ID NO: 92) amino acid repetition units.

5. The self-assembling peptide according to claim 4, wherein said backbone region comprises three KFEF (SEQ ID NO: 92) amino acid repetitions.

6. The self-assembling peptide according to claim 1, wherein said backbone region comprises at least one RADA (SEQ ID NO: 93) amino acid repetition unit.

7. The self-assembling peptide according to claim 6, wherein said backbone region comprises three RADA (SEQ ID NO: 93) amino acid repetitions.

8. The self-assembling peptide according to claim 1, wherein said backbone region comprises at least one LDLD (SEQ ID NO: 94) amino acid repetition unit.

9. The self-assembling peptide according to claim 8, wherein said backbone region comprises three LDLD (SEQ ID NO: 94) amino acid repetitions.

10. The self-assembling peptide according to claim 1, wherein said backbone region comprises at least one LKLK (SEQ ID NO: 95) amino acid repetition unit.

11. The self-assembling peptide according to claim 10, wherein said backbone region comprises three LKLK (SEQ ID NO: 95) amino acid repetitions.

12. The self-assembling peptide according to claim 1, wherein said spacer region comprises three glycine amino acid units.

13. The self-assembling peptide according to claim 1, wherein said self-assembling peptide comprises a modified N-terminus.

14. The self-assembling peptide according to claim 13, wherein said N-terminus modification is an acetylation.

15. The self-assembling peptide according to claim 1, wherein said self-assembling peptide comprises a modified C-terminus.

16. The self-assembling peptide according to claim 15, wherein said C-terminus has a $CONH_2$ group.

17. The self-assembling peptide according to claim 1, wherein said self-assembling peptide comprises the amino acid sequence of X-KLPGWSGGGGLDLKLDLKLDLK (SEQ ID NO: 85)-Y;
   wherein X is $NH_2$ or Ac, and wherein Y is $CONH_2$ or COOH.

18. The self-assembling peptide according to claim 17, comprising:
   $NH_2$-KLPGWSGGGGLDLKLDLKLDLK-$CONH_2$ SEQ ID NO: 34.

19. The self-assembling peptide according to claim 17, comprising:
   Ac-KLPGWSGGGGLDLKLDLKLDLK-$CONH_2$ SEQ ID NO: 35.

20. A hydrogel comprising the self-assembling peptides according to claim 1 and a hydrogelating ingredient.

21. A self-assembling peptide polymer comprising at least two self-assembling peptides according to claim 1.

22. A tabular nanofiber comprising at least two self-assembling peptides according to claim 1.

23. A complex interwoven membrane comprising at least two tabular nanofibres according to claim 22.

24. A medicament comprising a self-assembling peptide polymer comprising at least two self-assembling peptides according to claim 1.

25. A method for using a self-assembling peptide polymer comprising at least two self-assembling peptides according to claim 1 as a scaffold in tissue regeneration comprising seeding the scaffold with cells and culturing the cells with the scaffold.

26. The method according to claim 25, wherein said tissue is a tissue of the central nervous system.

27. A method for using the self-assembling peptide according to claim 1, for use as a biomaterial and as a cell culture substrate comprising seeding the biomaterial with cells and culturing the cells with the biomaterial.

28. A method for using the heptapeptide according to claim 1, as a marker for neural stem cells comprising characterizing and isolating the neural stem cells.

* * * * *

SEQUENCE LISTING

```
<160> NUMBER OF SEQ ID NOS: 125

<210> SEQ ID NO 1
<211> LENGTH: 7
<212> TYPE: PRT
<213> ORGANISM: Artificial Sequence
<220> FEATURE:
<223> OTHER INFORMATION: Prepared by synthesis

<400> SEQUENCE: 1

Phe Ala Gln Arg Val Pro Pro
1               5

<210> SEQ ID NO 2
<211> LENGTH: 7
<212> TYPE: PRT
<213> ORGANISM: Artificial sequence
<220> FEATURE:
<223> OTHER INFORMATION: Prepared by synthesis

<400> SEQUENCE: 2

Gln His Leu Pro Arg Asp His
1               5

<210> SEQ ID NO 3
<211> LENGTH: 7
<212> TYPE: PRT
<213> ORGANISM: Artificial sequence
<220> FEATURE:
<223> OTHER INFORMATION: Prepared by synthesis
```

```
<400> SEQUENCE: 3

Ser Ser Leu Ser Val Asn Asp
1               5

<210> SEQ ID NO 4
<211> LENGTH: 7
<212> TYPE: PRT
<213> ORGANISM: Artificial sequence
<220> FEATURE:
<223> OTHER INFORMATION: Prepared by synthesis

<400> SEQUENCE: 4

Tyr Ile Ile Pro Met His Asp
1               5

<210> SEQ ID NO 5
<211> LENGTH: 7
<212> TYPE: PRT
<213> ORGANISM: Artificial sequence
<220> FEATURE:
<223> OTHER INFORMATION: Prepared by synthesis

<400> SEQUENCE: 5

Ser Leu Pro Lys Leu Pro Pro
1               5

<210> SEQ ID NO 6
<211> LENGTH: 7
<212> TYPE: PRT
<213> ORGANISM: Artificial sequence
<220> FEATURE:
<223> OTHER INFORMATION: Prepared by synthesis

<400> SEQUENCE: 6

Thr Pro Leu Ser Ser His Ser
1               5

<210> SEQ ID NO 7
<211> LENGTH: 7
<212> TYPE: PRT
<213> ORGANISM: Artificial sequence
<220> FEATURE:
<223> OTHER INFORMATION: Prepared by synthesis

<400> SEQUENCE: 7

Ser Ala Ser His Trp Gln Ile
1               5

<210> SEQ ID NO 8
<211> LENGTH: 7
<212> TYPE: PRT
<213> ORGANISM: Artificial sequence
<220> FEATURE:
<223> OTHER INFORMATION: Prepared by synthesis

<400> SEQUENCE: 8

Leu Gln Ala Ile Pro Arg Asn
1               5

<210> SEQ ID NO 9
<211> LENGTH: 7
<212> TYPE: PRT
<213> ORGANISM: Artificial sequence
<220> FEATURE:
<223> OTHER INFORMATION: Prepared by synthesis
```

```
<400> SEQUENCE: 9

Tyr Arg Met Pro Ile Trp Pro
1               5

<210> SEQ ID NO 10
<211> LENGTH: 7
<212> TYPE: PRT
<213> ORGANISM: Artificial sequence
<220> FEATURE:
<223> OTHER INFORMATION: Prepared by synthesis

<400> SEQUENCE: 10

Lys Leu Pro Gly Trp Ser Gly
1               5

<210> SEQ ID NO 11
<211> LENGTH: 7
<212> TYPE: PRT
<213> ORGANISM: Artificial sequence
<220> FEATURE:
<223> OTHER INFORMATION: Prepared by synthesis

<400> SEQUENCE: 11

His Ala Ile Tyr Pro Arg His
1               5

<210> SEQ ID NO 12
<211> LENGTH: 7
<212> TYPE: PRT
<213> ORGANISM: Artificial sequence
<220> FEATURE:
<223> OTHER INFORMATION: Prepared by synthesis

<400> SEQUENCE: 12

Gly Glu Thr Arg Ala Pro Leu
1               5

<210> SEQ ID NO 13
<211> LENGTH: 7
<212> TYPE: PRT
<213> ORGANISM: Artificial sequence
<220> FEATURE:
<223> OTHER INFORMATION: Prepared by synthesis

<400> SEQUENCE: 13

Ala Leu Thr Pro Trp Ala Phe
1               5

<210> SEQ ID NO 14
<211> LENGTH: 7
<212> TYPE: PRT
<213> ORGANISM: Artificial sequence
<220> FEATURE:
<223> OTHER INFORMATION: Prepared by synthesis

<400> SEQUENCE: 14

Gly Lys Pro Met Pro Pro Met
1               5

<210> SEQ ID NO 15
<211> LENGTH: 7
<212> TYPE: PRT
<213> ORGANISM: Artificial sequence
<220> FEATURE:
<223> OTHER INFORMATION: Prepared by synthesis
```

```
<400> SEQUENCE: 15

Ser Ile Leu Pro Tyr Pro Tyr
1               5

<210> SEQ ID NO 16
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 16

Phe Ala Gln Arg Val Pro Pro Gly Gly Gly Leu Asp Leu Lys Leu Asp
1               5                   10                  15

Leu Lys Leu Asp Leu Lys
            20

<210> SEQ ID NO 17
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 17

Phe Ala Gln Arg Val Pro Pro Gly Gly Gly Leu Asp Leu Lys Leu Asp
1               5                   10                  15

Leu Lys Leu Asp Leu Lys
            20

<210> SEQ ID NO 18
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 18

Gln His Leu Pro Arg Asp His Gly Gly Gly Leu Asp Leu Lys Leu Asp
1               5                   10                  15

Leu Lys Leu Asp Leu Lys
            20

<210> SEQ ID NO 19
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 19

Gln His Leu Pro Arg Asp His Gly Gly Gly Leu Asp Leu Lys Leu Asp
1               5                   10                  15

Leu Lys Leu Asp Leu Lys
            20

<210> SEQ ID NO 20
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 20

Ser Ser Leu Ser Val Asn Asp Gly Gly Gly Leu Asp Leu Lys Leu Asp
1               5                   10                  15

Leu Lys Leu Asp Leu Lys
            20

<210> SEQ ID NO 21
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 21

Ser Ser Leu Ser Val Asn Asp Gly Gly Gly Leu Asp Leu Lys Leu Asp
1               5                   10                  15

Leu Lys Leu Asp Leu Lys
            20

<210> SEQ ID NO 22
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 22

Tyr Ile Ile Pro Met His Asp Gly Gly Gly Leu Asp Leu Lys Leu Asp
1               5                   10                  15

Leu Lys Leu Asp Leu Lys
            20
```

```
<210> SEQ ID NO 23
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 23

Tyr Ile Ile Pro Met His Asp Gly Gly Gly Leu Asp Leu Lys Leu Asp
1               5                   10                  15

Leu Lys Leu Asp Leu Lys
            20

<210> SEQ ID NO 24
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 24

Ser Leu Pro Lys Leu Pro Pro Gly Gly Gly Leu Asp Leu Lys Leu Asp
1               5                   10                  15

Leu Lys Leu Asp Leu Lys
            20

<210> SEQ ID NO 25
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 25

Ser Leu Pro Lys Leu Pro Pro Gly Gly Gly Leu Asp Leu Lys Leu Asp
1               5                   10                  15

Leu Lys Leu Asp Leu Lys
            20

<210> SEQ ID NO 26
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION
```

```
<400> SEQUENCE: 26

Thr Pro Leu Ser Ser His Ser Gly Gly Gly Leu Asp Leu Lys Leu Asp
1               5                   10                  15

Leu Lys Leu Asp Leu Lys
            20

<210> SEQ ID NO 27
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 27

Thr Pro Leu Ser Ser His Ser Gly Gly Gly Leu Asp Leu Lys Leu Asp
1               5                   10                  15

Leu Lys Leu Asp Leu Lys
            20

<210> SEQ ID NO 28
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 28

Ser Ala Ser His Trp Gln Ile Gly Gly Gly Leu Asp Leu Lys Leu Asp
1               5                   10                  15

Leu Lys Leu Asp Leu Lys
            20

<210> SEQ ID NO 29
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 29

Ser Ala Ser His Trp Gln Ile Gly Gly Gly Leu Asp Leu Lys Leu Asp
1               5                   10                  15

Leu Lys Leu Asp Leu Lys
            20

<210> SEQ ID NO 30
<211> LENGTH: 22
```

```
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 30

Leu Gln Ala Ile Pro Arg Asn Gly Gly Gly Leu Asp Leu Lys Leu Asp
1               5                   10                  15

Leu Lys Leu Asp Leu Lys
            20

<210> SEQ ID NO 31
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 31

Leu Gln Ala Ile Pro Arg Asn Gly Gly Gly Leu Asp Leu Lys Leu Asp
1               5                   10                  15

Leu Lys Leu Asp Leu Lys
            20

<210> SEQ ID NO 32
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 32

Tyr Arg Met Pro Ile Trp Pro Gly Gly Gly Leu Asp Leu Lys Leu Asp
1               5                   10                  15

Leu Lys Leu Asp Leu Lys
            20

<210> SEQ ID NO 33
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 33
```

Tyr Arg Met Pro Ile Trp Pro Gly Gly Gly Leu Asp Leu Lys Leu Asp
1               5                   10                  15

Leu Lys Leu Asp Leu Lys
            20

<210> SEQ ID NO 34
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 34

Lys Leu Pro Gly Trp Ser Gly Gly Gly Leu Asp Leu Lys Leu Asp
1               5                   10                  15

Leu Lys Leu Asp Leu Lys
            20

<210> SEQ ID NO 35
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 35

Lys Leu Pro Gly Trp Ser Gly Gly Gly Leu Asp Leu Lys Leu Asp
1               5                   10                  15

Leu Lys Leu Asp Leu Lys
            20

<210> SEQ ID NO 36
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 36

His Ala Ile Tyr Pro Arg His Gly Gly Gly Leu Asp Leu Lys Leu Asp
1               5                   10                  15

Leu Lys Leu Asp Leu Lys
            20

<210> SEQ ID NO 37
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES

```
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 37

His Ala Ile Tyr Pro Arg His Gly Gly Gly Leu Asp Leu Lys Leu Asp
1               5                  10                  15

Leu Lys Leu Asp Leu Lys
            20

<210> SEQ ID NO 38
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 38

Gly Glu Thr Arg Ala Pro Leu Gly Gly Gly Leu Asp Leu Lys Leu Asp
1               5                  10                  15

Leu Lys Leu Asp Leu Lys
            20

<210> SEQ ID NO 39
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 39

Gly Glu Thr Arg Ala Pro Leu Gly Gly Gly Leu Asp Leu Lys Leu Asp
1               5                  10                  15

Leu Lys Leu Asp Leu Lys
            20

<210> SEQ ID NO 40
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 40

Ala Leu Thr Pro Trp Ala Phe Gly Gly Gly Leu Asp Leu Lys Leu Asp
1               5                  10                  15

Leu Lys Leu Asp Leu Lys
            20
```

```
<210> SEQ ID NO 41
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 41

Ala Leu Thr Pro Trp Ala Phe Gly Gly Gly Leu Asp Leu Lys Leu Asp
1               5                   10                  15

Leu Lys Leu Asp Leu Lys
            20

<210> SEQ ID NO 42
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION

<400> SEQUENCE: 42

Gly Lys Pro Met Pro Pro Met Gly Gly Gly Leu Asp Leu Lys Leu Asp
1               5                   10                  15

Leu Lys Leu Asp Leu Lys
            20

<210> SEQ ID NO 43
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 43

Gly Lys Pro Met Pro Pro Met Gly Gly Gly Leu Asp Leu Lys Leu Asp
1               5                   10                  15

Leu Lys Leu Asp Leu Lys
            20

<210> SEQ ID NO 44
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (22)..(22)
<223> OTHER INFORMATION: AMIDATION
```

```
<400> SEQUENCE: 44

Ser Ile Leu Pro Tyr Pro Tyr Gly Gly Gly Leu Asp Leu Lys Leu Asp
1               5                   10                  15

Leu Lys Leu Asp Leu Lys
            20

<210> SEQ ID NO 45
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 45

Ser Ile Leu Pro Tyr Pro Tyr Gly Gly Gly Leu Asp Leu Lys Leu Asp
1               5                   10                  15

Leu Lys Leu Asp Leu Lys
            20

<210> SEQ ID NO 46
<211> LENGTH: 22
<212> TYPE: PRT
<213> ORGANISM: Artificial sequence
<220> FEATURE:
<223> OTHER INFORMATION: Prepared by synthesis

<400> SEQUENCE: 46

Phe Ala Gln Arg Val Pro Pro Gly Gly Gly Leu Asp Leu Lys Leu Asp
1               5                   10                  15

Leu Lys Leu Asp Leu Lys
            20

<210> SEQ ID NO 47
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 47

Phe Ala Gln Arg Val Pro Pro Gly Gly Gly Leu Asp Leu Lys Leu Asp
1               5                   10                  15

Leu Lys Leu Asp Leu Lys
            20

<210> SEQ ID NO 48
<211> LENGTH: 22
<212> TYPE: PRT
<213> ORGANISM: Artificial sequence
<220> FEATURE:
<223> OTHER INFORMATION: Prepared by synthesis

<400> SEQUENCE: 48
```

Gln His Leu Pro Arg Asp His Gly Gly Gly Leu Asp Leu Lys Leu Asp
1               5                   10                  15

Leu Lys Leu Asp Leu Lys
            20

<210> SEQ ID NO 49
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 49

Gln His Leu Pro Arg Asp His Gly Gly Gly Leu Asp Leu Lys Leu Asp
1               5                   10                  15

Leu Lys Leu Asp Leu Lys
            20

<210> SEQ ID NO 50
<211> LENGTH: 22
<212> TYPE: PRT
<213> ORGANISM: Artificial sequence
<220> FEATURE:
<223> OTHER INFORMATION: Prepared by synthesis

<400> SEQUENCE: 50

Ser Ser Leu Ser Val Asn Asp Gly Gly Gly Leu Asp Leu Lys Leu Asp
1               5                   10                  15

Leu Lys Leu Asp Leu Lys
            20

<210> SEQ ID NO 51
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 51

Ser Ser Leu Ser Val Asn Asp Gly Gly Gly Leu Asp Leu Lys Leu Asp
1               5                   10                  15

Leu Lys Leu Asp Leu Lys
            20

<210> SEQ ID NO 52
<211> LENGTH: 22
<212> TYPE: PRT
<213> ORGANISM: Artificial sequence
<220> FEATURE:
<223> OTHER INFORMATION: Prepared by synthesis

<400> SEQUENCE: 52

Tyr Ile Ile Pro Met His Asp Gly Gly Gly Leu Asp Leu Lys Leu Asp
1               5                   10                  15

Leu Lys Leu Asp Leu Lys
            20

```
<210> SEQ ID NO 53
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 53

Tyr Ile Ile Pro Met His Asp Gly Gly Gly Leu Asp Leu Lys Leu Asp
1               5                   10                  15

Leu Lys Leu Asp Leu Lys
            20

<210> SEQ ID NO 54
<211> LENGTH: 22
<212> TYPE: PRT
<213> ORGANISM: Artificial sequence
<220> FEATURE:
<223> OTHER INFORMATION: Prepared by synthesis

<400> SEQUENCE: 54

Ser Leu Pro Lys Leu Pro Pro Gly Gly Gly Leu Asp Leu Lys Leu Asp
1               5                   10                  15

Leu Lys Leu Asp Leu Lys
            20

<210> SEQ ID NO 55
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 55

Ser Leu Pro Lys Leu Pro Pro Gly Gly Gly Leu Asp Leu Lys Leu Asp
1               5                   10                  15

Leu Lys Leu Asp Leu Lys
            20

<210> SEQ ID NO 56
<211> LENGTH: 22
<212> TYPE: PRT
<213> ORGANISM: Artificial sequence
<220> FEATURE:
<223> OTHER INFORMATION: Prepared by synthesis

<400> SEQUENCE: 56

Thr Pro Leu Ser Ser His Ser Gly Gly Gly Leu Asp Leu Lys Leu Asp
1               5                   10                  15

Leu Lys Leu Asp Leu Lys
            20

<210> SEQ ID NO 57
<211> LENGTH: 22
<212> TYPE: PRT
<213> ORGANISM: Artificial sequence
<220> FEATURE:
<223> OTHER INFORMATION: Prepared by synthesis
<220> FEATURE:
```

```
<221> NAME/KEY: MOD_RES
<222> LOCATION: (1)..(1)
<223> OTHER INFORMATION: ACETYLATION

<400> SEQUENCE: 57

Thr Pro Leu Ser Ser His Ser Gly Gly Gly Leu Asp Leu Lys Leu Asp
1               5                   10                  15

Leu Lys Leu Asp Leu Lys
            20

<210> SEQ ID NO 58
<211> LENGTH: 22
<212> TYPE: PRT
<213> ORGANISM: Artificial sequence
<220> FEATURE:
<223> OTHER INFORMATION: Prepared by synthesis

<400> SEQUENCE: 58

Ser Ala Ser His Trp Gln Ile Gly Gly Gly Leu Asp Leu Lys Leu Asp
1               5                   10                  15

Leu Lys Leu Asp Leu Lys
            20

<210> SEQ ID NO 59
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 59

Ser Ala Ser His Trp Gln Ile Gly Gly Gly Leu Asp Leu Lys Leu Asp
1               5                   10                  15

Leu Lys Leu Asp Leu Lys
            20

<210> SEQ ID NO 60
<211> LENGTH: 22
<212> TYPE: PRT
<213> ORGANISM: Artificial sequence
<220> FEATURE:
<223> OTHER INFORMATION: Prepared by synthesis

<400> SEQUENCE: 60

Leu Gln Ala Ile Pro Arg Asn Gly Gly Gly Leu Asp Leu Lys Leu Asp
1               5                   10                  15

Leu Lys Leu Asp Leu Lys
            20

<210> SEQ ID NO 61
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 61

Leu Gln Ala Ile Pro Arg Asn Gly Gly Gly Leu Asp Leu Lys Leu Asp
```

```
                 1               5                  10                 15

Leu Lys Leu Asp Leu Lys
            20

<210> SEQ ID NO 62
<211> LENGTH: 22
<212> TYPE: PRT
<213> ORGANISM: Artificial sequence
<220> FEATURE:
<223> OTHER INFORMATION: Prepared by synthesis

<400> SEQUENCE: 62

Tyr Arg Met Pro Ile Trp Pro Gly Gly Gly Leu Asp Leu Lys Leu Asp
1               5                   10                  15

Leu Lys Leu Asp Leu Lys
            20

<210> SEQ ID NO 63
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 63

Tyr Arg Met Pro Ile Trp Pro Gly Gly Gly Leu Asp Leu Lys Leu Asp
1               5                   10                  15

Leu Lys Leu Asp Leu Lys
            20

<210> SEQ ID NO 64
<211> LENGTH: 22
<212> TYPE: PRT
<213> ORGANISM: Artificial sequence
<220> FEATURE:
<223> OTHER INFORMATION: Prepared by synthesis

<400> SEQUENCE: 64

Lys Leu Pro Gly Trp Ser Gly Gly Gly Leu Asp Leu Lys Leu Asp
1               5                   10                  15

Leu Lys Leu Asp Leu Lys
            20

<210> SEQ ID NO 65
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 65

Lys Leu Pro Gly Trp Ser Gly Gly Gly Leu Asp Leu Lys Leu Asp
1               5                   10                  15

Leu Lys Leu Asp Leu Lys
            20

<210> SEQ ID NO 66
```

```
<211> LENGTH: 22
<212> TYPE: PRT
<213> ORGANISM: Artificial sequence
<220> FEATURE:
<223> OTHER INFORMATION: Prepared by synthesis

<400> SEQUENCE: 66

His Ala Ile Tyr Pro Arg His Gly Gly Gly Leu Asp Leu Lys Leu Asp
1               5                   10                  15

Leu Lys Leu Asp Leu Lys
            20

<210> SEQ ID NO 67
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 67

His Ala Ile Tyr Pro Arg His Gly Gly Gly Leu Asp Leu Lys Leu Asp
1               5                   10                  15

Leu Lys Leu Asp Leu Lys
            20

<210> SEQ ID NO 68
<211> LENGTH: 22
<212> TYPE: PRT
<213> ORGANISM: Artificial sequence
<220> FEATURE:
<223> OTHER INFORMATION: Prepared by synthesis

<400> SEQUENCE: 68

Gly Glu Thr Arg Ala Pro Leu Gly Gly Gly Leu Asp Leu Lys Leu Asp
1               5                   10                  15

Leu Lys Leu Asp Leu Lys
            20

<210> SEQ ID NO 69
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 69

Gly Glu Thr Arg Ala Pro Leu Gly Gly Gly Leu Asp Leu Lys Leu Asp
1               5                   10                  15

Leu Lys Leu Asp Leu Lys
            20

<210> SEQ ID NO 70
<211> LENGTH: 22
<212> TYPE: PRT
<213> ORGANISM: Artificial sequence
<220> FEATURE:
<223> OTHER INFORMATION: Prepared by synthesis

<400> SEQUENCE: 70
```

Ala Leu Thr Pro Trp Ala Phe Gly Gly Gly Leu Asp Leu Lys Leu Asp
1               5                   10                  15

Leu Lys Leu Asp Leu Lys
            20

<210> SEQ ID NO 71
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 71

Ala Leu Thr Pro Trp Ala Phe Gly Gly Gly Leu Asp Leu Lys Leu Asp
1               5                   10                  15

Leu Lys Leu Asp Leu Lys
            20

<210> SEQ ID NO 72
<211> LENGTH: 22
<212> TYPE: PRT
<213> ORGANISM: Artificial sequence
<220> FEATURE:
<223> OTHER INFORMATION: Prepared by synthesis

<400> SEQUENCE: 72

Gly Lys Pro Met Pro Pro Met Gly Gly Gly Leu Asp Leu Lys Leu Asp
1               5                   10                  15

Leu Lys Leu Asp Leu Lys
            20

<210> SEQ ID NO 73
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 73

Gly Lys Pro Met Pro Pro Met Gly Gly Gly Leu Asp Leu Lys Leu Asp
1               5                   10                  15

Leu Lys Leu Asp Leu Lys
            20

<210> SEQ ID NO 74
<211> LENGTH: 22
<212> TYPE: PRT
<213> ORGANISM: Artificial sequence
<220> FEATURE:
<223> OTHER INFORMATION: Prepared by synthesis

<400> SEQUENCE: 74

Ser Ile Leu Pro Tyr Pro Tyr Gly Gly Gly Leu Asp Leu Lys Leu Asp
1               5                   10                  15

Leu Lys Leu Asp Leu Lys
            20

<210> SEQ ID NO 75
<211> LENGTH: 22
<212> TYPE: PRT
<213> ORGANISM: Artificial sequence
<220> FEATURE:
<223> OTHER INFORMATION: Prepared by synthesis
<220> FEATURE:
<221> NAME/KEY: MOD_RES
<222> LOCATION: (1)..(1)
<223> OTHER INFORMATION: ACETYLATION

<400> SEQUENCE: 75

Ser Ile Leu Pro Tyr Pro Tyr Gly Gly Gly Leu Asp Leu Lys Leu Asp
1               5                   10                  15

Leu Lys Leu Asp Leu Lys
            20

<210> SEQ ID NO 76
<211> LENGTH: 22
<212> TYPE: PRT
<213> ORGANISM: Artificial
<220> FEATURE:
<223> OTHER INFORMATION: Prepared by synthesis

<400> SEQUENCE: 76

Phe Ala Gln Arg Val Pro Pro Gly Gly Gly Leu Asp Leu Lys Leu Asp
1               5                   10                  15

Leu Lys Leu Asp Leu Lys
            20

<210> SEQ ID NO 77
<211> LENGTH: 22
<212> TYPE: PRT
<213> ORGANISM: Artificial
<220> FEATURE:
<223> OTHER INFORMATION: Prepared by synthesis

<400> SEQUENCE: 77

Gln His Leu Pro Arg Asp His Gly Gly Gly Leu Asp Leu Lys Leu Asp
1               5                   10                  15

Leu Lys Leu Asp Leu Lys
            20

<210> SEQ ID NO 78
<211> LENGTH: 22
<212> TYPE: PRT
<213> ORGANISM: Artificial
<220> FEATURE:
<223> OTHER INFORMATION: Prepared by synthesis

<400> SEQUENCE: 78

Ser Ser Leu Ser Val Asn Asp Gly Gly Gly Leu Asp Leu Lys Leu Asp
1               5                   10                  15

Leu Lys Leu Asp Leu Lys
            20

<210> SEQ ID NO 79
<211> LENGTH: 22
<212> TYPE: PRT
<213> ORGANISM: Artificial
<220> FEATURE:
<223> OTHER INFORMATION: Prepared by synthesis

<400> SEQUENCE: 79

Tyr Ile Ile Pro Met His Asp Gly Gly Gly Leu Asp Leu Lys Leu Asp

```
1               5                   10                  15
Leu Lys Leu Asp Leu Lys
            20

<210> SEQ ID NO 80
<211> LENGTH: 22
<212> TYPE: PRT
<213> ORGANISM: Artificial
<220> FEATURE:
<223> OTHER INFORMATION: Prepared by synthesis

<400> SEQUENCE: 80

Ser Leu Pro Lys Leu Pro Pro Gly Gly Gly Leu Asp Leu Lys Leu Asp
1               5                   10                  15

Leu Lys Leu Asp Leu Lys
            20

<210> SEQ ID NO 81
<211> LENGTH: 22
<212> TYPE: PRT
<213> ORGANISM: Artificial
<220> FEATURE:
<223> OTHER INFORMATION: Prepared by synthesis

<400> SEQUENCE: 81

Thr Pro Leu Ser Ser His Ser Gly Gly Gly Leu Asp Leu Lys Leu Asp
1               5                   10                  15

Leu Lys Leu Asp Leu Lys
            20

<210> SEQ ID NO 82
<211> LENGTH: 22
<212> TYPE: PRT
<213> ORGANISM: Artificial
<220> FEATURE:
<223> OTHER INFORMATION: Prepared by synthesis

<400> SEQUENCE: 82

Ser Ala Ser His Trp Gln Ile Gly Gly Gly Leu Asp Leu Lys Leu Asp
1               5                   10                  15

Leu Lys Leu Asp Leu Lys
            20

<210> SEQ ID NO 83
<211> LENGTH: 22
<212> TYPE: PRT
<213> ORGANISM: Artificial
<220> FEATURE:
<223> OTHER INFORMATION: Prepared by synthesis

<400> SEQUENCE: 83

Leu Gln Ala Ile Pro Arg Asn Gly Gly Gly Leu Asp Leu Lys Leu Asp
1               5                   10                  15

Leu Lys Leu Asp Leu Lys
            20

<210> SEQ ID NO 84
<211> LENGTH: 22
<212> TYPE: PRT
<213> ORGANISM: Artificial
<220> FEATURE:
<223> OTHER INFORMATION: Prepared by synthesis

<400> SEQUENCE: 84
```

```
Tyr Arg Met Pro Ile Trp Pro Gly Gly Gly Leu Asp Leu Lys Leu Asp
1               5                   10                  15

Leu Lys Leu Asp Leu Lys
            20

<210> SEQ ID NO 85
<211> LENGTH: 22
<212> TYPE: PRT
<213> ORGANISM: Artificial
<220> FEATURE:
<223> OTHER INFORMATION: Prepared by synthesis

<400> SEQUENCE: 85

Lys Leu Pro Gly Trp Ser Gly Gly Gly Leu Asp Leu Lys Leu Asp
1               5                   10                  15

Leu Lys Leu Asp Leu Lys
            20

<210> SEQ ID NO 86
<211> LENGTH: 22
<212> TYPE: PRT
<213> ORGANISM: Artificial
<220> FEATURE:
<223> OTHER INFORMATION: Prepared by synthesis

<400> SEQUENCE: 86

His Ala Ile Tyr Pro Arg His Gly Gly Gly Leu Asp Leu Lys Leu Asp
1               5                   10                  15

Leu Lys Leu Asp Leu Lys
            20

<210> SEQ ID NO 87
<211> LENGTH: 22
<212> TYPE: PRT
<213> ORGANISM: Artificial
<220> FEATURE:
<223> OTHER INFORMATION: Prepared by synthesis

<400> SEQUENCE: 87

Gly Glu Thr Arg Ala Pro Leu Gly Gly Gly Leu Asp Leu Lys Leu Asp
1               5                   10                  15

Leu Lys Leu Asp Leu Lys
            20

<210> SEQ ID NO 88
<211> LENGTH: 22
<212> TYPE: PRT
<213> ORGANISM: Artificial
<220> FEATURE:
<223> OTHER INFORMATION: Prepared by synthesis

<400> SEQUENCE: 88

Ala Leu Thr Pro Trp Ala Phe Gly Gly Gly Leu Asp Leu Lys Leu Asp
1               5                   10                  15

Leu Lys Leu Asp Leu Lys
            20

<210> SEQ ID NO 89
<211> LENGTH: 22
<212> TYPE: PRT
<213> ORGANISM: Artificial
<220> FEATURE:
<223> OTHER INFORMATION: Prepared by synthesis

<400> SEQUENCE: 89
```

```
Gly Lys Pro Met Pro Pro Met Gly Gly Gly Leu Asp Leu Lys Leu Asp
1               5                   10                  15

Leu Lys Leu Asp Leu Lys
            20

<210> SEQ ID NO 90
<211> LENGTH: 22
<212> TYPE: PRT
<213> ORGANISM: Artificial
<220> FEATURE:
<223> OTHER INFORMATION: Prepared by synthesis

<400> SEQUENCE: 90

Ser Ile Leu Pro Tyr Pro Tyr Gly Gly Gly Leu Asp Leu Lys Leu Asp
1               5                   10                  15

Leu Lys Leu Asp Leu Lys
            20

<210> SEQ ID NO 91
<211> LENGTH: 4
<212> TYPE: PRT
<213> ORGANISM: Artificial
<220> FEATURE:
<223> OTHER INFORMATION: Prepared by synthesis

<400> SEQUENCE: 91

Leu Asp Leu Lys
1

<210> SEQ ID NO 92
<211> LENGTH: 4
<212> TYPE: PRT
<213> ORGANISM: Artificial
<220> FEATURE:
<223> OTHER INFORMATION: Prepared by synthesis

<400> SEQUENCE: 92

Lys Phe Glu Phe
1

<210> SEQ ID NO 93
<211> LENGTH: 4
<212> TYPE: PRT
<213> ORGANISM: Artificial
<220> FEATURE:
<223> OTHER INFORMATION: Prepared by synthesis

<400> SEQUENCE: 93

Arg Ala Asp Ala
1

<210> SEQ ID NO 94
<211> LENGTH: 4
<212> TYPE: PRT
<213> ORGANISM: Artificial
<220> FEATURE:
<223> OTHER INFORMATION: Prepared by synthesis

<400> SEQUENCE: 94

Leu Asp Leu Asp
1

<210> SEQ ID NO 95
<211> LENGTH: 4
<212> TYPE: PRT
```

```
<213> ORGANISM: Artificial
<220> FEATURE:
<223> OTHER INFORMATION: Prepared by synthesis

<400> SEQUENCE: 95

Leu Lys Leu Lys
1

<210> SEQ ID NO 96
<211> LENGTH: 8
<212> TYPE: PRT
<213> ORGANISM: Artificial
<220> FEATURE:
<223> OTHER INFORMATION: Prepared by synthesis

<400> SEQUENCE: 96

Leu Asp Leu Lys Leu Asp Leu Lys
1               5

<210> SEQ ID NO 97
<211> LENGTH: 8
<212> TYPE: PRT
<213> ORGANISM: Artificial
<220> FEATURE:
<223> OTHER INFORMATION: Prepared by synthesis

<400> SEQUENCE: 97

Lys Phe Glu Phe Lys Phe Glu Phe
1               5

<210> SEQ ID NO 98
<211> LENGTH: 10
<212> TYPE: PRT
<213> ORGANISM: Artificial
<220> FEATURE:
<223> OTHER INFORMATION: Prepared by synthesis

<400> SEQUENCE: 98

Gly Gly Gly Pro Phe Ser Ser Thr Lys Thr
1               5                   10

<210> SEQ ID NO 99
<211> LENGTH: 11
<212> TYPE: PRT
<213> ORGANISM: Artificial
<220> FEATURE:
<223> OTHER INFORMATION: Prepared by synthesis

<400> SEQUENCE: 99

Trp Gly Gly Gly Pro Phe Ser Ser Thr Lys Thr
1               5                   10

<210> SEQ ID NO 100
<211> LENGTH: 10
<212> TYPE: PRT
<213> ORGANISM: Artificial
<220> FEATURE:
<223> OTHER INFORMATION: Prepared by synthesis

<400> SEQUENCE: 100

Gly Gly Gly Pro Phe Ser Ser Thr Asp Thr
1               5                   10

<210> SEQ ID NO 101
<211> LENGTH: 10
<212> TYPE: PRT
<213> ORGANISM: Artificial
```

```
<220> FEATURE:
<223> OTHER INFORMATION: Prepared by synthesis

<400> SEQUENCE: 101

Gly Gly Gly Pro Phe Ser Ser Thr Asn Thr
1               5                   10

<210> SEQ ID NO 102
<211> LENGTH: 10
<212> TYPE: PRT
<213> ORGANISM: Artificial
<220> FEATURE:
<223> OTHER INFORMATION: Prepared by synthesis

<400> SEQUENCE: 102

Gly Gly Gly Pro Phe Ser Ser Thr Glu Thr
1               5                   10

<210> SEQ ID NO 103
<211> LENGTH: 10
<212> TYPE: PRT
<213> ORGANISM: Artificial
<220> FEATURE:
<223> OTHER INFORMATION: Prepared by synthesis

<400> SEQUENCE: 103

Gly Gly Gly Pro Phe Ser Ser Thr Gln Thr
1               5                   10

<210> SEQ ID NO 104
<211> LENGTH: 10
<212> TYPE: PRT
<213> ORGANISM: Artificial
<220> FEATURE:
<223> OTHER INFORMATION: Prepared by synthesis

<400> SEQUENCE: 104

Gly Gly Gly Ala Phe Ser Ser Thr Lys Thr
1               5                   10

<210> SEQ ID NO 105
<211> LENGTH: 10
<212> TYPE: PRT
<213> ORGANISM: Artificial
<220> FEATURE:
<223> OTHER INFORMATION: Prepared by synthesis

<400> SEQUENCE: 105

Gly Gly Gly Pro Phe Ser Glu Thr Lys Thr
1               5                   10

<210> SEQ ID NO 106
<211> LENGTH: 14
<212> TYPE: PRT
<213> ORGANISM: Artificial
<220> FEATURE:
<223> OTHER INFORMATION: Prepared by synthesis

<400> SEQUENCE: 106

Gly Gly Gly Ala Phe Ser Ser Thr Lys Thr Gly Arg Gly Asp
1               5                   10

<210> SEQ ID NO 107
<211> LENGTH: 10
<212> TYPE: PRT
<213> ORGANISM: Artificial
<220> FEATURE:
```

```
<223> OTHER INFORMATION: Prepared by synthesis

<400> SEQUENCE: 107

Gly Gly Gly Pro Phe Ser Ser Thr Arg Thr
1               5                   10

<210> SEQ ID NO 108
<211> LENGTH: 10
<212> TYPE: PRT
<213> ORGANISM: Artificial
<220> FEATURE:
<223> OTHER INFORMATION: Prepared by synthesis

<400> SEQUENCE: 108

Gly Gly Gly Ala Phe Ala Ser Thr Lys Thr
1               5                   10

<210> SEQ ID NO 109
<211> LENGTH: 12
<212> TYPE: PRT
<213> ORGANISM: Artificial
<220> FEATURE:
<223> OTHER INFORMATION: Prepared by synthesis

<400> SEQUENCE: 109

Gly Gly Gly Gly Gly Pro Phe Ser Ser Thr Lys Thr
1               5                   10

<210> SEQ ID NO 110
<211> LENGTH: 10
<212> TYPE: PRT
<213> ORGANISM: Artificial
<220> FEATURE:
<223> OTHER INFORMATION: Prepared by synthesis

<400> SEQUENCE: 110

Gly Gly Gly Pro Trp Ser Ser Thr Lys Thr
1               5                   10

<210> SEQ ID NO 111
<211> LENGTH: 9
<212> TYPE: PRT
<213> ORGANISM: Artificial
<220> FEATURE:
<223> OTHER INFORMATION: Prepared by synthesis

<400> SEQUENCE: 111

Gly Gly Gly Phe Ser Ser Thr Lys Thr
1               5

<210> SEQ ID NO 112
<211> LENGTH: 11
<212> TYPE: PRT
<213> ORGANISM: Artificial
<220> FEATURE:
<223> OTHER INFORMATION: Prepared by synthesis

<400> SEQUENCE: 112

Trp Gly Gly Gly Ala Phe Ala Ser Thr Lys Thr
1               5                   10

<210> SEQ ID NO 113
<211> LENGTH: 11
<212> TYPE: PRT
<213> ORGANISM: Artificial
<220> FEATURE:
<223> OTHER INFORMATION: Prepared by synthesis
```

```
<400> SEQUENCE: 113

Trp Gly Gly Gly Ala Phe Ser Ser Thr Lys Thr
1               5                   10

<210> SEQ ID NO 114
<211> LENGTH: 10
<212> TYPE: PRT
<213> ORGANISM: Artificial
<220> FEATURE:
<223> OTHER INFORMATION: Prepared by synthesis

<400> SEQUENCE: 114

Gly Gly Gly Lys Phe Ser Ser Thr Pro Thr
1               5                   10

<210> SEQ ID NO 115
<211> LENGTH: 10
<212> TYPE: PRT
<213> ORGANISM: Artificial
<220> FEATURE:
<223> OTHER INFORMATION: Prepared by synthesis

<400> SEQUENCE: 115

Gly Gly Gly Pro Lys Ser Ser Thr Phe Thr
1               5                   10

<210> SEQ ID NO 116
<211> LENGTH: 10
<212> TYPE: PRT
<213> ORGANISM: Artificial
<220> FEATURE:
<223> OTHER INFORMATION: Prepared by synthesis

<400> SEQUENCE: 116

Gly Gly Gly Pro Phe Ser Ser Lys Thr Thr
1               5                   10

<210> SEQ ID NO 117
<211> LENGTH: 10
<212> TYPE: PRT
<213> ORGANISM: Artificial
<220> FEATURE:
<223> OTHER INFORMATION: Prepared by synthesis

<400> SEQUENCE: 117

Gly Gly Gly Pro Phe Ser Ser Thr Thr Lys
1               5                   10

<210> SEQ ID NO 118
<211> LENGTH: 7
<212> TYPE: PRT
<213> ORGANISM: Artificial
<220> FEATURE:
<223> OTHER INFORMATION: Prepared by synthesis

<400> SEQUENCE: 118

Pro Phe Ser Ser Thr Lys Thr
1               5

<210> SEQ ID NO 119
<211> LENGTH: 12
<212> TYPE: PRT
<213> ORGANISM: Artificial
<220> FEATURE:
<223> OTHER INFORMATION: Prepared by synthesis
```

```
<400> SEQUENCE: 119

Leu Asp Leu Lys Leu Asp Leu Lys Leu Asp Leu Lys
1               5                   10

<210> SEQ ID NO 120
<211> LENGTH: 16
<212> TYPE: PRT
<213> ORGANISM: Artificial
<220> FEATURE:
<223> OTHER INFORMATION: Prepared by synthesis

<400> SEQUENCE: 120

Leu Asp Leu Lys Leu Asp Leu Lys Leu Asp Leu Lys Leu Asp Leu Lys
1               5                   10                  15

<210> SEQ ID NO 121
<211> LENGTH: 7
<212> TYPE: PRT
<213> ORGANISM: Artificial
<220> FEATURE:
<223> OTHER INFORMATION: Prepared by synthesis

<400> SEQUENCE: 121

Ser Ser Glu Leu Val Thr His
1               5

<210> SEQ ID NO 122
<211> LENGTH: 7
<212> TYPE: PRT
<213> ORGANISM: Artificial
<220> FEATURE:
<223> OTHER INFORMATION: Prepared by synthesis

<400> SEQUENCE: 122

Thr Ala Val Asn Ser Asp Ala
1               5

<210> SEQ ID NO 123
<211> LENGTH: 7
<212> TYPE: PRT
<213> ORGANISM: Artificial
<220> FEATURE:
<223> OTHER INFORMATION: Prepared by synthesis

<400> SEQUENCE: 123

Thr Pro Pro Phe Ala Ala Trp
1               5

<210> SEQ ID NO 124
<211> LENGTH: 7
<212> TYPE: PRT
<213> ORGANISM: Artificial
<220> FEATURE:
<223> OTHER INFORMATION: Prepared by synthesis

<400> SEQUENCE: 124

Thr Thr Thr Pro Thr Thr Pro
1               5

<210> SEQ ID NO 125
<211> LENGTH: 7
<212> TYPE: PRT
<213> ORGANISM: Artificial
<220> FEATURE:
<223> OTHER INFORMATION: Prepared by synthesis
```

```
<400> SEQUENCE: 125

Leu Thr Thr Gly Ser Gly Ser
1               5
```